United States Patent
Karp et al.

(10) Patent No.: US 11,021,687 B2
(45) Date of Patent: Jun. 1, 2021

(54) PRODUCTION OF DIFFERENTIATED ENTEROENDOCRINE CELLS AND INSULIN PRODUCING CELLS

(71) Applicants: Massachusetts Institute of Technology, Cambridge, MA (US); The Brigham and Women's Hospital, Inc., Boston, MA (US)

(72) Inventors: Jeffrey Michael Karp, Brookline, MA (US); Robert Samuel Langer, Newton, MA (US); Xiaolei Yin, Quincy, MA (US)

(73) Assignees: The Brigham And Women's Hospital, Inc., Boston, MA (US); Massachusetts Institute Of Technology, Cambridge, MA (US)

( * ) Notice: Subject to any disclaimer, the term of this patent is extended or adjusted under 35 U.S.C. 154(b) by 0 days.

(21) Appl. No.: 15/400,877

(22) Filed: Jan. 6, 2017

(65) Prior Publication Data
US 2017/0349884 A1 Dec. 7, 2017

Related U.S. Application Data

(60) Provisional application No. 62/276,814, filed on Jan. 8, 2016.

(51) Int. Cl.
*C12N 5/071* (2010.01)
*G01N 33/50* (2006.01)

(52) U.S. Cl.
CPC ......... *C12N 5/0678* (2013.01); *C12N 5/0613* (2013.01); *C12N 5/0679* (2013.01); *G01N 33/5008* (2013.01); *C12N 2500/38* (2013.01); *C12N 2500/62* (2013.01); *C12N 2501/01* (2013.01); *C12N 2501/065* (2013.01); *C12N 2501/11* (2013.01); *C12N 2501/119* (2013.01); *C12N 2501/13* (2013.01); *C12N 2501/15* (2013.01); *C12N 2501/155* (2013.01); *C12N 2501/335* (2013.01); *C12N 2501/395* (2013.01); *C12N 2501/415* (2013.01); *C12N 2501/42* (2013.01); *C12N 2501/71* (2013.01); *C12N 2501/72* (2013.01); *C12N 2501/727* (2013.01); *C12N 2501/999* (2013.01); *C12N 2502/23* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,059,591 A | 10/1991 | Janoff et al. | |
| 5,421,818 A | 6/1995 | Arenberg | |
| 5,474,529 A | 12/1995 | Arenberg | |
| 5,476,446 A | 12/1995 | Arenberg | |
| 5,731,144 A | 3/1998 | Toothman et al. | |
| 5,731,424 A | 3/1998 | Toothman et al. | |
| 5,837,681 A | 11/1998 | Magal | |
| 6,045,528 A | 4/2000 | Arenberg et al. | |
| 6,124,449 A | 6/2000 | Gold et al. | |
| 6,090,383 A | 7/2000 | Dasch et al. | |
| 6,177,434 B1 | 1/2001 | Kopke et al. | |
| 6,419,928 B1 | 7/2002 | Dasch et al. | |
| 6,476,031 B1 | 11/2002 | Chakravarty et al. | |
| 6,509,318 B1 | 1/2003 | Bhatnagar et al. | |
| 6,593,290 B1 | 7/2003 | Gao | |
| 6,943,191 B1 | 9/2005 | Narayanan et al. | |
| 7,030,125 B2 | 4/2006 | Munchhof et al. | |
| 7,087,626 B2 | 8/2006 | Beight et al. | |
| 7,151,169 B2 | 12/2006 | Thompson et al. | |
| 7,223,766 B2 | 5/2007 | Dugar et al. | |
| 7,387,614 B2 | 6/2008 | Staecker | |
| 7,498,031 B2 | 3/2009 | Fujioka et al. | |

(Continued)

FOREIGN PATENT DOCUMENTS

| | | |
|---|---|---|
| CA | 2268331 A1 | 5/1998 |
| CN | 1319968 C | 10/2005 |

(Continued)

OTHER PUBLICATIONS

Mimasu et al (Biochemical and Biophysical Research Communications, 2008, vol. 366, pp. 15-22).*
Alford, et al., "American College of Medical Genetics and Genomics Guideline for the Clinical Evaluation and Etiologic Diagnosis of Hearing Loss," Genetics in Medicine: Official Journal of the American College of Medical Genetics, vol. 16, pp. 347-355, 2014.
Almeida, et al., "In Situ Gelling Systems: A Strategy to Improve the Bioavailability of Ophthalmic Pharmaceutical Formulations," Drug Discov. Today, 19(4):400-12, (Apr. 2014), (Epub Oct. 11, 2013).
Arnold, et al., "Zinc for Attention-Deficit/Hyperactivity Disorder: Placebo-Controlled Double-Blind Pilot Trial Alone and Combined with Amphetamine," Journal of Child and Adolescent Psychopharmacology, vol. 21(1):1-19 (Jan. 2011).

(Continued)

*Primary Examiner* — Nancy J Leith
(74) *Attorney, Agent, or Firm* — Hamilton, Brook, Smith & Reynolds, P.C.

(57) ABSTRACT

A population of enteroendocrine cells (EEC) is obtained from a mammalian post-natal cell population, such as a population including post-natal stem cells, by treating the population with a plurality of small molecules that upregulate ChgA and promote differentiation of the cells to form the enteroendocrine cells. The upregulation of ChgA is such that the fraction of cells expressing CGA in the obtained cell population, as measured by a ChgA Immunostaining Assay, is at least about 1.5%. Small molecules that can be used to differentiate the post-natal cells into the enteroendocrine cells can include at least one of a Wnt activator, a Notch inhibitor, a Wnt inhibitor, a MEK/ERK inhibitor, a growth factor, a HDAC inhibitor, a Histone Methylation Inhibitor, a Tgf-β inhibitor, and a NeuroD1 activator. Also, the insulin expression of a population of mammalian cells is increased by treating the population with a plurality of small molecules that increase the insulin expression.

29 Claims, 48 Drawing Sheets
(42 of 48 Drawing Sheet(s) Filed in Color)

(56) References Cited

U.S. PATENT DOCUMENTS

| | | |
|---|---|---|
| 7,514,445 B2 | 4/2009 | Freyne et al. |
| 7,723,486 B2 | 5/2010 | Ledbetter et al. |
| 8,071,591 B2 | 12/2011 | Nomura et al. |
| 8,207,216 B2 | 6/2012 | Kozikowski et al. |
| 8,298,825 B1 | 10/2012 | Hochedlinger et al. |
| 8,377,886 B2 | 2/2013 | Susztak et al. |
| 8,575,122 B2 | 11/2013 | Lichter et al. |
| 8,686,042 B2 | 4/2014 | Gil et al. |
| 8,771,754 B2 | 7/2014 | Hallahan |
| 9,347,042 B2 | 5/2016 | Shimmura et al. |
| 10,041,046 B2 | 8/2018 | Karp et al. |
| 10,041,047 B2 | 8/2018 | Karp et al. |
| 10,568,883 B2 | 2/2020 | Karp et al. |
| 2003/0028905 A1 | 2/2003 | Knaus et al. |
| 2004/0006030 A1 | 1/2004 | Monia et al. |
| 2004/0015781 A1 | 1/2004 | Brown et al. |
| 2004/0038856 A2 | 2/2004 | Chakravarty et al. |
| 2004/0138188 A1 | 7/2004 | Higgins et al. |
| 2004/0147574 A1 | 7/2004 | Munchhof |
| 2004/0204431 A1 | 10/2004 | Scarborough et al. |
| 2005/0032835 A1 | 2/2005 | Pandey et al. |
| 2005/0227936 A1 | 10/2005 | McSwiggen et al. |
| 2005/0245508 A1 | 11/2005 | Weller et al. |
| 2005/0245520 A1 | 11/2005 | Dodic et al. |
| 2005/0287127 A1 | 12/2005 | Li et al. |
| 2005/0287128 A1 | 12/2005 | Guerciolini et al. |
| 2006/0003929 A1 | 1/2006 | Bier et al. |
| 2006/0229266 A1 | 10/2006 | Kumar et al. |
| 2007/0066632 A1 | 3/2007 | Hart et al. |
| 2007/0088080 A1 | 4/2007 | Gordillo et al. |
| 2007/0155722 A1 | 7/2007 | Li et al. |
| 2007/0167918 A1 | 7/2007 | Reed et al. |
| 2008/0015161 A1 | 1/2008 | Vornlocher et al. |
| 2008/0108656 A1 | 5/2008 | Pandey et al. |
| 2009/0036382 A1 | 2/2009 | Bressan et al. |
| 2009/0270497 A1 | 10/2009 | Buggy |
| 2010/0267141 A1 | 10/2010 | Shi et al. |
| 2010/0292205 A1 | 11/2010 | Lefker et al. |
| 2011/0135756 A1 | 6/2011 | Owens et al. |
| 2011/0166060 A1 | 7/2011 | Simons et al. |
| 2011/0305674 A1 | 12/2011 | Edge et al. |
| 2012/0059021 A1 | 3/2012 | Biechele et al. |
| 2012/0196312 A1 | 8/2012 | Sato et al. |
| 2013/0079329 A1 | 3/2013 | Hood et al. |
| 2013/0189327 A1* | 7/2013 | Ortega ............ C12N 5/0672 424/400 |
| 2013/0324594 A1 | 12/2013 | Guthrie |
| 2014/0243227 A1 | 8/2014 | Clevers et al. |
| 2014/0248696 A1 | 9/2014 | Zhang et al. |
| 2016/0194604 A1 | 7/2016 | Karp et al. |
| 2017/0071937 A1 | 3/2017 | Karp et al. |
| 2017/0226477 A1 | 8/2017 | Karp et al. |
| 2019/0017015 A1 | 1/2019 | Karp et al. |

FOREIGN PATENT DOCUMENTS

| | | |
|---|---|---|
| CN | 101341138 A | 1/2009 |
| CN | 103361300 A | 10/2013 |
| EP | 0945464 A1 | 9/1999 |
| EP | 1739087 A1 | 1/2007 |
| EP | 1961748 A2 | 8/2008 |
| EP | 2 636 731 A1 | 9/2013 |
| EP | 2765188 A1 | 8/2014 |
| WO | WO 96/40094 A1 | 12/1996 |
| WO | WO 98/19700 A1 | 5/1998 |
| WO | WO 99/58128 A1 | 11/1999 |
| WO | WO 00/12497 A2 | 3/2000 |
| WO | WO 00/31135 A1 | 6/2000 |
| WO | WO 00/59939 A1 | 10/2000 |
| WO | WO 01/85685 A1 | 11/2001 |
| WO | WO 02/094833 A1 | 11/2002 |
| WO | WO 03/037891 A1 | 5/2003 |
| WO | WO 03/097639 A1 | 11/2003 |
| WO | WO 2004/013135 A1 | 2/2004 |
| WO | WO 2004/021989 A2 | 3/2004 |
| WO | WO 2004/026307 A1 | 4/2004 |
| WO | WO 2004/026865 A1 | 4/2004 |
| WO | WO 2004/026871 A1 | 4/2004 |
| WO | WO 2004/067530 A1 | 8/2004 |
| WO | WO 2005/009939 A1 | 2/2005 |
| WO | WO 2005/039570 A1 | 5/2005 |
| WO | WO 2006/018633 A1 | 2/2006 |
| WO | WO 2006/018967 A1 | 2/2006 |
| WO | WO 2006/100490 A1 | 9/2006 |
| WO | WO 2007/018818 A1 | 2/2007 |
| WO | WO 2007/048857 A1 | 5/2007 |
| WO | WO 2007/102770 A1 | 9/2007 |
| WO | WO 2008/010852 A2 | 1/2008 |
| WO | WO 2008/076556 A2 | 6/2008 |
| WO | WO 2008/077138 A1 | 6/2008 |
| WO | WO 2009/017453 A1 | 2/2009 |
| WO | WO 2009/017455 A1 | 2/2009 |
| WO | WO 2009/032667 A1 | 3/2009 |
| WO | 2009/132050 A2 | 10/2009 |
| WO | WO 2010/060088 A2 | 5/2010 |
| WO | WO 2010/068955 A2 | 6/2010 |
| WO | WO 2010/075551 A1 | 7/2010 |
| WO | WO 2010/104205 A1 | 9/2010 |
| WO | WO 2011/019957 A1 | 2/2011 |
| WO | 2011/050476 A1 | 5/2011 |
| WO | WO 2011/079841 A1 | 7/2011 |
| WO | WO 2011/089416 A1 | 7/2011 |
| WO | WO 2011/116930 A1 | 9/2011 |
| WO | WO 2011/143511 A2 | 11/2011 |
| WO | WO 2012/103012 A1 | 8/2012 |
| WO | WO 2013/051722 A1 | 4/2013 |
| WO | WO 2013/124413 A1 | 8/2013 |
| WO | WO 2014/003098 A1 | 1/2014 |
| WO | WO 2014/013255 A1 | 1/2014 |
| WO | WO 2014/039908 A1 | 3/2014 |
| WO | WO 2014/050779 A1 | 4/2014 |
| WO | WO 2014/059383 A1 | 4/2014 |
| WO | WO 2014/083132 A1 | 6/2014 |
| WO | WO 2014/159356 A1 | 10/2014 |
| WO | WO 2015/168149 A2 | 11/2015 |
| WO | WO2015175783 * | 11/2015 |
| WO | WO 2016/037016 A1 | 3/2016 |

OTHER PUBLICATIONS

Associação Brasileira de Otorrinolaringologia e Cirurgia Cérvico-facial et al., "Sensorineural Hearing Loss: Radiologic Diagnosis," Revista da Associacao Medica Brasileira, vol. 58, pp. 519-529, 2012.

Barker, et al., "Lgr5$^{+ve}$ stem cells drive self-renewal in the stomach and build long-lived gastric units in vitro," Cell Stem Cell, vol. 6, 25-36, 2010.

Barker, N., et al., "Identification of stem cells in small intestine and colon by marker gene Lgr5," Nature, 449, No. 25: 1003-1007 (Oct. 2007).

Bermingham, et al., "Math 1: An Essential Gene for the Generation of Inner Ear Hair Cells," Science, 284:1837-1841 (Jun. 11, 1999).

Bohl, et al., "Development of a Specially Tailored Local Drug Delivery System for the Prevention of Fibrosis After Insertion of Cochlear Implants Into the Inner Ear," Journal of Materials Science Materials in Medicine, vol. 23:2151-2162 (2012).

Borenstein, J. T., "Intracochlear Drug Delivery Systems," Expert Opinion on Drug Delivery, vol. 8, No. 9, pp. 1161-1174, Sep. 2011, published online May 26, 2011.

Bramhall, N. F. et al., "Lgr5-Positive Supporting Cells Generate New Hair Cells in the Postnatal Cochlea", Stem Cell Reports, 2(3): 311-322 (2014).

Brigande, J.V. and Heller, S., "Quo vadis, hair cell regeneration?" Nat. Neurosci., 12(6): 679-685 (2009).

Buczacki, S.J., et al., "Intestinal label-retaining cells are secretory precursors expressing Lgr5," Nature, 495: 65-72 (2013).

Butler et al., "Rational Design and Simple Chemistry Yield a Superior, Neuroprotective HDAC Inhibitor, Tubastatin A," J. Am. Chem. Soc., vol. 132: 10842-10846 (2010).

(56) References Cited

OTHER PUBLICATIONS

Byfield, et al., "Lateral Signaling Enhances TGF-β Response Complexity," Trends Cell Biol., 14(3):107-111 (Mar. 2004).
Byfield, et al., "SB-505124 Is a Selective Inhibitor of Transforming Growth Factor-β Type I Receptors ALK4, ALK5, and ALK7," Molecular Pharmacology, vol. 65, No. 3, pp. 744-752, Mar. 2004.
Callahan, et al., "Identification of Novel Inhibitors of the Transforming Growth Factor Beta1 (TGF-beta1) Type 1 Receptor (ALK5)," J. Med. Chem., vol. 45., No. 5, pp. 999-1001, Feb. 28, 2002.
Chai, R., et al., "Dynamic Expression of Lgr5, a Wnt Target Gene, in the Developing and Mature Mouse Cochlea", J. Assoc. Res. Otolaryngology, 12(4): 455-469 (2011).
Chai, R., et al., "Wnt signaling induces proliferation of sensory precursors in the postnatal mouse cochlea", Proc. Nat'l Acad. Sci. USA, 109(21): 8167-8172 (2012).
Chen, et al., "Inner Ear Drug Delivery Via a Reciprocating Perfusion System in the Guinea Pig," Journal of Controlled Release : Official Journal of the Controlled Release Society, 110:1-19 (2005).
Chen, F-Q., et al., "Aminoglycoside-induced histone deacetylation and hair cell death in the mouse cochlea," J. Neurochem., 108(5): 1226-1236 (2009).
Chen, G. et al., "Preliminary Study on Brain-Targeted Drug Delivery Via Inner Ear," Yao xue xue bao = Acta pharmaceutica Sinica, 42:1102-1106 (2007). (Abstract Provided).
Cox, et al., "Spontaneous Hair Cell Regeneration in the Neonatal Mouse Cochlea in Vivo," Development, vol. 141, No. 4, pp. 816-829, Feb. 2014.
Crosnier, C., et al., "Organizing cell renewal in the intestine: stem cells, signals and combinatorial control.," Nature Reviews Genetics, 7: 349-359 (2006).
Dai, et al., "Human Serum and Glucocorticoid-Inducible Kinase-Like Kinase (SGKL) Phosphorylates Glycogen Syntheses Kinase 3 Beta (GSK-3beta) at Serine-9 Through Direct Interation," Biolchem. Biophys. Res. Commun., vol. 293, No. 4, pp. 1191-1196, May 17, 2002.
Davies, et al., "The Interaction Between β-Catenin, GSK3β and APC After Motogen Induced Cell-Cell Dissociation, and Their Involvement in Signal Transduction Pathways in Prostate Cancer," International Journal of Oncology, vol. 18, No. 4, pp. 843-847, Apr. 1, 2001.
Davis, et al, "Mesodermal Fate Decisions of a Stem Cell: the Wnt Switch," Cell Mol Life Sci., 65(17):2658-74 (2008) (abstract only).
Drottar, M., et al., "The Histone Deacetylase Inhibitor Sodium Butyrate Protects Against Cisplatin-Induced Hearing Loss in Guinea Pigs," Laryngoscope, 116(2): 292-296 (2006).
Dumont, et al., "Targeting the TGFβ Signaling Network in Human Neoplasia," Cancer Cell, vol. 3, No. 6, pp. 531-536, Jun. 2003.
Engleder, et al., "Preclinical Evaluation of Thermoreversible Triamcinolone Acetonide Hydrogels for Drug Delivery to the Inner Ear," International Journal of Pharmaceutics, vol. 471, No. 1-2, pp. 297-302, Aug. 25, 2014.
Espinoza, et al., "Phosphorylation by Glycogen Synthase Kinase-3β Down-Regulates Notch Activity, a Link for Notch and Wnt Pathways," Journal of Biological Chemistry, vol. 278, No. 34, pp. 32227-32235, Aug. 22, 2003.
Farin, H.F., et al., "Redundant sources of Wnt regulate intestinal stem cells and promote formation of Paneth cells," Gastroenterology, 143: 1518-1529 (2012).
Foltz, et al., "Glycogen Synthase Kinase-3β Modulates Notch Signaling and Stability," Current Biology, vol. 12, No. 12, pp. 1006-1011, Jun. 25, 2002.
Fu, et al., "SM16, an Orally Active TFG-β Type I Receptor Inhibitor Prevents Myofibroblast Induction and Vascular Fibrosis in the Rat Carotid Injury Model," Arteriosclerosis, Thrombosis and Vascular Biology, vol. 28, No. 4, pp. 665-671, Jan. 17, 2008.
Fujioka, et al., "Development of Auditory-Specific Brain Rhythm in Infants," European Journal of Neuroscience, 33:521-529 (Jan. 13, 2011).
Fuller, M.K., et al., "Intestinal crypts reproducibly expand in culture", J. Surg. Res., 178(1):48-54 (2012).

Gale, J. and Jagger, D., "Cochlear Supporting Cells," Chapter 11 in Oxford Handbook of Auditory Science: The Ear, 31 pages (2010).
Garcia-Berrocal Jr., et al., "Alternatives to Systemic Steroid Therapy for Refractory Immune-Mediated Inner Ear Disease: A Physiopathologic Approach," Eur. Arch. Otorhinolarynqol, vol. 263, No. 11, pp. 977-982, Nov. 2006.
Gellibert, et al., "Identification of 1, 5-Naphthyridine Derivatives as a Novel Series of Potent and Selective TGF-Beta Type 1 Receptor Inhibitors," J. Med. Chem., vol. 47, No. 18, pp. 4494-4506, Aug. 26, 2004.
Gupta, et al., "Fast-Gelling Injectable Blend of Hyaluronan and Methylcellulose for Intrathecal, Localized Delivery to the Injured Spinal Cord," Biomaterials, 27:2370-2379 (2006).
Haegebarth, et al., "Wnt Signaling, Lgr5, and Stem Cells in the Intestine and Skin," The American Jounral of Pathology, vol. 174, No. 3, pp. 715-721, Mar. 2009.
Haggarty, S.J., et al., "Domain-Selective Small-Molecule Inhibitor of Histone Deacetylase 6 (HDAC6)-Mediated Tubulin Deacetylation", Proc. Nat'l. Acad. Sci. USA, 100(8): 4389-4394 (2003).
Halder, et al., "A Specific Inhibitor of TGF-β Receptor Kinase, SB-431542, as a Potent Antitumor Agent for Human Cancers," Neoplasia, vol. 7, No. 5, pp. 509-521, May 2005.
Harding, G.W. et al, "The effect of an age-related hearing loss gene (Ahl) on noise-induced hearing loss and cochlear damage from low-frequency noise," *Hearing Research*, 204:90-100 (2005).
Herraiz, et al., "Intratympanic Drug Delivery for the Treatment of Inner Ear Diseases," Acta Otorrinolaringologica Espanola, 61(3):225-232 (2010).
Hong, et al., "Human Dynamin-Like Protein Interacts with the Glycogen Synthase Kinase 3β," Biochem. Biophys. Res. Commun., vol. 249, No. 3, pp. 697-703, Aug. 28, 1998.
Hoskison, et al., "Drug Delivery to the Ear," Therapeutic Delivery, 4(1):115-124 (Jan. 2013).
Huang, et al., "Directed, Efficient, and Versatile Modifications of the *Drosophila* Genome by Genomic Engineering," PNAS, vol. 106, No. 20, pp. 8284-9290, May 19, 2009.
Huang, et al., "RAD18 Transmits DNA Damage Signaling to Elicit Homologous Recombination Repair," Nat. Cell. Biol., vol. 11, No. 5, pp. 592-603, May 2009.
Huang, et al., "Systematic and Integrative Analysis of Large Gene Lists Using DAVID Bioinformatics Resources," Nature Protocols, 4(1):44-57 (2009) (pub. online, Dec. 18, 2008).
Isaacson, et al., "Differential Diagnosis and Treatment of Hearing Loss," American Family Physician, vol. 18, pp. 1125-1132, 2003.
Itoh et al., "False HDAC inhibition by aurone compound;" Chemical and Pharmaceutical Bulletin, vol. 64 (2016); pp. 1124-1128.
Izumikawa, et al., "Auditory Hair Cell Replacement and Hearing Improvement by Atoh1 Gene Therapy in Deaf Mammals," Nat Med., 11(3):271-276 (Mar. 2005).
Jeon, et al., "Notch Signaling Alters Sensory or Neuronal Cell Fate Specification of Inner Ear Stem Cells," Journal Neurosci, vol. 31, No. 23, pp. 8351-8358, Jun. 8, 2011.
Jung, P., et al., "Isolation and in vitro expansion of human colonic stem cells," Nat. Med., 17, 1225-1227 (2011).
Kanzaki, et al., "Novel in Vivo Imaging Analysis of an Inner Ear Drug Delivery System in Mice: Comparison of Inner Ear Drug Concentrations Over Time After Transtympanic and Systemic Injections," PloS One, vol. 7:e48480, 2012.
Kawamoto, Tadafumi, "Use of a New Adhesive Film for the Preparation of Multi-Purpose Fresh-Frozen Sections from Hard Tissues, Whole-Animals, Insects and Plants," Arch Histol Cytol, vol. 66, No. 2, pp. 123-143, Apr. 2003.
Kazanjian, A., et al., "Atonal homolog 1 is required for growth and differentiation effects of notch/gamma-secretase inhibitors on normal and cancerous intestinal epithelial cells," Gastroenterology, 139: 918-928 (2010).
Kim, et al., "Development of a Drug Delivery System for the Inner Ear Using Poly(amino acid)-Based Nanoparticles," Drug Delivery, 22(3):367-374 (2015).
Koch, et al., "Stem cells living with a Notch," The Company of Biologists Ltd, Development, vol. 140, pp. 689-704, 2013.

(56) References Cited

OTHER PUBLICATIONS

Kujawa, et al., "Conditioning-Related Protection from Acoustic Injury: Effects of Chronic Deefferentation and Sham Surgery," J. Neurophysiol., vol. 78, pp. 3095-3106 (1997).
Lajud, S.A., et al., "A Regulated Delivery System for Inner Ear Drug Application," Journal of Controlled Release : Official Journal of the Controlled Release Society, 166:268-276 (2013).
Lanford, et al., "Notch Signaling Pathway Mediates Hair Cell Development in Mammalian Cochlea," Nature Genetics, vol. 21, pp. 289-292, Mar. 1999.
Lasak, et al., "Hearing Loss: Diagnosis and Management," Primary Care, vol. 41, pp. 19-31, 2014.
Lehner, et al., "A Totally Implantable Drug Delivery System for Local Therapy of the Middle and Inner Ear," Ear, Nose, & Throat Journal, 76(8):567-570 (1997).
Li, et al., "A Novel Aerosol-Mediated Drug Delivery System for Inner Ear Therapy: Intratympanic Aerosol Methylprednisolone Can Attenuate Acoustic Trauma," IEEE Transactions on Bio-Medical Engineering, 60(9):2450-2460 (2013).
Li, et al., "Interaction of Glycogen Synthase Kinase 3β with the DF3/MUC1 Carcinoma-Associated Antigen and β-Catenin," Molecular and Cellular Biology, vol. 18, No. 12, pp. 7216-7224, Dec. 1998.
Li, et al., "Retinoic Acid Stimulates Chondrocyte Differentiation and Enhances Bone Morphogenetic Protein Effects through Induction of Smad1 and Smad5," Endocrinology, vol. 144, No. 6, pp. 2514-2523, Feb. 3, 2003.
Liu, et al. "Identification of Stage-Specific Markers During Differentiation of Hair Cells From Mouse Inner Ear Stem Cells or Progenitor Cells in Vitro," Int. J. Biochem. Cell. Biol., vol. 60, pp. 99-111, Mar. 2015.
Liu, et al., "In vivo Notch reactivation in differentiating cochlear hair cells induces Sox2 and Prox1 expression but does not disrupt hair cell maturation," Dev Dyn., vol. 241, pp. 684-696, Apr. 2012.
Lu, Z., et al., "The Influence of Glycogen Synthase Kinase 3 in Limiting Cell Addition in the Mammalian Ear," pp. 1059-1075, published online in Wiley InterScience (www.interscience.wiley.com) May 9, 2008.
Lukacs, R.U., et al., "Isolation, cultivation and characterization of adult murine prostate stem cells," Nat. Protoc., 5(4):702-713 (2010).
Lumpkin, et al., "Math1-Driven GFP Expression in the Developing Nervous System of Transgenic Mice," Gene Expr Patters, 3(4):389-395 (Aug. 2003).
Maison, et al., "Olivocochlear Innervation in the Mouse: Immunocytochemical Maps, Crossed Versus Uncrossed Contributions, and Transmitter Colocalization," J. Comp. Neurol., vol. 455, No. 3, pp. 406-416, Jan. 13, 2003.
Mak, et al., "The Tuberin-Hamartin Complex Negatively Regulates β-Catenin Signaling Activity," The Journal of Biological Chemistry, vol. 278, No. 8, 5947-5951, Feb. 2003.
Martinez-Monedero, et al., "Differentiation of Inner Ear Stem Cells to Functional Sensory Neurons," Developmental Neurobiology, vol. 68, No. 5, pp. 669-684, Apr. 2008.
McCall, et al., "Drug Delivery for Treatment of Inner Ear Disease: Current State of Knowledge," Ear and Hearing, vol. 31, No. 2, pp. 156-165, Apr. 2010.
Meng, et al., "Gamma-Secretase Inhibitors Abrogate Oxaliplatin-Induced Activation of the Notch-1 Signaling Pathway in Colon Cancer Cells Resulting in Enhanced Chemosensitivity," Cancer Research, vol. 69, pp. 573-582, 2009.
Mikulec, et al., "Permeability of the Round Window Membrane is Influenced by the Composition of Applied Drug Solutions and by Common Surgical Procedures," Otol. Neurotol. vol. 29, No. 7, pp. 1020-1026, Oct. 2008.
Mills, D. M., "Determining the Cause of Hearing Loss: Differential Diagnosis Using a Comparison of Audiometric and Otoacoustic Emission Responses," Ear and Hearing, 27(5):508-525 (2006).
Mimura, T. et al., "Topical Ocular Drug Delivery to Inner Ear Disease and Sinusitis," Southern Medical Journal, 99(11):1287-1289 (2006).
Mizutari, et al., "Notch Inhibition Induces Cochlear Hair Cell Regeneration and Recovery of Hearing after Acoustic Trauma," Neuron, vol. 77, No. 1, pp. 58-69, Jan. 2013.
Mizutari, et al., "Spontaneous Recovery of Cochlear Fibrocytes After Severe Degeneration Caused by Acute Energy Failure," Frontiers in Pharmacology, vol. 5, No. 198, pp. 1-3, Aug. 26, 2014.
Mundada, A.S. et al., "In Situ Gelling Polymers in Ocular Drug Delivery Systems: A Review," Critical Reviews in Therapeutic Drug Carrier Systems, 26(1):85-118 (2009). (Impact Factor—3.99).
Nakagawa, et al., "Local Drug Delivery to the Inner Ear Using Biodegradable Materials," Therapeutic Delivery, 2(6):807-814 (Jun. 2011).
Nakamura, et al., "Axin, An Inhibitor of the Wnt Signalling Pathway, Interacts with β-Catenin, GSK-3β and APC and Reduces the β-Catenin Level," Genes Cells, vol. 3, No. 6, pp. 395-403, Jun. 1998.
Olsauskas-Kuprys, et al., "Gamma Secretase Inhibitors of Notch Signaling," OncoTargets and Therapy, vol. 6, pp. 943-955, 2013.
Oshima, et al., "Phylogenetic Relationships Among Mycoplasmas Based on the Whole Genomic Information," J. Mol. Evol., 65(3):249-258 (Sep. 2007), (Epub Aug. 9, 2007).
Paasche, et al., "Technical Report: Modification of a Cochlear Implant Electrode for Drug Delivery to the Inner Ear," Otology & Neurotology, 24:222-227 (2003).
Pararas, et al., "Kinetics of Reciprocating Drug Delivery to the Inner Ear," Journal of Controlled Release : Official Journal of the Controlled Release Society, 152:270-277 (2011).
Pararas, et al., "Microsystems Technologies for Drug Delivery to the Inner Ear," Advanced Drug Delivery Reviews, 64:1650-1660 (2012).
Paulson, et al., "A Novel Controlled Local Drug Delivery System for Inner Ear Disease," Otology/Basic and Clinical Research; The Laryngoscope, vol. 118:706-711 (2008).
Peer, et al., "Nanocarriers as an Emerging Platform for Cancer Therapy," Nature Nanotechnology, 2:751-760 (2007).
Peterson, et al., "Oral Administration of GW788388, An Inhibitor of TGF-β Type I and II Receptor Kinases, Decreases Renal Fibrosis," Kidney International, vol. 73, pp. 705-715, (2008), published online Dec. 12, 2007.
Plontke, et al. "Randomized Double Blind, Placebo Controlled Trial on the Safety and Efficacy of Continuous Intratympanic Dexamethasone Delivered Via a Round Window Catheter for Severe to Profound Sudden Idiopathic Sensorineural Hearing Loss After Failure of Systemic Therapy," The Laryngoscope, 119:359-369 (2009).
Plontke, et al., "1D-and 3D-Computer Simulation for Experimental Planning and Interpretation of Pharmacokinetic Studies in the Inner Ear After Local Drug Delivery," Altex, vol. 21, Suppl 3, pp. 77-85, 2004.
Plontke, et al., "Cochlear Pharmacokinetics With Local Inner Ear Drug Delivery Using a Three-Dimensional Finite-Element Computer Model," Audiology & Neuro-Otology, vol. 12, pp. 37-48, 2007.
Plontke, et al., "Pharmacokinetic Considerations in Intratympanic Drug Delivery to the Inner Ear," Acta Oto-Rhino-Laryngologica Belgica, 56(4):369-370 (2002).
Plontke, et al., "Simulation of Application Strategies for Local Drug Delivery to the Inner Ear," ORL Journal for Oto-Rhino-Laryngology and Its Related Specialties, vol. 68, No. 6, pp. 386-392, Oct. 26, 2006.
Plontke, et al., "Technical Note on Microcatheter Implantation for Local Inner Ear Drug Delivery Surgical Technique and Safety Aspects," Otology & Neurotology, 27(7):912-917 (2006).
Plontke, et al., "Transtympanic Endoscopy for Drug Delivery to the Inner Ear Using a New Microendoscope," Advances in Oto-Rhino-Laryngology, 59:149-155 (2002).
Plontke, S. K., "Evaluation of the Round Window Niche Before Local Drug Delivery to the Inner Ear Using a New Mini-Otoscope," Otology & Neurotology, 32(1):183-185 (2011).
Pritz, et al., "Nanomedicine Strategies for Drug Delivery to the Ear," Nanomedicine, 8(7):1155-1172 (Jul. 2013).
Provenzano, M.J. and Domann, F.E., "A role for epigenetics in hearing: Establishment and maintenance of auditory specific gene expression patterns," Hearing Res., 233(1-2): 1-13 (2007).

(56) References Cited

OTHER PUBLICATIONS

Purow, B., "Notch Inhibition as a Promising New Approach to Cancer Therapy," Advances in Experimental Medicine and Biology, 727:305-319 (2012).
Raphael, Y., "Evidence for Supporting Cell Mitosis in Response to Acoustic Trauma in the Avian Inner Ear," Journal of Neurocytology, 21:663-671 (1992).
Richardson, et al., "Novel Drug Delivery Systems for Inner Ear Protection and Regeneration After Hearing Loss," Expert Opinion on Drug Delivery, 5(10):1059-1076 (Sep. 2008).
Rivera, et al., "Drug Delivery to the Inner Ear: Strategies and their Therapeutic Implications for Sensorineural Hearing Loss," Current Drug Delivery, 9(3):231-242 (May 2012).
Roy, et al., "Cell-Specific Targeting in the Mouse Inner Ear Using Nanoparticles Conjugated with a Neurotrophin-Derived Peptide Ligand: Potential Tool for Drug Delivery," International Journal of Pharmaceutics, 390:214-224 (2010).
Roy, et al., "Strategies for Drug Delivery to the Human Inner Ear by Multifunctional Nanoparticles," Nanomedicine, 7(1):55-63 (2012).
Ryals, et al., "Return of Function After Hair Cell Regeneration," Hearing Research, 297:113-120 (2013).
Sage, et al., "Essential role of retinoblastoma protein in mammalian hair cell development and hearing," Proc. Natl. Acad. Sci. USA, vol. 103, pp. 7345-7350, May 2006.
Sage, et al., "Proliferation of Functional Hair Cells in Vivo in the Absence of the Retinoblastoma Protein," Science, vol. 307, pp. 1114-1118, Feb. 18, 2005.
Sakamoto, T. et al., "Inner Ear Drug Delivery System from the Clinical Point of View," Acta Oto-Laryngologica, 130:sup563:101-104 (2010).
Salt, A., "Dexamethasone Concentration Gradients Along Scala Tympani After Application to the Round Window Membrane," Otology & Neurotology, 29(3):401-406 (2008).
Salt, A., "Guest Editorial: Drug Delivery for Treatment of Inner Ear Disease: Current State of Knowledge," Ear and Hearing, vol. 31, p. 155 (2010).
Salt, et al., "Dependence of Hearing Changes on the Dose of Intratympanically Applied Gentamicin: A Meta-Analysis Using Mathematical Simulations of Clinical Drug Delivery Protocols," The Laryngoscope, 118(10):1793-1800 (Oct. 2008).
Salt, et al., "Distribution of Dexamethasone and Preservation of Inner Ear Function Following Intratympanic Delivery of a Gel-Based Formulation," Audiology & Neuro-otology, vol. 16, pp. 323-335, 2011.
Salt, et al., "Local Inner Ear Drug Delivery and Pharmacokinetics," Drug. Discov. Today, vol. 10, No. 19, pp. 1299-1306, Oct. 1, 2005.
Salt, et al., "Principles of Local Drug Delivery to the Inner Ear," Audiol. Neurotol. vol. 14, No. 6, pp. 350-360, Nov. 16, 2009.
Salvi, et al., "Hair Cell Regeneration, Repair, and Protection," Springer Handbook of Auditory Research, vols. 1-33, 323 pages, 2008.
Sataloff, R. T. et al., "Differential Diagnosis of Occupational Hearing Loss," Occupational Health & Safety, 70(9):126-129 (Sep. 2001).
Sato, T., et al., "Long-term expansion of epithelial organoids from human colon, adenoma, adenocarcinoma, and Barrett's epithelium," Gastroenterology, 141: 1762-1772 (2011).
Sato, T., et al., "Paneth cells constitute the niche for Lgr5 stem cells in intestinal crypts," Nature, 469: 415-418 (2011).
Sawyer, et al., "Synthesis and Activity of New Aryl- and Heteroaryl-Substituted 5, 6-Dihiydro-4H-Pyrrolo[1,2-b]Pyrazole Inhibitors of the Transforming Growth Factor-Beta Type I Receptor Kinase Domain," Bioorg. Med. Chem. Lett, vol. 14, No. 13, pp. 3581-3584, Jul. 5, 2004.
Sawyer, et al., "Synthesis and Activity of New Aryl- and Heteroaryl-Substituted Pyrazole Inhibitors of the Transforming Growth Factor-Beta Type 1 Receptor Kinase Domain," J. Med. Chem., vol. 46, No. 19, pp. 3953-3956, Sep. 11, 2003.
Schwarz-Romond, et al., "The Ankyrin Repeat Protein Diversin Recruits Casein Kinase Iε to the β-Catenin Degradation Complex and Acts in Both Canonical Wnt and Wnt/JNK Signaling," Genes, Dev., vol. 16, No. 16, pp. 2073-2084, Jun. 2002.
Scoville, et al., "Current view: intestinal stem cells and signaling," Gastroenterology, 134(3): 849-864 (2008).
Seidman, M. D., "Glutamate Antagonists, Steroids, and Antioxidants as Therapeutic Options for Hearing Loss and Tinnitus and the Use of an Inner Ear Drug Delivery System," The International Tinnitus Journal, vol. 4, pp. 148-154, 1998.
Sekine, A., et al., "Hath1 Up-Regulates Gastric Mucin Gene Expression in Gastric Cells", Biochem. Biophys. Res. Commun., 344(4): 1166-71 (2006).
Shariatmadari, M., et al., "Increased Wnt Levels in the Neural Tube Impair the Function of Adherens Junctions During Neurulation," Mol Cell Neurosci., 30(3): 437-51. Epub (2005) (abstract only).
Shi, et al., "Beta-Catenin Up-Regulates Atoh1 Expression in Neural Progenitor Cells by Interaction with an Atoh1 3' Enhancer," The Journal of Biological Chemistry, vol. 285, pp. 392-400, 2010.
Shi, et al., "Generation of Hair Cells in Neonatal Mice by β-Catenin Overexpression in Lgr5-Positive Cochlear Progenitors," Proc Natl Acad Sci USA, vol. 110, No. 34, pp. 13851-13856, Aug. 20, 2013.
Shi, F., et al. "Wnt-Responsive Lgr5-Expressing Stem Cells Are Hair Cell Progenitors in the Cochlea", J. Neuroscience, 32 (28): 9639-9648 (2012).
Shih, et al., "Notch Signaling, Gamma-Secretase Inhibitors, and Cancer Therapy," Cancer Research, vol. 67, pp. 1879-1882, 2007.
Shoichet, M.S. et al., "Intrathecal Drug Delivery Strategy is Safe and Efficacious for Localized Delivery to the Spinal Cord," Progress in Brain Research, 161:385-392 (2007).
Snippert, H. J., et al., "Intestinal crypt homeostasis results from neutral competition between symmetrically dividing Lgr5 stem cells," Cell, 143: 134-144 (2010).
Staecker, et al., "Developments in Delivery of Medications for Inner Ear Disease," Expert Opinion on Drug Delivery, 10(5):639-650 (2013).
Staecker, et al., "Drug Delivery to the Inner Ear Using Gene Therapy," Otolaryngologic Clinics of North America, vol. 37, pp. 1091-1108, 2004.
Surovtseva, et al., "Prestin Binding Peptides as Ligands for Targeted Polymersome Mediated Drug Delivery to Outer Hair Cells in the Inner Ear," International Journal of Pharmaceutics, 424:121-127 (2012).
Swan, et al., "Inner Ear Drug Delivery for Auditory Applications," Adv. Drug. Deliv. Rev., vol. 60, No. 15, pp. 1583-1599, Dec. 14, 2008.
Tojo, et al., "The ALK-5 Inhibitor A-83-01 Inhibits Smad Signaling and Epithelial-to-Mesenchymal Transition by Transforming Growth Factor-β," Cancer Sci., vol. 96, No. 11, pp. 791-800, Nov. 2005.
Valdimarsdottir, et al., "Functions of the TGFβ Superfamily in Human Embryonic StempCells,"APMIS, vol. 113, pp. 773-389, Nov.-Dec. 2005.
Van der Flier, L.G., and Clevers, H., "Stem cells, self-renewal, and differentiation in the intestinal epithelium," Annual Review of Physiology, 71: 241-260 (2009).
Van Es, J.H., et al., "Intestinal stem cells lacking the Math1 tumour suppressor are refractory to Notch inhibitors", Nat. Commun., 1(18): 1-5 (2010).
Van Es, J.H., et al., "Notch/gamma-secretase inhibition turns proliferative cells in intestinal crypts and adenomas into goblet cells," Nature, 435: 959-963 (2005).
Van Tomme, S.R. et al., "In Situ Gelling Hydrogels for Pharmaceutical and Biomedical Applications," Int. J. Pharm., 355(1-2):1-18 (2008).
VanDussen, K.L., et al., "Notch signaling modulates proliferation and differentiation of intestinal crypt base columnar stem cells," Development, 139: 488-497 (2012).
Von Kries, et al., "Hot Spots in Beta-Catenin for Interactions with LEF-1, Conductin and APC," Nat. Struct. Biol., vol. 7, No. 9, pp. 800-807, Sep. 2000.
Voytik-Harbin, S.L, et al., "Small Intestinal Submucosa: A Tissue-Derived Extracellular Matrix That Promotes Tissue-Specific Growth and Differentiation of Cells in Vitro", Tissue Engineering, 4(2): 157-174 (1998).

(56) References Cited

OTHER PUBLICATIONS

Wang, et al., "Suppression of Androgen Receptor-Mediated Transactivation and Cell Growth by the Glycogen Synthase Kinase 3β in Prostate Cells," Journal of Biological Chemistry, vol. 279, No. 31, pp. 32444-32452, Jul. 30, 2004.

Wang, Y. et al., "Dynamics of Noise-Induced Cellular Injury and Repair in the Mouse Cochlea," J. of the Assoc. of Research in Otolaryngology, 3:248-268 (2002).

Warchol, et al., "Regenerative Proliferation in Organ Cultures of the Avian Cochlea: Identification of the Initial Progenitors and Determination of the Latency of the Proliferative Response," The Journal of Neuroscience : the Official Journal of the Society for Neuroscience, vol. 16, pp. 5466-5477, 1996.

White, et al., "Mammalian Cochlear Supporting Cells Can Divide and Trans-Differentiate Into Hair Cells," Nature, vol. 441, No. 7096, pp. 984-987, Jun. 22, 2006.

Wise, A.K. et al, "Drug Delivery to the Inner Ear," Journal of Neural Engineering, 9(6):065002, 10 pages (Nov. 2012).

Wong, et al., "Mechanisms of sensorineural cell damage, death and survival in the cochlea," Frontiers in Aging Neuroscience, vol. 7, Article 58, pp. 1-15, Apr. 2015.

Wu, et al., "Modulation of Notch Signaling by Mastermind-Like (MAML) Transcriptional Co-Activators and Their Involvement in Tumorigenesis," Seminars in Cancer Biology, 14:348-356 (2004).

Yang, J. et al, "Ectopic Hair Cell-Like Cell Induction by Math1 Mainly Involves Direct Transdifferentiation in Neonatal Mammalian Cochlea," Neuroscience Letters, 549:7-11 (2013).

Yang, J. et al, "Functional Features of Trans-Differentiated Hair Cells Mediated by Atoh1 Reveals a Primordial Mechanism," J. of Neuroscience, 32(11):3712-3725 (Mar. 2012).

Yao, M., et al., "Prostate-regenerating capacity of cultured human adult prostate epithelial cells," Cells Tissues Organs, 191: 203-212 (2010).

Yilmaz, O.H., et al., "mTORC1 in the Paneth cell niche couples intestinal stem-cell function to calorie intake," Nature, 486: 490-495 (2012).

Yin, et al., "Niche-Independent High-Purity Cultures of Lgr5+ Intestinal Stem Cells and Their Progeny," Nat. Methods, vol. 11, No. 1, pp. 106-112, Jan. 2014.

Ying, Q.L., et al., "The ground state of embryonic stem cell self-renewal," Nature, 453: 519-523 (2008).

Yingling, et al., "Development of TGF-β Signalling Inhibitors for Cancer Therapy," Nature Reviews Drug Discovery, vol. 3, No. 12, pp. 1011-1022, Dec. 2004.

Yu, et al., "In vivo proliferation of postmitotic cochlear supporting cells by acute ablation of the retinoblastoma protein in neonatal mice," J Neurosci, vol. 30, pp. 5927-5936, Apr. 2010.

Yuge, I., et al., "Transplanted Human Amniotic Epithelial Cells Express Connexin 26 and Na—K-Adenosine Triphophatase in the Inner Ear," Transplantation, vol. 77, No. 9, pp. 1452-1454, 2004.

Yui, S., et al., "Functional engraftment of colon epithelium expanded in vitro from a single adult Lgr5+ stem cell," Nature Medicine, 18(4): 618-623 (2012).

Zahnert, T., "The Differential Diagnosis of Hearing Loss," Deutsches Arzteblatt International, vol. 108, pp. 433-443, quiz 44, 2011.

Zhang, F., et al., "Inhibitory Phosphorylation of Glycogen Synthase Kinase-3 (GSK-3) in Response to Lithium," J. Bio. Chem., 278(3): 33067-33077 (2003).

Zheng, et al., "Overexpresson of Math1 Induces Robust Production of Extra Hair Cells in Postnatal Rat Inner Ears," Nature Neuroscience, 3(6):580-586 (Jun. 2000).

International Search Report and Written Opinion, issued in International Application No. PCT/US2017/012631, entitled "Production of Differentiated Enteroendocrine Cells and Insulin Producing Cells" filed Jan. 6, 2017; dated Apr. 18, 2017.

International Preliminary Report on Patentability for Int'l Application No. PCT/US2017/012631, titled "Production of Differentiated Enteroendocrine Cells and Insulin Producing Cells"; dated Jul. 10, 2018.

De Los Angeles, et al., "A chemical logic for reprogramming to pluripotency," Cell Research, vol. 23, No. 12, Dec. 2013, pp. 1337-1338.

Lin et al., "Inhibition of Notch Activity Promotes Nonmitotic Regeneration of Flair Cells in the Adult Mouse Utricles," The Journal of Neurosciencce, vol. 31, No. 43, Oct. 26, 2011, pp. 15329-15339.

* cited by examiner

PRODUCTION OF DIFFERENTIATED ENTEROENDOCRINE CELLS AND INSULIN PRODUCING CELLS

RELATED APPLICATIONS

This application claims the benefit of U.S. Provisional Application No. 62/276,814, filed on Jan. 8, 2016. The entire teachings of the above application are incorporated herein by reference.

GOVERNMENT SUPPORT

This invention was made with Government support under Grant No. R01 DE013023 awarded by the National Institutes of Health. The Government has certain rights in the invention.

BACKGROUND

The enteroendocrine system orchestrates how the body responds to nutrients by employing a diversity of hormones to fine-tune a wide range of physiological responses in the body, thus playing an important role in digestive and metabolic diseases such as Gastrointestinal (GI) disorders, diabetes and obesity. Enteroendocrine cells (EECs) form the largest endocrine system in the body (Grible and Reimann, 2015). EECs are individually dispersed along the crypt-villus axis throughout the intestinal epithelial but only exist in a small percentage (~1%) in vivo (Gunawardene et al., 2011). A key function of EECs is to sense luminal contents, particularly nutrients, and to respond by the secretion of a diversity of hormones (e.g. GLP-1) which modulate food intake, energy homeostasis and glucose tolerance (Furness, 2013). It is also suggested that EECs play a key role in gastric bypass surgery by secreting hormones such as GLP-1, PYY and GLP-2 (Mumphrey, 2013). Accordingly, EECs are a therapeutic target in diabetes and obesity. Furthermore, mounting evidence demonstrates an immunoregulatory function of EECs in innate immunity (Moran, 2008). EECs express functional Toll-like receptors (TLR) and directly respond to metabolites produced by commensal bacteria (Bogunovic, 2007). Recent evidence also suggests that EECs may directly orchestrate immune cell function through alteration in number and hormone secretion during inflammation (Worthington, 2015). EECs are also believed to play a critical role in metabolic diseases (e.g. diabetes and obesity), and gastrointestinal pathologies such as irritable Bowel syndrome, infectious enteritis and inflammatory bowel disease (Moran, 2008 and Manocha and Kahn, 2012). Thus, there is great interest in EECs for the exploration and development of disease interventions.

However, the study of enteroendocrine cells has been hindered by the relative lack of ability to culture EECs in vitro, as well as by the dispersed distribution of EEC and relative scarcity (1%) of EECs in intestinal epithelium. In particular, the knowledge of signals that control the differentiation and function of EEC are largely unknown. Furthermore, direct in vitro study of EECs has not been possible, because they are terminally differentiated cells that do not divide. Thus, due to the dispersed distribution and scarcity (1%) of EECs in the gut epithelium, it has been difficult to study the function and regulation of EECs in situ (Sternini, Anselmi and Rosengut, 2008 and Gunawerdene, Corfe and Staton, 2011).

Accordingly, there remains a need for in vitro EEC culture to allow for investigation of metabolic and digestive diseases. There is also a need for the ability to modulate the function of EECs and obtain specific EEC sub-types, such as for use in the discovery and implementation of the treatment of disease states.

SUMMARY OF THE INVENTION

Aspects of the disclosure include obtaining a population of enteroendocrine cells (EECs) from a mammalian post-natal cell population, such as a post-natal stem cell population, by treating the population with a plurality of small molecules that upregulate ChgA and promote differentiation of the cells to form the enteroendocrine cells. The upregulation of ChgA is such that the fraction of cells expressing CGA in the obtained cell population, as measured by a ChgA Immunostaining Assay, is at least about 1.5%. Small molecules that can be used to differentiate the post-natal stem cells into the enteroendocrine cells can include at least one of a Wnt activator, a Notch inhibitor, a Wnt inhibitor, a MEK/ERK inhibitor, a growth factor, a HDAC inhibitor, a Histone Methylation Inhibitor, a Tgf-β inhibitor, and a NeuroD1 activator.

Aspects of the disclosure also include a method for increasing the insulin expression of a population of mammalian cells by treating the population with a plurality of small molecules that induce the cells to increase the insulin expression. The insulin expression level may be increased in the cell population such that, in an Insulin Activity Assay using an Insulin-GFP reporter, the fraction of cells having the Insulin GFP reporter activated is at least about 1%. The mammalian cells that can be treated to increase the insulin expression can include post-natal cells or enteroendocrine cells, such as post-natal stem cells, post-natal multipotent progeny cells, and enteroendocrine cells. Small molecules that can be used for the treatment to increase the expression of insulin in the cells can include a DNA methylation inhibitor, a Tgf-β inhibitor, and a NeuroD1 activator.

Methods and/or compositions for treating disease states with the EECs and/or insulin producing cells described herein are also included according to an aspect of the disclosure. Also, populations of cells corresponding to the obtained EEC S and/or insulin producing cells are also included according to an aspect of the disclosure, as are kits containing the small molecules for use in preparing the EEC and/or insulin producing cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 39A. mRNA expression of Gip, Gcg, Cck for cells differentiated in multiple conditions, with or without the addition of Tubastatin A (Tu) in step 1. FIG. 39B. mRNA expression of Gip, Gcg and Cck for cells differentiation in multiple conditions with or without Tranylcypromine (Tc) added in Step 1, Step 2 or both steps. FIG. 39C. Dose dependent induction of EEC markers (ChgA, Gcg, Gip, Tph1) for Tranylcypromine. FIG. 39D. mRNA expression of multiple EEC markers (Gip, Gcg, Cck) for cells differentiated in multiple conditions. FIG. 39E. mRNA expression of Lyz1 for cells differentiated in multiple conditions.

FIG. 40A. mRNA expression of markers for goblet cell (Muc2), Paneth cell (Lyz1) and EECs (ChgA, Gcg, Gip, Cck, Tph1, Sst, Sct, and Pyy) with or without the addition of Wnt pathway inhibitor Wnt-C59 (C59) and Tgf-β pathway inhibitor Repsox (Rep) at multiple time points. S1, S2 represent Step 1 and Step 2 of 2-step differentiation protocol. 0 h or 12 h indicates the time points of adding C59. ENR was used as control for spontaneous differentiation. FIG. 40B. Time-course study of multiple genes in 2-step differentiation process. FIG. 40C. expression level of multiple genes comparing with their corresponding peak levels (Sox9, Math1, Ngn3, and NeuroD1 at day 2, ChgA at day 5, see FIG. 40D). FIG. 40E. Immunostaining of differentiated EEC cells.

FIG. 41A. mRNA expression of multiple genes in conditions with or without Repsox. Basal condition used was ENR.D. Tu. Tc-D.Pd. Tc. C59. Repsox was added in Step 2. FIG. 41B. mRNA expression of multiple genes in conditions as indicated. FIG. 41C. Morphology of differentiated cell colonies. Arrows indicate dead cells expelled from the colonies.

DEFINITIONS

Figure 1:
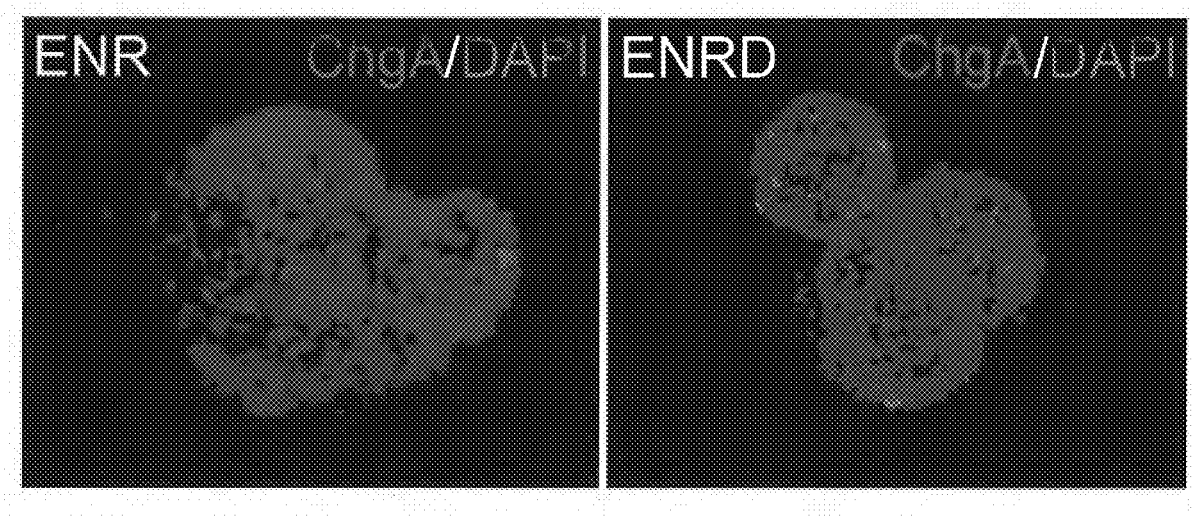
FIG. 1 shows an increase in differentiation of enteroendocrine cells (EEC) from ISCs using a Notch inhibitor.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" refers to introducing a substance into a subject. In some embodiments, administration is oral, or by injection. In certain embodiments "causing to be administered" refers to administration of a second component after a first component has already been administered (e.g., at a different time and/or by a different actor).

An "antibody" refers to an immunoglobulin polypeptide, or fragment thereof, having immunogen binding ability.

As used herein, an "agonist" is an agent that causes an increase in the expression or activity of a target gene, protein, or a pathway, respectively. Therefore, an agonist can bind to and activate its cognate receptor in some fashion, which directly or indirectly brings about this physiological effect on the target gene or protein. An agonist can also increase the activity of a pathway through modulating the activity of pathway components, for example, through inhibiting the activity of negative regulators of a pathway. Therefore, a "Wnt agonist" can be defined as an agent that increases the activity of Wnt pathway, which can be measured by increased TCF/LEF-mediated transcription in a cell. Therefore, a "Wnt agonist" can be a true Wnt agonist that bind and activate a Frizzled receptor family member, including any and all of the Wnt family proteins, an inhibitor of intracellular beta-catenin degradation, and activators of TCF/LEF. A "Notch agonist" can be defined as an agent that increase the activity of Notch pathway, which can be determined by measuring the transcriptional activity of Notch.

An "antagonist" refers to an agent that binds to a receptor, and which in turn decreases or eliminates binding by other molecules.

"Cell Density" as used herein in connection with a specific cell type is the mean number of that cell type per area in a Representative Microscopy Sample. The cell types may include but are not limited to $Lgr5^+$ cells, enteroendocrine cells, or insulin producing cells. The Cell Density may be assessed with a given cell type in a given sample, organ or tissue.

"Cell Differentiation" refers to the process by which a cell becomes specialized to perform a specific function, such as in the conversion of post-natal stem cells into cells having a more specialized function. In an embodiment, Lgr5+ intestinal stem cells are differentiated into enteroendocrine cells.

"ChgA Immunostaining Assay" as used herein is an assay used to determine the fraction of cells in a cell population that express ChgA by an immunostaining method. In an example of a ChgA immunostaining assay, a cell culture medium in which a cell population has been treated is removed, and the sample is washed with PBS. Organoids or cell colonies cultured in Matrigel are fixed directly by adding 4% PFA and incubating for 20 mins at room temperature. The Matrigel is then mechanically disrupted, and the cells are transferred to BSA-coated Eppendorf tubes. Samples are washed with PBS, permeabilized with 0.25% Triton X-100 for 30 minutes, and stained with primary antibody against Chromogranin A (e.g. anti-chromogranin A, sc-13090, Santa Cruz) and appropriate secondary antibodies (e.g. Alexa Fluor conjugated secondary antibodies, such as Alexa Fluor 594 conjugated Donkey anti-Rabbit antibody, A-21207; Life Technologies). Images are acquired by confocal microscopy.

"CHIR99021" is a chemical composition having the chemical formula $C_{22}H_{18}Cl_2N_8$ and the following alternate names: CT 99021; 6-[[2-[[4-(2,4-dichlorophenyl)-5-(5-methyl-1H-imidazol-2-yl)-2-pyrimidinyl]amino]ethyl]amino]-3-pyridinecarbonitrile. Its chemical structure is as follows:

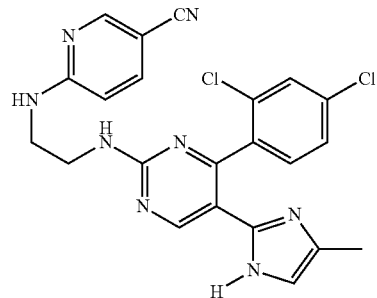 [SMILES: Cc1c[nH]c(-c2cnc(NCCNc3ccc(C#N)cn3)nc2-c2ccc(Cl)cc2Cl)n1]

"Complementary nucleic acid sequence" refers to a nucleic acid sequence capable of hybridizing with another nucleic acid sequence comprised of complementary nucleotide base pairs.

"Cross-Sectional Cell Density" as used herein in connection with a specific cell type is the mean number of that cell type per area of cross section through a tissue in a Representative Microscopy Sample.

"Decreasing" and "decreases" refer to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of reference, and includes decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a reference.

"EGFR inhibitor" is substance that inhibits the epidermal growth factor receptor. Examples of EGFR inhibitors include Erlotinib HCl (OSI-744), Gefitinib (ZD1839), Lapatinib (GW-572016) Ditosylate, Afatinib (BIBW2992), Neratinib (HKI-272), Canertinib (CI-1033), Lapatinib, AG-490 (Tyrphostin B42), CP-724714, Dacomitinib (PF299804, PF299), WZ4002, AZD8931 (Sapitinib), CUDC-101, AG-1478 (Tyrphostin AG-1478), PD153035 HCl, Pelitinib (EKB-569), AC480 (BMS-599626), AEE788 (NVP-AEE788), OSI-420, WZ3146 WZ8040, AST-1306, Rociletinib (CO-1686, AVL-301), Genistein, Varlitinib, Icotinib, TAK-285, WHI-P154, PD168393, CNX-2006, Tyrphostin 9, AG-18, Poziotinib (HM781-36B), AZD3759, Osimertinib (AZD9291), Afatinib (BIBW2992) Dimaleate, Erlotinib, Olmutinib (HM61713, BI 1482694), CL-387785 (EKI-785), NSC228155, AZ5104, AG490, AG 494, AG 555, AG 556, AG 825, AG 879, AG 99, AP 24534, AV 412, BIBU 1361, BMX 1382, BMS 599626, Canertinib, CGP 52411, GW 583340, HDS 029, HKI 357, Iressa, JNJ 28871063, Lavendustin A, Methyl 2,5-dihydroxycinnamate, PD 158780, PF 6274484, PKI 166, R 1530, RAF 265, and XL 184, among others.

"Eliminate" means to decrease to a level that is undetectable.

"Enteroendocrine cells" refers to cells that are specialized endocrine cells of the gastrointestinal tract and pancreas, and can be found in the intestinal tract, stomach and pancreas. The enteroendocrine cells form the largest endocrine system in the body, and can sense luminal contents, particularly nutrients, and respond by the secretion of a diversity of hormones (e.g. GLP-1) which modulate food intake, energy homeostasis and glucose tolerance. Specific types of enteroendocrine cell are often classified according to the expression of hormones within the specific enteroendocrine cell subset, such as cells that express GLP-1, 5HT, SST, gastrin, CCK, SCT, NTS, PYY, Gastrin and Ghrelin, among others. The different subsets of enteroendocrine have also been sometimes referred to as K cells, I cells, L cells, G cells, Enterochromaffin cells, N cells and S cells, but increasingly the hormone expression of the cells is used to identify the cell subtypes, as set forth above. Enteroendocrine cells can be identified by expression of ChgA marker, which can be detected by assays such as the mRNA ChgA Expression Assay and ChgA Immunostaining Assay described herein.

"Engraft" or "engraftment" refers to the process of stem or progenitor cell incorporation into a tissue of interest in vivo through contact with existing cells of the tissue.

"Epithelial progenitor cell" refers to a multipotent cell which has the potential to become restricted to cell lineages resulting in epithelial cells.

"Epithelial stem cell" refers to a multipotent cell which has the potential to become committed to multiple cell lineages, including cell lineages resulting in epithelial cells.

"Fragment" refers to a portion, e.g., of a polypeptide or nucleic acid molecule. This portion contains, for example, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Growth factor" refers to a substance capable of stimulating cellular growth, proliferation or differentiation.

"GSK3beta," "GSK3β," and "GSK3B" as used interchangeably herein are acronyms for glycogen synthase kinase 3 beta.

"GSK3beta inhibitor" is a substance that inhibits the activity of GSK3beta.

"HDAC" as used herein is an acronym for histone deacetylase.

"HDAC inhibitor" is a substance that inhibits the activity of HDAC.

"Histone Methylation Inhibitor" is a substance that inhibits histone methylation.

"Hybridize" refers to pairing to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

An "inhibitor" refers to an agent that causes a decrease in the expression or activity, e.g., of a target gene, a protein, or a pathway. For example, an "Wnt inhibitor" refers an agent that causes a decrease in the activity of Wnt signaling pathway, which can be for example a Wnt receptor inhibitor, a Wnt receptor antagonist, a Porcupine inhibitor which inhibits Wnt secretion, or a Tankyrase inhibitor, or a drug that interferes with β-catenin interactions. An "antagonist" can be an inhibitor, but is more specifically an agent that binds to a receptor, and which in turn decreases or eliminates binding by other molecules.

"Increasing" and "increases" refer to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, for example, as compared to the level of a reference, and includes increases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a as compared to the level of a reference standard.

"Insulin Activity Assay" as used herein is an assay used to determine the extent to which insulin gene transcription, translation or insulin release has been activated in a cell population. In an exemplary Insulin Activity Assay, the initial cells are isolated from the intestine of an Insulin-GFP mouse such as B6.Cg-Tg (Ins1-EGFP)1Haraa mouse (also referred to as the MIT-GFP mouse, Jackson lab stock no.: 006864). Intestinal crypts are isolated from the proximal half of the intestine. Approximately 200 crypts are entrapped in 40 µl of Matrigel and cultured in 24-well plates with 500 µl of crypt culture media (Advanced DMEM/F12 with media Supplements (1×N2, 1×B27, 2 mM Glutamax, 10 mM HEPES, 1 mM N-acetylcysteine, and 100 U/ml Penicillin/100 µg/ml Streptomycin)), and supplemented with growth factors (50 ng/ml EGF, 100 ng/ml Noggin, and 500 ng/ml R-Spondin1) and small molecules (5 µM CHIR99021 and 1.25 mM VPA) to obtain an enriched population of intestinal stem cells. The cells are then passaged for 1-2 times to create a starting cell population for the assay. To test the capacity of agents to activate insulin gene transcription, translation or insulin release, the cells are incubated with appropriate culture media (e.g. aforementioned crypt culture media), growth factors and/or other agents being tested. Appropriate culture media, including crypt culture media as well as the agents being assessed, are added into each well and incubated with the cells for a period of 2-10 days with media change every 2 days. The fraction of insulin-GFP positive cells (i.e., cells in which the insulin-GFP reporter is activated) can be quantified using a flow cytometer to measure the fraction of GFP+ cell population present in the total cell population. Also, the average insulin activity of a cell population can be measured by measuring the average mRNA expression level of insulin of the population normalized using suitable references or housekeeping genes (e.g., using mRNA expression of Hprt as a baseline).

"Intestinal stem cell" refers to a multipotent cell of intestinal lineage which has the potential to become committed to multiple cell lineages, including cell lineages resulting in intestinal cells such as enteroendocrine cells, enterocyte cells, goblet cells and paneth cells.

"Isolated" refers to a material that is free to varying degrees from components which normally accompany it as found in its native state. "Isolate" denotes a degree of separation from original source or surroundings.

"Lgr5" is an acronym for the Leucine-rich repeat-containing G-protein coupled receptor 5, also known as G-protein coupled receptor 49 (GPR49) or G-protein coupled receptor 67 (GPR67). It is a protein that in humans is encoded by the Lgr5 gene.

"Lgr5+ cell" or "Lgr5-positive cell" as used herein is a cell that expresses Lgr5. "Lgr5− cell" as used herein is a cell that is not Lgr5+.

"Mammal" refers to any mammal including but not limited to human, mouse, rat, sheep, monkey, goat, rabbit, hamster, horse, cow or pig.

"Multipotent progeny cell" refers to refers to a cell that is already more specific than a stem cell, meaning it has the tendency to differentiate into a specific type of cell, but still retains the ability to differentiate into multiple different but limited cell types. The multipotent progeny cell may be a multipotent cell that has been differentiated from a stem cell but has not yet differentiated into a "target" cell type.

"MEK/ERK inhibitor" is a substance that inhibits the MEK/ERK signaling pathway. Examples of MEK inhibitors include Arctigenin, BIX 02189, 10Z-Hymenialdisine, PD 0325901, PD 184352, PD 198306, PD 334581, PD 98059, SL 327, U0126, Selumetinib (AZD6244), Trametinib (GSK1120212), PD184352 (CI-1040), PD98059, Pimasertib (AS-703026), BIX 02188, TAK-733, AZD8330, Binimetinib (MEK162, ARRY-162, ARRY-438162), PD318088, Refametinib (RDEA119, Bay 86-9766), BI-847325, Cobimetinib (GDC-0973, RG7420), GDC-0623, and APS-2-79. Examples of ERK inhibitors include SCH772984, DEL-22379, VX-11e, ERK5-IN-1, XMD8-92, SC1 (Pluripotin), Ulixertinib (BVD-523, VRT75227, FR 180204, GDC-0994, BIX 02189, TCS ERK 11e, TMCB, and Eicosapentaenoic Acid.

"mRNA ChgA Expression Assay" refers to an assay used to determine the relative ChgA mRNA expression level in a cell population. For example, the assay can determine ChgA mRNA expression level of a differentiated cell population following treatment with agents being tested, as compared to an untested population of post-natal stem cells. In an example of an mRNA ChgA Expression Assay, the cells were collected and the RNA is extracted from the cells using an RNA extraction kit (such as RNeasy Mini kit, Qiagen). The ChgA expression level is then assessed by Quantitative real-time PCR using a one-step qPCR kit (such as QuantiTech Probe PCR kit, Qiagen) and ChgA primers and probes (such as commercially available Taqman probe for mouse ChgA, Life Technologies).

"mRNA Insulin Expression Assay" refers to an assay used to determine the relative insulin mRNA expression level of a cell population. For example, the assay can determine the insulin mRNA level expressed in a cell population treated to increase the expression of insulin in the cells, as compared to an untreated population of cells. In an exemplary mRNA Insulin Expression Assay, the cells were collected and the RNA is extracted from the cells using an RNA extraction kit (such as RNeasy Mini kit, Qiagen). The insulin expression level is then assessed by Quantitative real-time PCR using a one-step qPCR kit (such as QuantiTech Probe PCR kit, Qiagen) and Ins1 or Ins2 primers and probes (such as the commercially available TaqMan probe for mouse Ins1 and Ins2, Life Technologies). The relative insulin mRNA expression can be determined relative to a baseline or other marker, such as Hprt mRNA expression level or other baseline marker.

"NeuroD1 activator" is a substance that activates NeuroD1.

"Non-human mammal", as used herein, refers to any mammal that is not a human.

"Notch inhibitor" refers to an inhibitor of the Notch signaling pathway.

"Ngn3" refers to Neurogenin-3, a protein expressed in endocrine progenitor cells and associated with enteroendocrine differentiation.

"Ngn3 Assay" as used herein is an assay used to determine the extent of expression of Ngn3 in cells, such as cells subjected to a differentiation protocol. In an exemplary Ngn3 Assay, RNA is isolated from cells that have been cultured according to a differentiation protocol, and quantitative real-time PCR is performed using commercially available primers and probes (such as Taqman probes) to determine an extent of Ngn3 expression in the cells.

As used in relevant context herein, the term "number" of cells can be 0, 1, or more cells.

"Organoid" or "epithelial organoid" refers to a cell cluster or aggregate that resembles an organ, or part of an organ, and possesses cell types relevant to that particular organ.

"Population" of cells refers to any number of cells greater than 1, and even at least $1 \times 10^3$ cells, at least $1 \times 10^4$ cells, at least at least $1 \times 10^5$ cells, at least $1 \times 10^6$ cells, at least $1 \times 10^7$ cells, at least $1 \times 10^8$ cells, at least $1 \times 10^9$ cells, or at least $1 \times 10^{10}$ cells.

"Post-natal cell" refers to a non-embryonic cell. Post-natal cells can include at least one of post-natal stem cells, post-natal progenitor cells, and post-natal multipotent progeny cells, as well as one or more cells differentiated from these cells, such as enteroendocrine cells (EECs).

"Post-natal stem cell" refers to non-embryonic stem cells that have the capacity to self renew and to differentiate into multiple cell lineages. Post-natal stem cells may also be referred to as adult stem cells or somatic stem cells. Post-natal stem cells can include intestinal stem cells, epithelial stem cells, hematopoietic stem cells, mammary stem cells, mesenchymal stem cells, endothelial stem cells and neural stem cells.

"Progenitor cell" as used herein refers to a cell that, like a stem cell, has the tendency to differentiate into a specific type of cell, but is already more specific than a stem cell and is pushed to differentiate into its "target" cell.

"Reference" means a standard or control condition (e.g., untreated with a test agent or combination of test agents).

The term "sample" refers to a volume or mass obtained, provided, and/or subjected to analysis. In some embodiments, a sample is or comprises a tissue sample, cell sample, a fluid sample, and the like. In some embodiments, a sample is taken from (or is) a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these.

"Self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

"Small molecule" as referred to herein refers to an organic compound that can participate in regulating biological pathways, and is a non-nucleic acid, is typically non-peptidic and non-oligomeric, and may have a molecular weight of less than 1500 daltons.

"Stem cell" refers to a multipotent cell having the capacity to self renew and to differentiate into multiple cell lineages.

"Stem Cell Markers" as used herein can be defined as gene products (e.g. protein, RNA, etc) that are specifically expressed in stem cells. One type of stem cell marker is gene products that directly and specifically support the maintenance of stem cell identity. Examples include Lgr5 and Sox2. Additional stem cell markers can be identified using assays that were described in the literature. To determine whether a gene is required for maintenance of stem cell identity, gain-of-function and loss-of-function studies can be used. In gain-of-function studies, over expression of specific gene product (the stem cell marker) would help maintain the stem cell identity. While in loss-of-function studies, removal of the stem cell marker would cause loss of the stem cell identity or induced the differentiation of stem cells. Another type of stem cell marker is a gene that is only expressed in stem cells but does not necessarily have a specific function to maintain the identity of stem cells. This type of marker can be identified by comparing the gene expression signature of sorted stem cells and non-stem cells by assays such as micro-array and qPCR. This type of stem cell marker can be found in the literature (e.g. Liu Q. et al., Int J Biochem Cell Biol. 2015 March; 60:99-111. www.ncbi.nlm.nih.gov/pubmed/25582750). Potential stem cell markers include Ccdc121, Gdf10, Opcm1, Phex, etc. The expression of stem cell markers such as Lgr5 or Sox2 in a given cell or cell population can be measured using assays such as qPCR, immunohistochemistry, western blot, and RNA hybridization. The expression of stem cell markers can also be measured using transgenic cells expressing reporters which can indicate the expression of the given stem cell markers, e.g. Lgr5-GFP or Sox2-GFP. Flow cytometry analysis can then be used to measure the activity of reporter expression. Fluorescence microscopy can also be used to directly visualize the expression of reporters. The expression of stem cell markers may further be determined using microarray analysis for global gene expression profile analysis. The gene expression profile of a given cell population or purified cell population can be compared with the gene expression profile of the stem cell to determine similarity between the 2 cell populations. Stem cell function can be measured by colony forming assay or sphere forming assay, self-renewal assay and differentiation assay. In a colony (or sphere) forming assay, when cultured in appropriate culture media, the stem cell should be able to form colonies, on cell culture surface (e.g. cell culture dish) or embedded in cell culture substrate (e.g. Matrigel) or be able to form spheres when cultured in suspension. In a colony/sphere forming assay, single stem cells are seeded at low cell density in appropriate culture media and allowed to proliferate for a given period of time (7-10 days). The colonies formed are then counted and scored for stem cell marker expression as an indicator of stemness of the original cell. Optionally, the colonies that formed are then picked and passaged to test their self-renewal and differentiation potential. In a self-renewal assay, when cultured in appropriate culture media, the cells should maintain stem cell marker (e.g., Lgr5) expression over at least one (e.g., 1, 2, 3, 4, 5, 10, 20, etc.) cell divisions.

"Subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Synergy" or "synergistic effect" is an effect which is greater than the sum of each of the effects taken separately; a greater than additive effect.

"TgfBeta inhibitor" (Tgf-β inhibitor) as used herein is a substance that reduces activity of the TgfBeta pathway. An example of a TgfBeta inhibitor can be a TgfBeta receptor inhibitor, which may include but is not limited to Alk4, Alk7 and Alk5/TgfBeta-RI.

"Tissue" is an ensemble of similar cells from the same origin that together carry out a specific function.

"Treating" as used herein in connection with a cell population means delivering a substance to the population to effect an outcome. In the case of in vitro populations, the substance may be directly (or even indirectly) delivered to the population. In the case of in vivo populations, the substance may be delivered by administration to the host subject.

"Valproic acid" (VPA) has chemical formula $C_8H_{16}O_2$ and the following alternate name: 2-propylpentanoic acid. The sodium salt of valproic acid can also be used in place of VPA, and the term "VPA" is used interchangeable herein to refer to VPA or pharmaceutically acceptable salts thereof, such as the sodium salt. Its chemical structure is as follows:

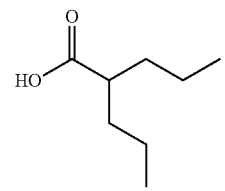

"Wnt activation" as used herein in connection with a substance or composition is an activation of the Wnt signaling pathway.

"Wnt activator" as used herein refers to a substance that activates the Wnt signaling pathway.

"Wnt inhibitor" as used herein refers to a substance that inhibits the Wnt signaling pathway, which can be for example a Wnt receptor inhibitor, Wnt receptor antagonist, a Porcupine inhibitor which inhibits Wnt secretion, or a Tankyrase inhibitor, or a drug that interfere with β-catenin interactions. Examples of Wnt inhibitors include Wnt-C59, IWP-2, IWR-1-endo, AZ6102, FH535, WIKI4, ICG-001, XAV-939, PRI-724, LGK-974, YA1797K, KY02111, Cardionogen 1, and IWP 12, etc.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Examples of pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Example organic bases used in certain embodiments include isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions (e.g., pharmaceutical compositions).

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

DETAILED DESCRIPTION

A description of example embodiments of the disclosure follows.

The present disclosure relates to methods for forming enteroendocrine cells (EECs) from a mammalian post-natal cell population, such as a post-natal stem cell population, by treating with a plurality of small molecules that are capable of activating and/or deactivating pathways and mechanisms that lead to differentiation of the post-natal cell population into EECs. The pathways and mechanisms acted on by the small molecules can include, but are not limited to, Wnt signaling pathways, Notch signaling pathways, EGFR pathways, MEK/ERF signaling pathways, mechanisms acted on by growth factors, Histone Methylation pathways, the Tgf-β signaling pathway, and NeuroD1 pathways. In particular, aspects of the disclosure provide small molecule combinations that can promote differentiation of the post-natal cells such as post-natal stem cells, into EECs, as well as signal the differentiation into a particular EEC cell type.

The present disclosure also relates to methods for increasing the insulin expression in a population of mammalian cells, by treating the population with a plurality of small molecules that are capable of activating and/or deactivating pathways and mechanisms that lead to increased insulin expression on the cells. The cells treated by the small molecule can be either post-natal cells (such as post-natal stem cells or multipotent progeny cells) or enteroendocrine cells, such as EECs that have been differentiated from post-natal cells such as post-natal stem cells, by the method described above. The pathways and mechanisms acted on by the small molecules to increase the insulin production can include, but are not limited to, any of the signaling pathways discussed for EEC differentiation above, such as for example Wnt and Notch signaling pathways, and in particular including small molecules that act to inhibit and/or activate DNA methylation pathways, Tgf-β signaling pathways and NeuroD1 pathways. In particular, aspects of the disclosure provide for small molecule combinations that promote insulin expression in the cells, and that induce cells in the treated population to become insulin producing cells.

In differentiating the post-natal cells such as post-natal stem cells to EECS, the plurality of small molecules is provided such that expression of the differentiation marker ChgA is upregulated due to differentiation of the cells. The expression of ChgA is upregulated such that the fraction of cells expressing ChgA in the cell population that has been treated with the small molecules, as measured in a ChgA Immunostaining Assay, is at least about 1.5%. The fraction of cells expressing ChgA as measured by the ChgA Immunostaining Assay may even be at least about 10%, and even at least about 50%, such as a fraction of cells is in a range of from about 60% to about 100%. In one embodiment, the fraction of cells expressing ChgA may be in a range of from about 1.5% to about 100%. Furthermore, as measured by an mRNA ChgA Expression Assay, the ChgA mRNA expression in the differentiated cell population may be at least about 10 times the ChgA mRNA expression in the initial post-natal cell population. The ChgA mRNA expression may even be at least 100 times the ChgA mRNA expression in the initial post-natal cell population, and may even be in the range of from about 1000 times to 1,000,000 times the ChgA mRNA expression in the initial post-natal cell population. In one embodiment, the ChgA mRNA expression may be in a range of from about 10 to about 1,000,000 times the number of cells expressing ChgA in the initial post-natal cell population.

The differentiation of the cells to form the EECs using the small molecule can provide a highly pure population of enteroendocrine cells, with a significant number of the post-natal cells, such as post-natal stem cells, being converted to the enteroendocrine cells. This ability to convert the post-natal stem cells into EECs in large quantities is significant, because intestinal EECs are restricted to the mucosa, predominantly in its deeper half, and typically comprise only a small minority of the overall epithelial cell population, such as less than 1%. In contrast, treatment with the small molecules as described herein converts the post-natal cells into the enteroendocrine cells such that percentage of cells expressing the ChgA marker for EECs is at least 2% of the total cell population, and even as high as 90% to even 100% of the cell population, such as from about 60% to about 90% of the total cell population, and even from about 70% to about 80% of the total cell population. As disclosed herein, a final cell population having about 80% EECs has been achieved (see, e.g., FIG. 40). In one embodiment, the percentage of cells expressing ChgA in the obtained cell population is increased as compared to the initial post-natal cell population is an increase in the fraction of ChgA expressing cells of from at least 0.1% to at least 1%, and even an increase of at least about 5%, such as an increase of at least about 10%, and even an increase of at least about 50%, such as at least about 100%.

The post-natal cells that are treated by the small molecules include post-natal stem cells that are non-embryonic stem cells, such as adult stem cells that have the capacity to self-renew and to differentiate into multiple cell lineages, and can also include multipotent progeny cells and/or progenitor cells. The post-natal stem cells can include intestinal stem cells, epithelial stem cells, hematopoietic stem cells, mammary stem cells, mesenchymal stem cells, endothelial stem cells and neural stem cells, which often have conserved signaling and development pathways. In one embodiment, the post-natal stem cells are intestinal stem cells, and may be identified by the marker Lgr5. Lgr5 is a Leucine-rich repeat-containing G-protein coupled receptor 5, also known as G-protein coupled receptor 49 (GPR49) or G-protein coupled receptor 67 (GPR67), and in humans is encoded by the Lgr5 gene. When treating cells with small molecules to increase insulin expression, the cells being treated may be either these post-natal stem cells and/or cells that have been further specified, such as multipotent progeny cells and/or progenitor cells and/or enteroendocrine cells.

Figure 31:
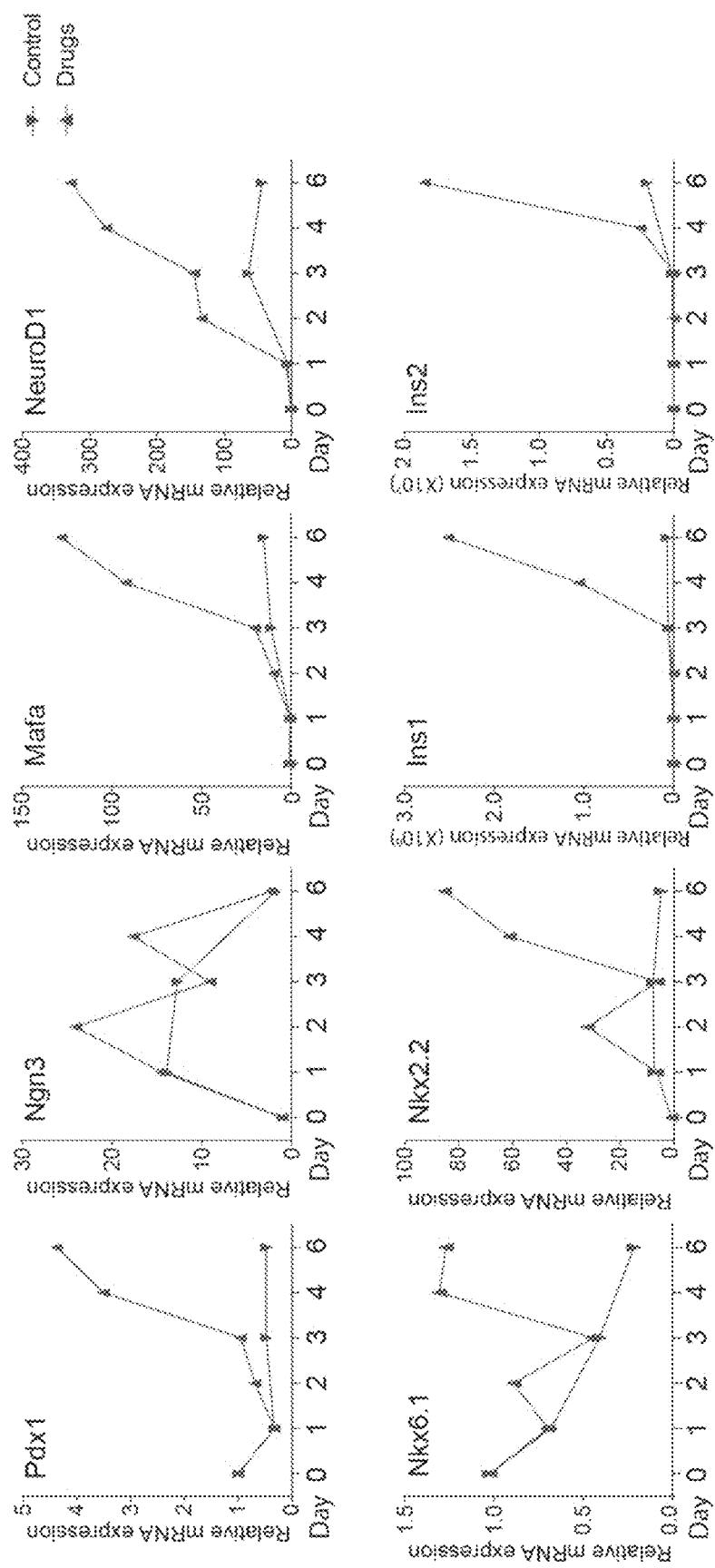
FIG. 31 shows gene expression data.

Treatment of a population of cells with a plurality of small molecules can also be performed to provide a significant increase in the insulin expression of the cells. In one embodiment, the insulin expression can be increased by treatment with the small molecules such that, as measured by an Insulin Activity Assay, the fraction of cells having the Insulin GFP reporter activated in the treated cells is at least about 1%, and even at least about 20%. In one embodiment, the fraction of cells having the Insulin GFP reporter activated is in a range of from about 20% to about 100%. According to a different type of measure, the treatment with the plurality of small molecules may be capable of increasing the insulin expression with respect to the initial cell population, as determined by an mRNA Insulin Expression Assay, to a level substantially greater than a baseline level. For example, in comparing with Hprt mRNA (as a reference gene for expression levels in qPCR), the mRNA Insulin Expression Assay may provide a mRNA insulin expression level that is in the range of at least about 1 fold and even at least about 2 fold as compared to a standard using Hprt mRNA levels (where the insulin level of islet cells is typically about 100 fold of the Hprt level), thus demonstrating that the cells are being successfully converted into insulin expressing cells. As shown in FIG. 31 herein, a $2 \times 10^7$ fold increase in insulin expression can be achieved as compared to the expression in stem cells, when an arbitrary control Ct value is set for stem cell samples in qPCR (in a case where Insulin mRNA is undetectable at or above the set Ct value in stem cell samples). Furthermore, an insulin mRNA expression level as measured by an mRNA Insulin Expression Assay as compared to insulin mRNA levels in islet cells, is believed to provide at least about 0.01%, such as at least about 0.1%, an even at least about 1%, up to at least about 10%, and even 100% or 200% of the insulin mRNA activity as compared to the islets. According to one embodiment, subjecting a cell population to treatment with the plurality of small molecules can provide a resulting cell population where at least about 1% of the obtained cells are insulin producing cells, and the number of insulin producing cells in the obtained cell population may even be in a range of from about 1% to about 20% of the total cell population.

Treatment of a population of EECs with a plurality of small molecules can also be performed to generate subset populations comprising, for example, L-cells, K-cells, I-cells, G-cells, EC-cells, N-cells, and S-cells.

Figure 34:
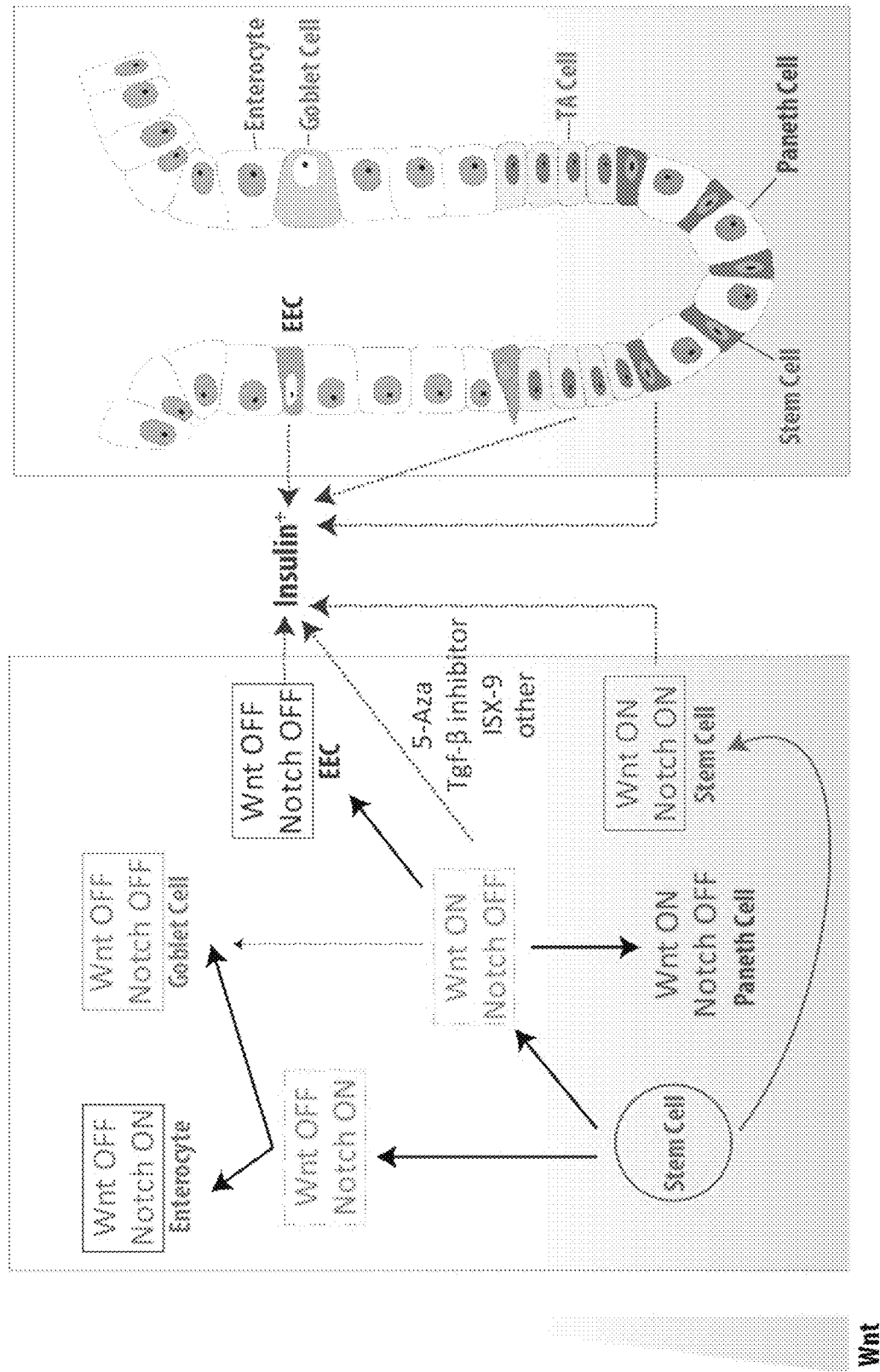
FIG. 34 shows a model of in vivo EEC differentiation controlled by Wnt and Notch pathways.

The population of mammalian cells treated by the small molecules can be an in vitro population, such as a population of cells dispersed in a cell culture medium. An in vitro population of cells may also be in the form of organoids, which is a cell cluster or aggregate that resembles an organ, or part of an organ, and possesses cell types relevant to that particular organ (Sato, 2009). Alternatively, the population of mammalian cells treated by the small molecules may be an in vivo population, such as in vivo treatment of a human or other mammal to treat a disease state. In another alternative, the population of mammalian cells treated by the small molecules may be an ex vivo population, such as a population of cells obtained (e.g., isolated, derived) from a human or other mammal (e.g., a human or other mammal in need of treatment). A proposed mechanism for one embodiment for the differentiation of EECs from post-natal cells such as post-natal stem cells, is provided in FIG. 34. Without being limited by any particular theory, it is presently believed that by controlling the Wnt and Notch pathways, and optionally other pathways, the EECs can be specified from the stem cells. In particular, in the mechanism as shown provides for activating the Wnt pathway while inhibiting the Notch pathway, and then inhibiting both the Notch and Wnt pathways to form EECs. Other mechanisms and/or pathways may also be activated and/or inhibited, as described below, to further specify differentiation along the pathway towards EECs (as opposed to goblet cells, enterocytes, Paneth cells, etc.), and other mechanisms and/or pathways may also be used to further specify particular types of EECs, and/or EEC function. For example, while FIG. 34 shows Wnt inhibition, in some embodiments it may be possible to provide the differentiation to EEC without requiring addition of a Wnt inhibitor. Also, while FIG. 34 illustrates a two stage method for obtaining EECS, certain embodiments may also provide for just a single stage of treatment, or even 3 or more stages of treatment to achieve the EECs. Particular types of EECs that might be specified can include cells that express GLP-1, SHT, SST, gastrin, CCK, SCT, NTS, PYY, and ghrelin, among others.

In embodiments of the method of increasing insulin production of mammalian cells as described herein, treatment of the mammalian cells may result in differentiation along a similar pathway as that shown in FIG. 34, such as from post-natal stem cells to EECs, with the resulting cells being those that provide increased insulin production, and/or the treatment may be performed on EECs themselves, to convert these cells into cells with increased insulin production. That is, the treatment to increase insulin production of the cells can be performed simultaneously with, before, or after differentiation of post-natal stem cells into EECS, or can be performed on cells at a differentiation stage in between stem cells and EECS, as well on the post-natal stem cells or EECs themselves. Accordingly, the treatment to increase insulin production can be performed on a mammalian cell population that comprises at least one of post-natal stem cells (such as Lgr5+ cells), progenitor cells and differentiated enteroendocrine cells.

FIG. 34 also shows the different types of intestinal cells, such as EECs, enterocytes, goblet cells, Paneth cells and stem cells and a general configuration of such cells as found in the crypts of the intestine. This figure shows that, as discussed above, the enteroendocrine (EEC) cells are typically located in such crypts, and are only present in a small percentage of the total cells therein (<1%), and thus it has been difficult to test mechanisms for disease treatment in the absence of an in vitro method for obtaining an EEC population of cells.

As discussed above, in one embodiment the plurality of small molecules provided to treat the post-natal cell population (such as a post-natal stem cell population) to achieve differentiation to EECs, and/or to treat a cell population to increase the insulin expression thereof, includes a small molecule that acts to activate and/or inhibit the Wnt pathway. The Wnt signaling pathway is a signal transduction pathway activated by binding of a Wnt protein ligand to a Frizzled family receptor. Wnt activators that can be provided as a part of a treatment can include, for example, at least one of R-Spondin 1, Wnt3a, Gsk inhibitors such as at least one of CHIR99021, LY2090314, NP031112 (Tideglusib), lithium, A1070722, SKL2001, and other agents capable of activating the Wnt signaling pathway. In one embodiment, a Wnt activator provided as a part of a plurality of small molecules can be R-Spondin 1, which is a protein belonging to the R-Spondin family. Wnt inhibitors that can be provided as a part of a treatment can include, for example, at least one of Wnt-C59, Dkk family proteins (such as at least one of Dkk-1, Dkk2, Dkk3 and Dkk4), sFRPs (such as at least one of sFRP-1 and sFRP-2), antibodies against Wnt receptors such as OMP-18R5, other small molecule Wnt inhibitors such as LGK974, CWP232291, PRI-724, IQR-1, IWP2, IWP-L6, ICG-001, WIKI4, Ky02111, FH535, XAV939, NSC668036, FJ9, 3289-8625, and others (Kahn, 2014). In one embodiment, a Wnt inhibitor provided as a part of a plurality of small molecules for treatment can be Wnt-C59, which has the following chemical structure:

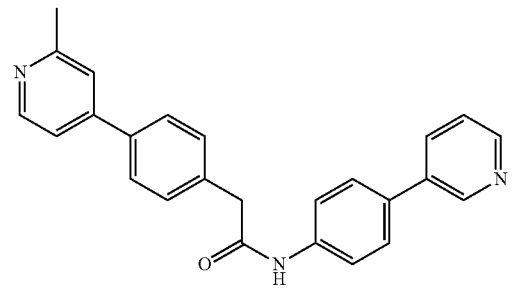 [SMILES: Cc1cc(-c2ccc(CC(=O)Nc3ccc(-c4cccnc4)cc3)cc2)ccn1]

Derivatives and/or pharmaceutically acceptable salts of the Wnt activator and/or Wnt inhibitor may also be provided.

Further Examples of Wnt agonists which may be suitable as Wnt activators can be found in the following Table.

TABLE

| Wnt Agonist | |
| --- | --- |
| Column A Wnt Ligand | Column B Wnt1/Int-1 |
| | Wnt-2/Irp (Int-I-related protein) |
| | Wnt-2b/13 |
| | Wnt-3/Int-4 |
| | Wnt-3a |
| | Wnt-4 |
| | Wnt-5a |
| | Wnt-5b |
| | Wnt-6 |
| | Wnt-7a |
| | Wnt-7b |
| | Wnt-8a/8d |
| | Wnt-8b |
| | Wnt-9a/14 |
| | Wnt-9b/14b/15 |
| | Wnt-10a |
| | Wnt-10b/12 |

TABLE-continued

Wnt Agonist

| Column A<br>Wnt Ligand | Column B<br>Wnt1/Int-1 |
|---|---|
| Wnt Related Protein | Wnt-11<br>Wnt-16<br>R-Spondin 1/2/3/4<br>Norrin |
| GSK3b inhibitor | |
| Other Wnt modulator | |
| | (hetero)arylpyrimidines<br>Wnt Agonist<br>IQ 1<br>DCA<br>QS 11<br>WASP-1, ZINC00087877<br>WAY 316606, HCl<br>WAY-262611, HCl<br>HLY78<br>SKL2001<br>Cpd1<br>Cpd2<br>cmpd 109<br>ISX 9<br>Cmpd 71<br>Cmpd 2<br>Selumetinib (AZD6244)<br>Radicicol<br>(hetero)arylpyrimidines<br>Wnt Agonist<br>WAY 316606, HCl<br>WAY-262611, HCl<br>SKL2001<br>ISX 9 |

In one embodiment the plurality of small molecules provided to treat the post-natal cell population to achieve differentiation to EECs, and/or to treat a cell population to increase the insulin expression thereof, includes a small molecule that acts to inhibit the Notch pathway. Notch inhibitors that can be provided as a part of a treatment can include, for example, at least one of DAPT; LY411575; MDL-28170; R04929097; L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); M-0752; YO-01027; MDL28170 (Sigma); LY41 1575 (N-2 ((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide); ELN-46719 (2-hydroxy-valeric acid amide analog of LY41 1575; PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl) pentanamide); Compound E ((2S)-2-{[(3,5-Difluorophenyl) acetyl]amino}-N-[(3S)-1-methyl-2-oxo-5-phenyl-2,3-dihydro-1H-1,4-benzodiazepin-3-yl]propanamide; and Semagacestat (LY450139; (2S)-2-hydroxy-3-methyl-N-((1 S)-1-methyl-2-{[(1 S)-3-methyl-2-oxo-2,3,4,5-tetrahydro-1H-3-benzazepin-1-yl]amino}-2-oxoethyl)butanamide). In one embodiment, a Notch inhibitor provided as a part of a plurality of small molecules can be DAPT, also known as N—[N-(3,5-Difluorophenacetyl)-L-alanyl]-S-phenylglycine t-butyl ester. Derivatives and/or pharmaceutically acceptable salts of the Notch inhibitor may also be provided.

The plurality of small molecules provided for treatment may also include a small molecule that acts to inhibit the MEK/ERK pathway. This can include inhibitors of the core Ras-Raf-MEK-ERK signaling cascade, as well as inhibitors of proteins upstream or downstream of this core signaling cascade, such as EGF receptor (EGFR) inhibitors. MEK/ERK inhibitors provided for treatment can include, for example, at least one of PD0325901, AZD8330 (ARRY-424704), Refametinib (BAY 86-9766, RDEA119), Cobimetinib (GDC-0973, XL-518, RG7421), E6201, MEK162 (ARRY-438162), Pimasertib (AS703026, MSC1936369B), R04987655 (CH4987655), R05126766 (CH5126766), Selumetinib (AZD6244, ARRY-142,886), TAK-733, Trametinib (GSK1120212), and GDC-0623, WX-554 (Zhao and Adjei, 2014), and may also and/or alternatively include EGFR inhibitors such as Erlotinib, Gefitinib, Lapatinib, Afatinib, Neratinib, AZ5104, Afatinib, PD 153035, CL-387785, AST-1306, PD 168393, Canertinib, and other EGFR inhibitors, as well as Ras and Raf inhibitors. In one embodiment, a MEK/ERK inhibitor provided as a part of a plurality of small molecules can be PD0325901, also known as N-[(2R)-2,3-Dihydroxypropoxy]-3,4-difluoro-2-[(2-fluoro-4-iodophenyl)amino]-benzamide. Derivatives and/or pharmaceutically acceptable salts of the MEK/ERK inhibitor may also be provided.

The plurality of small molecules provided for treatment may also include a small molecules corresponding to various growth factors, such as at least one of epidermal growth factor (EGF) and Noggin. In one embodiment, the growth factors provided as a part of the small molecules for treatment include EGF and/or Noggin. Derivatives and/or pharmaceutically acceptable salts of the growth factors may also be provided. In another embodiment, the plurality of small molecules can include an HDAC Inhibitor (Histone deacetylase inhibitor). An HDAC inhibitor that can be provided as a part of the plurality of small molecules for treatment can include Tubastatin A, ACY1215, Valproic acid, SAHA, Trichostatin A, SHBA, CBHA, LAQ-824, PDX-101, LBH-589, ITF2357, PCI-24781, Compound 7 (ChemieTek), JNK-24681585 (Quisinostat) SB939 (Pracinostat), 4SC-201 (Resminostat), Tefinostat (CHR-2845), CHR-3996, CG200745, Depsipeptide (Romidepsin), Butyrate, MS-275, MGCD0103 and CI994, among others. In one embodiment, an HDAC inhibitor provided for treatment can be Tubastatin A, also called N-Hydroxy-4-(2-methyl-1,2,3,4-tetrahydropyrido[4,3-b]indol-5-ylmethyl)benzamide hydrochloride. Derivatives and/or pharmaceutically acceptable salts of the HDAC inhibitor may also be provided.

Further examples of HDAC inhibitors can be found in the following Table.

TABLE

HDAC Inhibitors

| Column A<br>Class | Column B<br>Agent |
|---|---|
| Hydroxamates | Trichostatin A (TSA) |
| Hydroxamates | SAHA (Zolinza, vorinostat) |
| Hydroxamates | 4-iodo-SAHA |
| Hydroxamates | SBHA |
| Hydroxamates | CBHA |
| Hydroxamates | LAQ-824 |
| Hydroxamates | PDX-101 (belinostat) |
| Hydroxamates | LBH-589 (panobinostat) |
| Hydroxamates | ITF2357 (Givinostat) |
| Hydroxamates | PCI-34051 |
| Hydroxamates | PCI-24781 (Abexinostat) |
| Hydroxamates | Tubastatin A |
| Hydroxamates | CUDC-101 |
| Hydroxamates | Compound 7 |
| Hydroxamates | Oxamflatin |
| Hydroxamates | ITF2357 |
| Hydroxamates | Bufexamac |

TABLE-continued

HDAC Inhibitors

| Column A Class | Column B Agent |
|---|---|
| Hydroxamates | APHA Compound 8 |
| Hydroxamates | JNJ-26481585 (Quisinostat) |
| Hydroxamates | Suberoylanilide-d5 Hydroxamic Acid |
| Hydroxamates | HDAC Inhibitor XXIV |
| Hydroxamates | Tubacin |
| Hydroxamates | Butyrylhydroxamic acid |
| Hydroxamates | 1-Naphthohydroxamic Acid |
| Hydroxamates | MC 1568 |
| Hydroxamates | SB939 (Pracinostat) |
| Hydroxamates | 4SC-201 (Resminostat) |
| Hydroxamates | Tefinostat (CHR-2845) |
| Hydroxamates | CHR-3996 |
| Hydroxamates | CG200745 |
| Cyclic peptide | Depsipeptide (Romidepsin, FK-228, FR 901228) |
| Cyclic peptide | Trapoxin A |
| Cyclic peptide | HC Toxin |
| Aliphatic Acid | Valproic Acid |
| Aliphatic Acid | VAHA |
| Aliphatic Acid | Phenyl butyrate |
| Aliphatic Acid | Butyrate |
| Aliphatic Acid | AN-9 |
| Benzamides | MS-275 (Entinostat) |
| Benzamides | MGCD0103 (Mocetinostat) |
| Benzamides | CI994 (Tacedinaline; PD-123654; GOE-5549; Acetyldinaline) |
| Benzamides | BML-210 |
| Hydroxamates | M 344 |
| Benzamides | Chidamide |
| Hydroxamates | 4-(dimethylamino)-N-[6-(hydroxyamino)-6-oxohexyl]-benzamide |
| Miscellaneous | Luteolin |
| Prodrug of thiol | PTACH |
| Miscellaneous | L-Carnitine |
| Miscellaneous | Biphenyl-4-sulfonyl chloride |
| Miscellaneous | SIRT1/2 Inhibitor VII |
| Hydroxamates | (S)-HDAC-42 |
| Hydroxamates | Indole-3-acetamide |
| Miscellaneous | NSC 3852 |
| Miscellaneous | PPM-18 |
| Miscellaneous | Ratjadone A, Synthetic |
| Benzamides | N-(2-Aminophenyl)-N'-phenylheptanediamide |
| Miscellaneous | Dihydrochlamydocin |
| Miscellaneous | 7-Aminoindole |
| Miscellaneous | Apicidin |
| Miscellaneous | Parthenolide |
| Hydroxamates | HNHA |
| Miscellaneous | Splitomicin |
| Benzamides | RGFP109 |
| Benzamides | RGFP136 |
| Benzamides | RGFP966 |
| Benzamides | 4SC-202 |
| Hydroxamates | ACY1215 |
| Miscellaneous | ME-344 |
| Miscellaneous | Sulforaphane |
| CF3Methyl Ketones | 6H |
| CF3Methyl Ketones | 27 |
| Aryl Ketones | 25 |
| Non classical | 5 |
|  | Nexturastat A |
|  | Droxinostat |
|  | AR-42 |
|  | Romidepsin (FK228, Depsipeptide) |
|  | Scriptaid |
|  | Sodium Phenylbutyrate |
|  | TMP269 |
|  | Thailandepsin A |
|  | BRD9757 |
|  | LMK235 |
|  | HPOB |
|  | CAY10603 |
|  | Tasquinimod |
|  | HDAC6 Inhibitor III |
|  | HDAC Inhibitor XXIV |
|  | HDAC Inhibitor IV |
|  | HDAC Inhibitor XIX |
|  | HDAC Inhibitor XXII |
|  | HDAC Inhibitor VII |
|  | HDAC Inhibitor II |
|  | HDAC Inhibitor VI |
|  | (−)-Depudecin |
|  | KD 5170 |
|  | TC-H 106 |
|  | TCS HDAC6 20b |
|  | Pyroxamide |
|  | Chidamide |
|  | HDAC-IN-1 |
|  | HC Toxin |
| Hydroxamates | SAHA (Zolinza, vorinostat) |
| Hydroxamates | LBH-589 (panobinostat) |
| Hydroxamates | JNJ-26481585 (Quisinostat) |
| Cyclic peptide | Depsipeptide (Romidepsin, FK-228, FR 901228) |
| Benzamides | MGCD0103 (mocetinostat) |
| Prodrug of thiol | PTACH |
| Miscellaneous | Ratjadone A, Synthetic |
| Miscellaneous | Apicidin |
| CF3Methyl Ketones | 27 |
| Non classical | 5 |
|  | Nexturastat A |
|  | Droxinostat |
|  | Scriptaid |
|  | BRD9757 |
|  | HPOB |
|  | CAY10603 |
|  | HDAC6 Inhibitor III |
| Hydroxamates | ACY1215 |
| Hydroxamates | Tubastatin A |
| Hydroxamates | Tubacin |
| Hydroxamates | Trichostatin A (TSA) |

A Histone Methylation inhibitor (e.g., Histone demethylase (HDM) inhibitor) that can be provided as a part of the plurality of small molecules for treatment can include at least one of Tranylcypromine, GSK-2879552, GSK-LSD1, SP-2509, GSK J4, 2,4-Pyridinedicarboxylic Acid, ML324, IOX 1, OG-L002, CBB1007, GSK J1, GSK J2, and GSK J5, among others. In one embodiment, a Histone Methylation inhibitor provided for treatment can be Tranylcypromine. In an embodiment, a Histone Methylation inhibitor provided for treatment can be a lysine-specific histone demethylase (LSD1). Derivatives and/or pharmaceutically acceptable salts of the Histone Methylation inhibitor may also be provided. Examples of Histone Methylation inhibitors include: JmjC-domain demethylase: Jmjd2, Jmjd2C, Jmjd3; Lysine-specific demethylase: LSD1 inhibitors such as Tranylcypromine (LSD1), RN 1 (LSD 1), GSK2879552 (LSD1), CBB1003 (LSD1), OG-L002 (LSD1), CBB1007 (LSD1), 2,4-Pyridinedicarboxylic Acid (LSD), SP2509 (LSD1), ORY-1001 (RG-6016), GSK LSD1 (LSD1); Jmjd: Daminozide (Jmjd), GSK J1 (Jmjd3/UTX), GSK J4 (Jmjd3), IOX 1 (Jmjd), JIB 04 (Jmjd), NSC 636819 (KDM4A/KDM4B), TC-E 5002 (KDM2/7), Pargyline, ML324 (Jmjd2);

A Tgf-β inhibitor that can be provided as a part of the plurality of small molecules for treatment can include at least one of 616452 (Repsox), LY-364947, SB-505124, A-83-01, SB-431542, TGF-β RI Kinase Inhibitor VII, SB-525334, TGF-β RI Kinase Inhibitor IX, GW788388, LY2109761, Galunisertib (LY2157299), EW-7197, Pirfenidone, K02288, D 4476, R 268712, A77-01, and SM16, as well as antibodies against Tgf-β receptors. In one embodiment, a Tgf-β inhibitor provided for treatment can be 616452, also referred to as RepSox, with the chemical formula 2-[3-(6-methyl-2-pyridinyl)-1H-pyrazol-4-yl]-1, 5naphthyridine. Derivatives and/or pharmaceutically acceptable salts of the Histone Methylation inhibitor may also be provided.

Further examples of Tgf-β inhibitors can be found in the following Table

| TGF-β Inhibitors | | |
|---|---|---|
| Class | Agent | Alternative Name |
| Tgf-beta-R1 inhibitor | LY-364947 | 616451, TGF-β RI Kinase Inhibitor I, CAS 396129-53-6, [3-(Pyridin-2-yl)-4-(4-quinonyl)]-1H-pyrazole, ALK5 Inhibitor I, LY-364947, HTS-466284 |
| Tgf-beta-R1 inhibitor | Repsox | 616452, TGF-β RI Kinase Inhibitor II, CAS 446859-33-2, 2-(3-(6-Methylpyridin-2-yl)-1H-pyrazol-4-yl)-1,5-naphthyridine |
| Tgf-beta-R1 inhibitor | SB-505124 | 616453, TGF-β RI Kinase Inhibitor III, CAS 356559-13-22-(5-Benzo[1,3]dioxol-4-yl-2-tert-butyl-1H-imidazol-4-yl)-6-methylpyridine, HCl, ALK5 Inhibitor III, SB-505124, HCl |
| Tgf-beta-R1 inhibitor | A-83-01 | 616454, TGF-β RI Kinase Inhibitor IV - CAS 909910-43-6, 3-(6-Methylpyridin-2-yl)-4-(4-quinolyl)-1-phenylthiocarbamoyl-1H-pyrazole, A-83-01, ALK5 Inhibitor IV |
| Tgf-beta-R1 inhibitor | SD-208 | 616456, TGF-β RI Kinase Inhibitor V, CAS 627536-09-8, 2-(5-Chloro-2-fluorophenyl)pteridin-4-yl)pyridin-4-yl amine, SD-208, ALK5 Inhibitor V |
| Tgf-beta-R1 inhibitor | SB-431542 | 616461, TGF-β RI Kinase Inhibitor VI, SB431542 - CAS 301836-41-9, 4-[4-(3,4-Methylenedioxyphenyl)-5-(2-pyridyl)-1H-imidazol-2-yl]benzamide, Dihydrate, 4-[4-(1,3-Benzodioxol-5-yl)-5-(2-pyridyl)-1H-imidazol-2-yl]benzamide, Dihydrate |
| Tgf-beta-R1 inhibitor | TGF-β RI Kinase Inhibitor VII | 616458, TGF-β RI Kinase Inhibitor VII - CAS 666729-57-3, 1-(2-((6,7-Dimethoxy-4-quinolyl)oxy)-(4,5-dimethylphenyl)-1-ethanone, ALK5 Inhibitor VII |
| Tgf-beta-R1 inhibitor | SB-525334 | 616459, TGF-β RI Kinase Inhibitor VIII - CAS 356559-20-1, SB-525334, 6-(2-tert-Butyl-5-(6-methyl-pyridin-2-yl)-1H-imidazol-4-yl)-quinoxaline, ALK5 Inhibitor VIII |
| Tgf-beta-R1 inhibitor | TGF-β RI Kinase Inhibitor IX | 616463, TGF-β RI Kinase Inhibitor IX, 4-((4-((2,6-Dimethylpyridin-3-yl)oxy)pyridin-2-yl)amino)benzenesulfonamide, ALK5 Inhibitor IX |
| Tgf-beta-R1 inhibitor | GW788388 | 4-(4-(3-(pyridin-2-yl)-1H-pyrazol-4-yl)pyridin-2-yl)-N-(tetrahydro-2H-pyran-4-yl)benzamide |
| Tgf-beta-R1 inhibitor | LY2109761 | 7-(2-morpholinoethoxy)-4-(2-(pyridin-2-yl)-5,6-dihydro-4H-pyrrolo[1,2-b]pyrazol-3-yl)quinoline |
| Tgf-beta-R1 inhibitor | Galunisertib (LY2157299) | 4-(2-(6-methylpyridin-2-yl)-5,6-dihydro-4H-pyrrolo[1,2-b]pyrazol-3-yl)quinoline-6-carboxamide |
| Tgf-beta-R1 inhibitor | EW-7197 | N-(2-fluorophenyl)-5-(6-methyl-2-pyridinyl)-4-[1,2,4]triazolo[1,5-a]pyridin-6-yl-1H-imidazole-2-methanamine |
| Tgfb production inhibitor | Pirfenidone | 2(1H)-Pyridinone, 5-methyl-1-phenyl- |
| Tgf-beta-R1 inhibitor | K02288 | 3-[(6-Amino-5-(3,4,5-trimethoxyphenyl)-3-pyridinyl]phenol |
| Tgf-beta-R1 inhibitor | D 4476 | 4-[4-(2,3-Dihydro-1,4-benzodioxin-6-yl)-5-(2-pyridinyl)-1H-imidazol-2-yl]benzamide |
| Tgf-beta-R1 inhibitor | R 268712 | 4-[2-Fluoro-5-[3-(6-methyl-2-pyridinyl)-1H-pyrazol-4-yl]phenyl]-1H-pyrazole-1-ethanol |
| Other | ITD 1 | 4-[1,1'-Biphenyl]-4-yl-1,4,5,6,7,8-hexahydro-2,7,7-trimethyl-5-oxo-3-quinolinecarboxylic acid ethyl ester |
| Smad3 inhibitor | SIS3 | 1,2,3,4-Tetrahydro-6,7-dimethoxy-2-[(2E)-3-(1-phenyl-1H-pyrrolo[2,3-b]pyridin-3-yl)-1-oxo-2-propenyl]-isoquinoline hydrochloride |
| Tgf-beta-R1 inhibitor | A77-01 | 4-[5-(6-methylpyridin-2-yl)-1H-pyrazol-4-yl]quinoline |
| Other | Asiaticoside | |
| Tgf-beta-R1 inhibitor | SM16 | 4-(5-(benzo[d][1,3]dioxol-5-yl)-4-(6-methylpyridin-2-yl)-1H-imidazol-2-yl)bicyclo[2.2.2]octane-1-carboxamide |
| Tgf-beta antibody | ID11 | |
| Tgf-beta antibody | 2G7 | |
| Tgf-beta antibody | GC-1008 | Fresolimumab |
| Tgf-beta antibody | CAT-152 | Lerdelimimab |
| Tgf-beta antibody | CAT-192 | Metelimumab |
| TGf-beta Receptor antibody | PF-03446962 | |

-continued

| TGF-β Inhibitors | | |
|---|---|---|
| Class | Agent | Alternative Name |
| Tgf-beta antibody | SR-2F | |
| Tgf-beta antibody | 2G7 | |
| Tgf-beta antibody | LY2382770 | |
| Tgf-beta antibody | IMC-TR1 | |
| Tgf-beta antibody | STX-100 | |
| TGF-beta antagonist Recombinant protein | TGF-PRII: Fc betaglycan/TGF-PRIII | |
| Oligonucleotide inhibitor | AP12009 | Trabedersen, antisense molecule |
| Oligonucleotide inhibitor | AP11014 | |
| Oligonucleotide inhibitor | AP15012 | |
| | LY-550410 | |
| | LY-580276 | |
| | LY-364947 | |
| | LY-2109761 | |
| | LY-2157299 | Galunisertib |
| | LY-573636 | Is this TGF b inhibitor/YES |
| | SB-505124 | |
| | SB-431542 | |
| | SB-525234 | |
| | SD-208 | |
| | SD-093 | |
| | Ki-26894 | |
| | NPC-30345 | |
| | SX-007 | |
| | IN-1130 | |
| | pyrrole-imidazole polyamide | Gene siliencing |
| | EW-7203 | |
| | EW-7195 | Structure |
| | EW-7197 | |
| | GW6604 | |
| | U.S. Pat. No. 7,087,626 | Pyrrole derivatives as pharmaceutical agents |
| | U.S. Pat. No. 6,476,031 | Quinazoline derivatives as medicaments |
| | U.S. Pat. No. 7,723,486, and EP 0945464 | Antibodies to TGF-β |
| Peptide | Trx-xFoxHIb | Smad-interacting peptide aptamers |
| Peptide | Trx-Lefl | |
| Peptide | Distertide (pI44) | |
| Peptide | pI7 | |
| Peptide | LSKL | |
| dihydropyrrlipyrazole-based scaffold | See US Patent U.S. Pat. No. 8,298,825 B1 | |
| imidazole-based scaffold | See US Patent U.S. Pat. No. 8,298,825 B1 | |
| pyrazolopyridine-based scaffold | See US Patent U.S. Pat. No. 8,298,825 B1 | |
| pyrazole-based scaffold | | See US Patent U.S. Pat. No. 8,298,825 B1 |
| imidazopyridine-based scaffold | See US Patent U.S. Pat. No. 8,298,825 B1 | |
| triazole-based scaffold | | See US Patent U.S. Pat. No. 8,298,825 B1 |
| pyridopyrimidine-based scaffold | See US Patent U.S. Pat. No. 8,298,825 B1 | |
| pyrrolopyrazole-based scaffold | See US Patent U.S. Pat. No. 8,298,825 B1 | |
| isothiazole-based scaffold | See US Patent U.S. Pat. No. 8,298,825 B1 | |
| oxazole-based scaffold | | See US Patent US 8298825 B1 |
| Tgf-beta-R1 inhibitor | Repsox | 616452, TGF-β RI Kinase Inhibitor II, CAS 446859-33-2, 2-(3-(6-Methylpyridin-2-yl)-1H-pyrazol-4-yl)-1,5-naphthyridine |
| Tgf-beta-R1 inhibitor | Galunisertib (LY2157299) | 4-(2-(6-methylpyridin-2-yl)-5,6-dihydro-4H-pyrrolo[1,2-b]pyrazol-3-yl)quinoline-6-carboxamide |
| Tgf-beta-R1 inhibitor | EW-7197 | N-(2-fluorophenyl)-5-(6-methyl-2-pyridinyl)-4-[1,2,4]triazolo[1,5-a]pyridin-6-yl-1H-imidazole-2-methanamine |

TGF-β Inhibitors -continued

| Class | Agent | Alternative Name |
| --- | --- | --- |
| Tgfb production inhibitor | Pirfenidone | 2(1H)-Pyridinone, 5-methyl-1-phenyl- |
| | LY-2157299 | Galunisertib |
| Tgf-beta-R1 inhibitor | SB-505124 | 616453, TGF-β RI Kinase Inhibitor III, CAS 356559-13-22-(5-Benzo[1,3]dioxol-4-yl-2-tert-butyl-1H-imidazol-4-yl)-6-methylpyridine, HCl, ALK5 Inhibitor III, SB-505124, HCl |
| Tgf-beta-R1 inhibitor | SB-525334 | 616459, TGF-β RI Kinase Inhibitor VIII - CAS 356559-20-1, SB-525334, 6-(2-tert-Butyl-5-(6-methyl-pyridin-2-yl)-1H-imidazol-4-yl)-quinoxaline, ALK5 Inhibitor VIII |
| Tgf-beta-R1 inhibitor | TGF-β RI Kinase Inhibitor IX | 616463, TGF-β RI Kinase Inhibitor IX, 4-((4-((2,6-Dimethylpyridin-3-yl)oxy)pyridin-2-yl)amino)benzenesulfonamide, ALK5 Inhibitor IX |
| Tgf-beta-R1 inhibitor | R 268712 | 4-[2-Fluoro-5-[3-(6-methyl-2-pyridinyl)-1H-pyrazol-4-yl]phenyl]-1H-pyrazole-1-ethanol |
| | SB- 505124 | Pyridine, 2-[4-(1,3-benzodioxol-5-yl)-2-(1,1-dimethylethyl)-1H-imidazol-5-yl]-6-methyl-, hydrochloride (1:1) |
| | SD-208 | |
| | IN-1130 | |
| | EW-7197 | |
| Tgf-beta-R1 inhibitor | A-83-01 | 616454, TGF-β RI Kinase Inhibitor IV - CAS 909910-43-6, 3-(6-Methylpyridin-2-yl)-4-(4-quinolyl)-1-phenylthiocarbamoyl-1H-pyrazole, A-83-01, ALK5 Inhibitor IV |
| Tgf-beta-R1 inhibitor | SB-431542 | 616461, TGF-β RI Kinase Inhibitor VI, SB431542 - CAS 301836-41-9, 4-[4-(3,4-Methylenedioxyphenyl)-5-(2-pyridyl)-1H-imidazol-2-yl]benzamide, Dihydrate, 4-[4-(1,3-Benzodioxol-5-yl)-5-(2-pyridyl)-1H-imidazol-2-yl]benzamide, Dihydrate |
| Tgf-beta-R1 inhibitor | R 268712 | 4-[2-Fluoro-5-[3-(6-methyl-2-pyridinyl)-1H-pyrazol-4-yl]phenyl]-1H-pyrazole-1-ethanol |

A NeuroD1 activator that can be provided as a part of the plurality of small molecules for treatment can include ISX-9 and other Isoxazole molecules (Schneider, 2008). In one embodiment, the NeuroD1 activator provided for treatment can be ISX-9, with the chemical formula N-cyclopropyl-5-(2-thienyl)-3-isoxazolecarboxamide. Derivatives and/or pharmaceutically acceptable salts of the Neuro D1 activator may also be provided.

The plurality of small molecules provided for treatment may also include one or more monoamine oxidase (MAO) inhibitors. Examples of MAO inhibitors include Safinamide Mesylate, Rasagiline Mesylate, Tranylcypromine, Moclobemide (Ro 111163), Isatin, 8-(3-Chlorostyryl)-caffeine, Bifemelane hydrochloride, (R)-(−)-Deprenyl hydrochloride, Harmane, Lazabemide hydrochloride, Pirlindole mesylate, RN 1 dihydrochloride, and Tetrindole mesylate, among others.

The plurality of small molecules provided for treatment may also include one or more BMP receptor (including ALK2) inhibitors. Example of BMP receptor (including ALK2) inhibitors include DMH-1, DMH2, Dorspmrphin, K 02288, LDN 193189, and ML 347.

In the treatment of cells to increase insulin expression, a plurality of small molecules that has been shown to be effective in increasing insulin expression of cells is a plurality of small molecules comprising at least one of a DNA methylation inhibitor, a Tgf-β inhibitor, and a NeuroD1 activator. In one embodiment, all three small molecules are provided together as a part of a treatment to increase insulin production in a cell population. The Tgf-β inhibitor and NeuroD1 activator may be any of those discussed above, and/or their derivatives and/or the pharmaceutically acceptable salts thereof, and in particular may correspond to 616452 and ISX-9. The structure of 616452 (Repsox) is as follows:

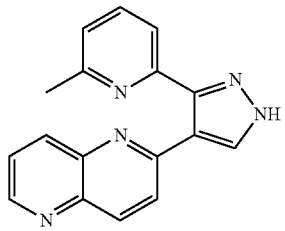 [SMILES: Cc1cccc(-c2n[nH]cc2-c2ccc3ncccc3n2)n1]

The DNA Methylation inhibitor can comprise at least one of 5-Azacytidine, 5-Aza-2-deoxycytidine, RG 108, SGI 1027, Nanaomycin A, Zebularine, Lomeguatrib, SGI-110, and Nanaomycin C, among others. Examples of DNA methylation inhibitors are described in U.S. Pat. No. 8,207,142, Canada Patent No. 2,454,147, and WO 2012/087889, each of which is specifically incorporated herein by reference. In one embodiment, the DNA Methylation inhibitor comprises 5-Azacytidine. Derivatives and/or pharmaceutically acceptable salts of the DNA Methylation inhibitor may also be provided. Additional examples of DNA methylation inhibitors (e.g., DNA methyl transferase (DNMT) inhibitors) include: DNA analog 5-Azacytidine, Zebularine, Decitabine; DNMT inhibitor: Caffeic acid purum, Chlorogenic acid, (−)-Epigallocatechin gallate (EGCG), Hydralazine, Procainamide, Procaine, Psammaplin A, RG108, Fisetin, Lomeguatrib, SGI 1027, 5-Iodotubercidin, 6-Thioguanine, MG98, DC-05, and DC-517.

Table 1 below presents a list of molecules, their abbreviation as otherwise used in the description herein, and examples of the final concentration of each reagent when used in in vitro experiments described herein.

TABLE 1

Summary of growth factors and small molecules used in study

| Reagent Name | Abbreviation | Final Concentration |
|---|---|---|
| EGF | E | 50 ng/ml |
| Noggin | N | 100 ng/ml |
| R-Spondin1 | R | 500 ng/ml |
| CHIR99021 | Chir, C | 5 µM |
| Valproic Acid Sodium Salt | VPA, V | 1.25 mM |
| DAPT | D | 5 µM |
| Tubastatin A | Tu | 10 µM |
| Tranylcypromine | Tranyl, Ty | 2 µM |
| ISX-9 | ISX, I | 10 µM |
| Wnt-C59 | C59, C | 5 µM |
| PD0325901 | Pd | 1 µM |
| 616452/Repsox | 6 | 5 µM |
| 5-Azacytidine | 5-Aza, 5 | 1 µM |

According to one embodiment, the treatment performed using the plurality of small molecules can be performed in several stages, such as a first and second stage, or even more stages. The number of stages used for treatment can be selected according to the differentiation and/or insulin expression increasing method to be performed, as well as with respect to the type of small molecules being used and the pathways being activated and/or inhibited. For example, in a method of treatment to differentiate post-natal cells such as post-natal stem cells into EECs, a first stage may be performed to contact the post-natal cells population with one or more first small molecules that upregulate Ngn3, and in a second stage the post-natal cell population may be contacted with one or more second small molecules that downregulate Ngn3 to decrease Ngn3 expression in the cells. The first and second stages according to this embodiment may promote differentiation of the post-natal cells such as post-natal stem cells towards the formation of EECs. In an embodiment of a method of increasing insulin, first through third stages may be performed to treat cells to upregulate insulin and increase expression.

According to one aspect, a treatment to differentiate post-natal cells such as post-natal stem cells to EECs can comprise first and second stages, with a first stage including contacting the cells with first small molecules including a Notch inhibitor and a Wnt activator, and the second stage including contacting the cells with second small molecules including a Notch inhibitor and at least one of an EGFR inhibitor and a MEK/ERK inhibitor. For example, the first stage may provide R-Spondin1 and DAPT, whereas the second stage may provide DAPT and PD0325901. The second stage may also optionally include a Wnt inhibitor, such as Wnt-C59. The first and second stages may also include one or more growth factors, such as EGF and/or Noggin.

According to yet another aspect, the first stage further comprises contacting the cells with at least one of an HDAC inhibitor, a Histone Methylation Inhibitor, and a NeuroD1 Activator, such as at least one of Tubastatin A, Tranylcypromine and ISX-9. The second stage may further comprise contacting the cells with a Tgf-β inhibitor such as 616452, and/or contacting the cells with a histone methylation inhibitor, such as Tranylcypromine.

In one embodiment, a treatment to increase insulin expression in a cell population can comprise first, second and third stages, with a first stage including contacting the cells with first small molecules including a Notch inhibitor, a Wnt activator and a DNA methylation inhibitor, a second stage including contacting the cells with second small molecules including a Notch inhibitor, optionally a Wnt inhibitor, a Tgf-β inhibitor, and a NeuroD1 activator, and a third stage including contacting the cells with third small molecules including a Notch inhibitor, optionally a Wnt inhibitor, a MEK/ERK inhibitor, and a Tgf-β inhibitor. For example, the first stage may provide R-Spondin1, DAPT, and at least one of 5-Azacytidine and 5-Aza-2-deoxycytidine, whereas the second stage may provide DAPT, Wnt-C59, 616452 and ISX-9, and the third stage may provide DAPT, Wnt-C59, 6116452, and PD0325901. The first, second and/or third stages may also include one or more growth factors, such as EGF and/or Noggin.

According to yet another aspect, the first stage further comprises contacting the cells with at least one of an HDAC inhibitor, a Histone Methylation Inhibitor, and a NeuroD1 Activator, such as at least one of Tubastatin A, Tranylcypromine and ISX-9. The second stage may further comprise contacting the cells with a histone methylation inhibitor, such as Tranylcypromine.

As described herein, the small molecules may be provided in different combinations, and in different stages of treatment, to provide for differentiation of post-natal cells such as post-natal stem cells to EECs and/or increased expression of insulin. Some embodiments of small molecule combinations for treatment are described below.

According to one aspect, a method of differentiation can comprise treating mammalian post-natal cells such as post-natal stem cells with a plurality of small molecules including a Notch inhibitor (e.g. DAPT), a MEK/ERK inhibitor (e.g., PD0325901) and one or more growth factors (e.g., EGF and Noggin). The treatment can be conducted in a single phase.

According to another aspect, a method of differentiation can comprise a first stage with a first set of small molecules including a Notch inhibitor (e.g. DAPT), a Wnt activator (e.g. R-Spondin1), and one or more growth factors (e.g., EGF and Noggin), and a second stage with a Notch inhibitor (e.g. DAPT), a MEK/ERK inhibitor (e.g., PD0325901), and one or more growth factors (e.g., EGF and Noggin).

According to another aspect, a method of differentiation can comprise a first stage with a first set of small molecules including a Notch inhibitor (e.g. DAPT), a Wnt activator (e.g. R-Spondin1), and one or more growth factors (e.g., EGF and Noggin), a HDAC inhibitor (e.g. Tubastatin A) and a Histone Methylation inhibitor (e.g. Tranylcypromine), and a second stage with a Notch inhibitor (e.g. DAPT), a MEK/ERK inhibitor (e.g., PD0325901), and a Histone Methylation inhibitor (e.g. Tranylcypromine).

According to another aspect, a method of differentiation can comprise a first stage with a first set of small molecules including a Notch inhibitor (e.g. DAPT), a Wnt activator (e.g. R-Spondin1), and one or more growth factors (e.g., EGF and Noggin), a HDAC inhibitor (e.g. Tubastatin A) and a Histone Methylation inhibitor (e.g. Tranylcypromine), and a second stage with a Notch inhibitor (e.g. DAPT), a MEK/ERK inhibitor (e.g., PD0325901), a Histone Methylation inhibitor (e.g. Tranylcypromine), and a Wnt inhibitor (e.g., WNT-059).

According to another aspect, a method of differentiation can comprise a first stage with a first set of small molecules including a Notch inhibitor (e.g. DAPT), a Wnt activator (e.g. R-Spondin1), and one or more growth factors (e.g., EGF and Noggin), a HDAC inhibitor (e.g. Tubastatin A), a Histone Methylation inhibitor (e.g. Tranylcypromine), and a NeuroD1 activator (e.g. ISX9), and a second stage with a Notch inhibitor (e.g. DAPT), a MEK/ERK inhibitor (e.g., PD0325901), a Histone Methylation inhibitor (e.g. Tranylcypromine), a Wnt inhibitor (e.g., WNT-059), and a Tgf-β inhibitor (e.g., 616452).

In one embodiment, a method for increasing insulin in a cell population can comprise contacting the cells with small molecules including a DNA methylation inhibitor (e.g. 5-Azacytidine and/or 5-Aza2-deoxycytidine), a Tgf-β inhibitor (e.g. 616452), and a NeuroD1 activator (e.g. ISX-9). The cell population can be contacted with the molecules in a single stage, or can be contacted with one or more of the molecules in a plurality of stages.

In yet another aspect, a method for increasing insulin in a cell population includes a three stage process including, in a first stage, contacting the cells with a Notch inhibitor (e.g. DAPT), a Wnt activator (e.g. R-Spondin1), and a DNA methylation inhibitor (e.g. 5-Azacytidine and/or 5-Aza2-deoxycytidine), in a second stage contacting the cells with a Notch inhibitor (e.g. DAPT), a Wnt inhibitor (e.g. Wnt-C59), a Tgf-β inhibitor (e.g. 616452), and a NeuroD1 activator (e.g. ISX-9), and in a third stage contacting the cells with a Notch inhibitor (e.g. DAPT), a Wnt inhibitor (e.g. Wnt-C59), a Tgf-β inhibitor (e.g. 616452), and a MEK/ERK inhibitor (e.g., PD0325901). Growth factors such as EGF and Noggin can also be provided in the first stage, and the Histone Methylation inhibitor (e.g., Tranylcypromine) can be provided in the first and second stages. A HDAC inhibitor (e.g. Tubastatin A) and/or a NeuroD1 activator (e.g. ISX-9) can also be provided in the first stage.

By performing treatment of post-natal cells such as post-natal stem cells to differentiate cells into enteroendocrine cells, a cell population having a relatively high content of EECs can be obtained. According to one aspect, a cell population having enteroendocrine cells derived from post-natal cells such as post-natal stem cells can be provided by treatment with the plurality of small molecules, wherein a fraction the enteroendocrine cells is at least about 1% of the total cell population. In another aspect, the fraction of the enteroendocrine cells in the cell population may be at least about 10%, such as from 20% to 100% of the total cell population. The cells of the cell population may also be cryopreserved for use in further in vitro or in vivo applications. The cell population is non-sorted, meaning that the cell population has not been filtered or otherwise sorted to achieve the density of the cells. According to one aspect, the differentiated cells may be capable of expressing 5-HT and/or GLP-1, as shown in the Examples included herewith.

Also, the method of increasing insulin production described herein can result in a cell population having a relatively high fraction of insulin producing cells, such as a fraction of insulin producing cells that is at least about 0.05% of the total cell population, and even at least about 1% of the total cell population.

The method for treating cells described herein can be performed by use of kits that provide a cell culture medium, such as matrigel, along with a cell population targeted for the treatment method, and a plurality of small molecules. The kits may also include instructions for using the kit, and other items of equipment to facilitate carrying out the treatment methods. In one embodiment, a kit includes a cell culture medium, mammalian post-natal cells such as post-natal stem cells, and a plurality of small molecules that upregulate ChgA and differentiate the post-natal cells. In another embodiment, a kit includes a cell culture medium, mammalian cells, and a plurality of small molecules that increase insulin production in the cells.

Aspects of the disclosure are further directed to the treatment of disease states in a mammal, such as a human, using the treatment methods described herein. According to one aspect, a disease state characterized by insufficient endocrine or enteroendocrine cell products is treated, such as at least one of obesity, diabetes, irritable bowel syndrome, infectious enteritis, and inflammatory bowel disease. In another aspect, a disease state characterized by insufficient insulin production is treated, such as at least one of obesity, and Type I diabetes. Treatment of the disease state is achieved by way of administering a plurality of small molecules corresponding to any of the small molecules and/or small molecule combinations described above, to a mammal in need of such treatment. In an embodiment, all of the small molecules in a plurality of small molecules are administered (e.g., delivered) to a mammal (e.g., human) in need of such treatment simultaneously (e.g., in a single administration step). In another embodiment, the small molecules in a plurality of small molecules are administered (e.g., delivered) to a mammal (e.g., human) in need of such treatment in multiple administrations (e.g., as part of a multi-step process).

In some embodiments, a plurality of molecules is delivered in vivo to epithelium in a subject, thereby inducing cell differentiation in situ. In particular embodiments, the plurality is delivered to multiple tissues (e.g., stomach, small intestine, colon, oral mucsosa).

According to yet another aspect, pharmaceutical compositions comprising the plurality of small molecules can be prepared, by providing the plurality of small molecules with a pharmaceutically acceptable excipient. In one embodiment, the small molecules can be prepared as a part of a pharmaceutical composition that is capable of providing a protective formulation such that the small molecules are inhibited from breaking down when administered (e.g., orally) until they reach the target area. For example, the formulation may provide a protective coating such that the plurality of small molecules can be made to pass through the stomach to the intestine, where treatment can occur. Such a formulation can include polymeric materials such as poloxamer, and can also include pH sensitive polymers such as eudragit, to provide for release of the small molecules at a target area of the body. The formulation may also be such that release of one of more of the small molecules is controlled, for example to control the onset of release a small molecule, or to control the duration of release of a small molecule at a target area. Also, the formulation can include other compounds that can coat the stomach or gut, such as sucralfate. While a pharmaceutical composition could be administered orally, such as by a pill, gelcap, liquid, etc., other methods of administration can include via a device (e.g. a stent), as well as by a suppository, enema, and/or by a patch. In another embodiment, a cell population obtained by a method described herein may be administered by a cell therapy, such as via infusion, injection, on implant, within or on a carrier material, and may be combined with materials or devices that may be immune isolating (e.g. allogenic transplantation).

In one embodiment, a pharmaceutical composition for treatment of a disease state characterized by insufficient insulin production can comprise a DNA methylation inhibitor, a Tgf-β inhibitor, and a NeuroD1 activator, and/or a derivative and/or pharmaceutically acceptable salt thereof, in combination with a pharmaceutically acceptable excipient. For example the composition can include 616452, ISX-9, and at least one of 5-Azacytidine and 5-Aza-2'deoxycytidine, and/or a derivative and/or pharmaceutically acceptable salt thereof, in combination with a pharmaceutically acceptable excipient. The composition formulation is further devised such that it provides a therapeutically effective amount of the small molecule combination that is effective for treatment of the disease state in the mammal being treated.

In another aspect, the invention relates to a method of preparing a population of cells for transplantation into a subject (e.g., a human) in need thereof. In one embodiment of this aspect, the method comprises a) isolating a population of cells (e.g., from tissue from a subject) comprising Lgr5+ cells; b) treating the cells with one or more molecules that target one or more processes selected from wnt activation, notch inhibition, Tgfβ inhibition, and epigenetic regulation (e.g., LSD1 inhibition and/or HDAC inhibition), or any combination thereof, and c) treating the cells with one or more molecules that target one or more processes selected from wnt inhibition, EGFR inhibition, MEK inhibition, ERK inhibition, epigenetic regulation (e.g. LSD1 inhibition), monoamine oxidase (MAO) inhibition, and notch inhibition, or any combination thereof. For each of steps b) and c), the cells can be treated with the molecules for various periods of time, such as, for example, greater than or equal to about 4, 8, 24, 48, 96, or 192 hrs. Generally, the molecule(s) used in steps b) and c) are used at greater than or equal to about 10, 25, 50, 100, 500, or 1000% of their IC50 values. When multiple molecules are used to treat the cells in steps b) and c), the molecules can be administered simultaneously (e.g., in one step) or separately (e.g., successively).

In another embodiment, the method of preparing a population of cells for transplantation comprises treating a population of progenitor cells (e.g., transit amplifying cells) according to steps b) and/or c) of the preceding paragraph. According to this embodiment, the method can include both of steps b) and c), or it can include step c) without step b). When administering molecules to an in vivo population, the method can include both of steps b) and c), or step b) without step c), or step c) without step b).

In additional embodiments, the method of preparing a population of cells for transplantation further comprises d) delivering the treated population of cells to a subject.

In some embodiments, the cell populations described herein are used for screening of compounds for a variety of purposes (e.g., for enhancing efficiencies of EECs and their subset populations, for controlling size and functions of EECs and their subset populations in vivo, for controlling incretin expression, such as GLP-1 and/or GLP-2 expression, insulin expression, and serotonin expression, for toxicity testing).

EXEMPLIFICATION

Example 1

Mice

Lgr5-EGFP-IRES-CreERT2, B6.129 mice and Insulin-GFP (Ins-GFP, B6.Cg-Tg (Ins1-EGFP)1Hara/J) mice were obtained from Jackson Labs, and 6- to 12-week-old mice were used for crypt cell isolation. Animal experimental procedures were approved by the Committee on Animal Care (CAC) at MIT.

Example 2

Crypt Isolation

Crypts were isolated as previously described (Yin et al., Nature Methods, 2014). The proximal half of the small intestine was harvested, opened longitudinally and washed with cold PBS to remove luminal content. The tissue was then cut into 2 mm to 4 mm pieces with scissors and further washed 5-10 times with cold PBS by pipetting up and down using a 10 mL pipette. Tissue fragments were incubated with 2 mM EDTA in PBS for 30 min on ice. After removal of EDTA, tissue fragments were washed with PBS to release crypts. The crypts were then collected, washed, and used for cell culture. Released crypts were collected and passed through a 70 μm cell strainer. Isolated crypts were embedded in Matrigel and plated at the center of wells in a 24-well plate.

Example 3

Cell Culture

Isolated crypts or single cells were cultured as previously described. 200-300 crypts were mixed with 40 μl of Matrigel and plated at the center of wells in a 24-well plate. Following polymerization of Matrigel, 500 μl of crypt culture media (Advanced DMEM/F12 with N2, B27, Glutamax, HEPES, and N-acetylcysteine) containing growth factors (EGF, Noggin, R-Spondin 1) and small molecules (CHIR99021 and VPA) were provided. For cell differentiation experiments, the cell culture media was changed to media containing growth factors and small molecules as listed in Table 2 following the differentiation protocol as described below. Media were changed every 1-2 days depending on the differentiation condition used.

TABLE 2

Small molecules and growth factors used in study

| Name | Abbreviation | Concentration | | Company | Cat # |
|---|---|---|---|---|---|
| EGF | E | 50 | ng/ml | ThermoFisher | PHG0311 |
| Noggin | N | 100 | ng/ml | Peprotech | 250-38 |
| R-Spondin 1 | R | 500 | ng/ml | Peprotech | 120-38 |
| CHIR99021 | C | 4 | uM | Selleckchem | S1263 |
| VPA (Vaproic Acid Sodium Salt) | V | 1.5 | mM | Sigma | P4543 |
| DAPT | D | 5 | uM | Selleckchem | S2215 |
| IWP 2 | I | 2 | uM | Tocris | 3533 |
| Repsox | Rep | 5 | uM | Tocris | 3742 |
| Tubastatin A | Tu | 10 | uM | Selleckchem | S8049 |
| Tranylcypromine | Tc | 1.5 | uM | Tocris | 3852 |
| PD0325901 | Pd | 1 | uM | Selleckchem | S1036 |
| AS-703026 | As | 1 | uM | Cayman | 11226 |
| Gefitinib | Ge | 1 | uM | Cayman | 13166 |
| Wnt-C59 | C59 | 5 | uM | Selleckchem | S7037 |

Example 4

Immunostaining

Differentiated cell colonies were collected by gently pipetting into a 1.5 ml protein Lobind Eppendorf tube. Cell culture medium was removed, and samples were washed with PBS. Organoids or cell colonies cultured in Matrigel were fixed by directly adding 4% PFA and incubating for 10-30 min at room temperature. Matrigel was then mechanically disrupted, and cells were transferred into BSA-coated Eppendorf tubes. Samples were washed with PBS, permeabilized with 0.25% Triton X-100 for 30 min and stained with primary and secondary antibodies. Antibodies used are listed in Table 3. Images were acquired by confocal microscopy (Zeiss LSM 710) or by inverted microscope (EVOS; Advanced Microscopy Group).

TABLE 3

Antibodies Used in Study

| Antibody | Vendor | Species | Cat # | Dilution |
|---|---|---|---|---|
| ChgA | Santa Cruz | Goat | sc-1488 | 1:100 |
| ChgA | Santa Cruz | Rabbit | sc-13090 | 1:100 |
| GIP | Santa Cruz | Goat | sc-23554 | 1:100 |
| GLP-1 | Abcam | Rabbit | ab22625 | 1:100 |
| 5-HT | Immunostar | Rabbit | 20080 | 1:400 |
| SST | Santa Cruz | Goat | sc-7819 | 1:200 |
| Secretin | Santa Cruz | Goat | sc-21023 | 1:50 |
| CCK-8 | Immunostar | Rabbit | 20078 | 1:200 |
| Anti-Rabbit | Invitrogen | Donkey | A-21206 | 1:400 |
| Anti-Goat | Invitrogen | Donkey | A-11055 | 1:400 |
| Anti-Goat | Invitrogen | Donkey | A-11058 | 1:400 |
| Anti-Rabbit | Invitrogen | Donkey | A-21207 | 1:400 |

Example 5

RNA Extraction and qPCR

Organoids or differentiated cells were harvested and RNA was extracted using RNeasy Micro Kit (Qiagen) according to the manufacturer's instruction. Quantitative real-time PCR was performed with QuantiTect Probe PCR kit (Qiagen) using commercially available primers and TaqMan probes (Life Technologies).

Example 6

GLP-1 Secretion/Release Assay

The cells were collected in 1.5-ml Eppendorf tubes and washed with basic assay medium (HBSS supplemented with 10 mM HEPES, 0.1% fatty acid-free BSA, and no glucose, pH 7.4). The cells were incubated in the basic medium for 2 h in a thermomixer at 300 rpm. The cells were then washed and incubated in 50 µl of basic medium containing 1 mg/ml diprotin A (Sigma-Aldrich) for 1 h, and the supernatant was collected. The cells were then incubated in 50 µl of basic medium containing 1 mg/ml diprotin A and 10 mM glucose for 1 h, and the supernatant was collected. Organoids from 24-well plate were collected in 1.5-ml protein Lobind Eppendorf tubes (1 well per tube) and incubated in basal medium (Hanks' balanced salt solution (Life Technologies) supplemented with 10 mmol/L HEPES, 0.1% fatty acid-free BSA, and no glucose, PH 7.4) for 2 hours in a thermomixer at 300 rotations per minute. Organoids were then washed and incubated in 100 µl basal solution containing 1 mg/ml Diprotin A (Sigma-Aldrich) for 1 hour. the supernatant was collected and the organoids were further incubated in 100 µl basal solution containing 1 mg/ml Diprotin A and 10 mM glucose for 1 hour. The cells and organoids were then lysed in CelLytic M buffer (Sigma-Aldrich). GLP-1 concentrations in the supernatant were determined by ELISA (Multi-Species GLP-1 total ELISA, Millipore). DNA content in the cell lysate was quantified using the PicoGreen Kit and used to normalize GLP-1 content.

Example 7

Insulin Release Assay

The cells were collected in 1.5-ml Eppendorf tubes and washed with Krebs-Ringer buffer (KRB) supplemented with 0.25% BSA, and without glucose. The cells were then incubated with KRB containing either 2 mM or 20 mM glucose for 1 h at 37° C. Supernatant was collected and insulin was measured using HTRF insulin assay (Cisbio).

Example 8

Notch Inhibitor Increases Enteroendocrine Cells (EEC) Differentiation from ISCs (FIG. 1)

Intestinal stem cells can be cultured in 3D Matrigel to form organoids, in which stem cells spontaneously differentiate and generate to all intestinal epithelial cell types, including EEC. Notch inhibition with small molecule γ-secretase inhibitor (DAPT) increases EEC differentiation, with around 5%-10% of the stem cells turned into EECs, as shown in FIG. 1, where immunostaining of EEC marker ChgA under organoid culture conditions (ENR), or in the presence of Notch inhibitor DAPT (ENRD) conditions. DAPI was used for nucleus staining.

Example 9

Figure 2:
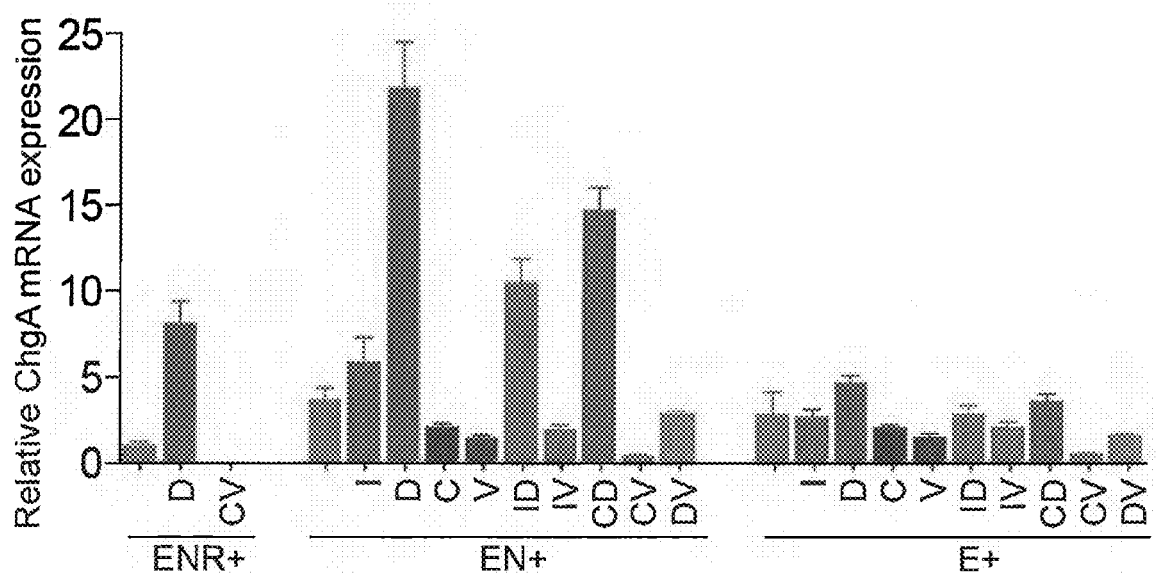
FIG. 2 shows mRNA expression of ChgA in cultured intestinal stem cells.

Screening System for EEC Differentiation (FIG. 2)

To further increase the differentiation efficiency, multiple combinations of growth factors and Wnt/Notch modulators as used in the stem cell expansion and differentiation system were tested to identify a basal combination with the highest differentiation efficiency. The combination of EGF, Noggin, and DAPT (END), but without R-spondin1 or other Wnt activators/inhibitors, induced high levels of ChgA expression, as shown in FIG. 2, where mRNA expression of ChgA was measured for intestinal stem cells cultured under multiple conditions, including growth factors EGF (E), Noggin (N), R-spoindin 1 (R), and differentiation combinations of Wnt activator CHIR99021 (C), VPA, and Wnt inhibitor IWP-2 (I), or Notch inhibitor DAPT (D).

In conclusion, the END condition was used as a basal condition for small molecule screening.

Example 10

Figure 3:
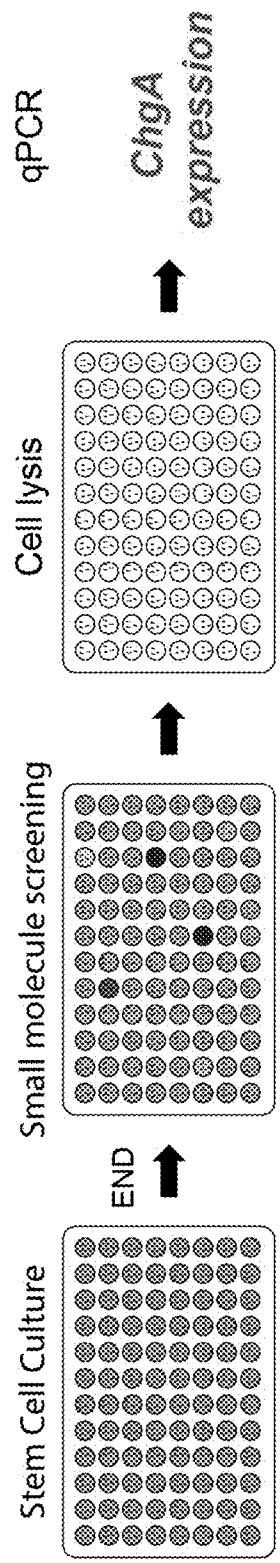
FIG. 3 shows a 96-well screening platform for small molecules that increase EEC differentiation.

96-Well Screening Platform for Small Molecules that Increase EEC Differentiation (FIG. 3)

A 96-well screening system was further employed with qPCR for ChgA expression as an indicator of EEC differentiation for screening small molecule libraries, as shown in FIG. 3, where Lgr5 intestinal stem cells were expanded and passaged into a 96 well plate. Cells were then cultured with EGF, Noggin, and DAPT (END), as well as small molecules. After 2-3 days of differentiation, the cells lysed and ChgA expression was measured by qRT-PCR.

Example 11

Figure 4:
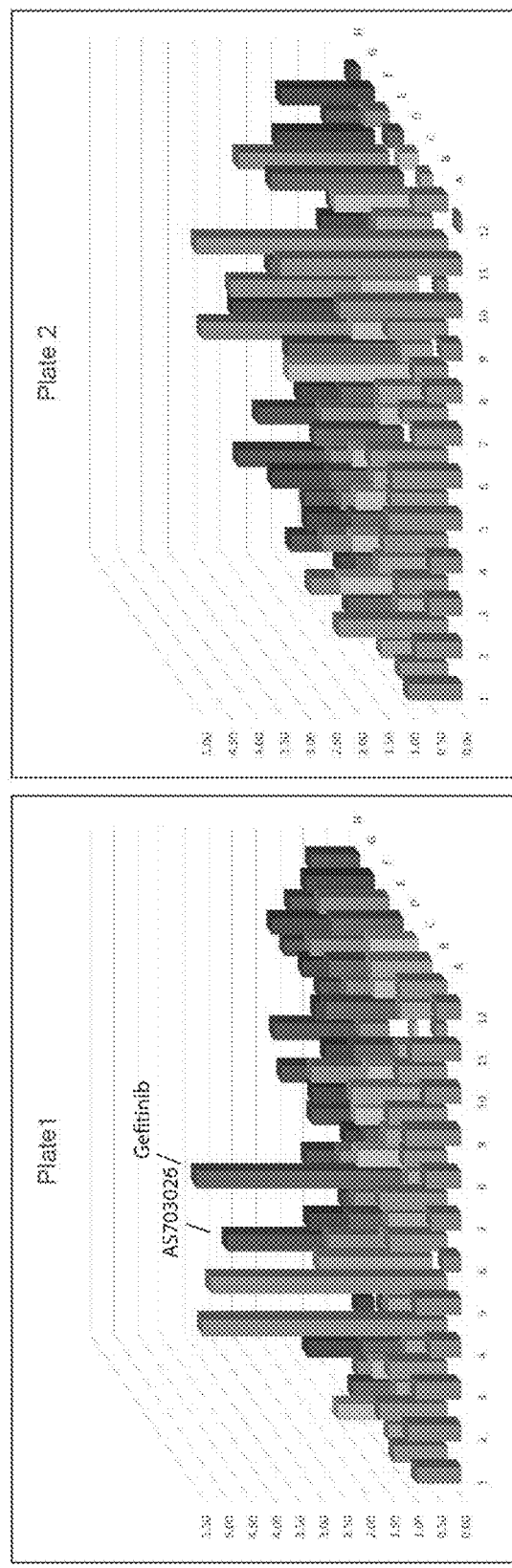
FIG. 4 shows positive hits from small molecules screening results.

Positive Screening Hits (FIG. 4)

Exemplary screening results were recorded, as shown in FIG. 4. The EGFR inhibitor Gefitinib and the MEK/ERK pathway inhibitor AS703026 increased ChgA expression.

Example 12

Figure 5:
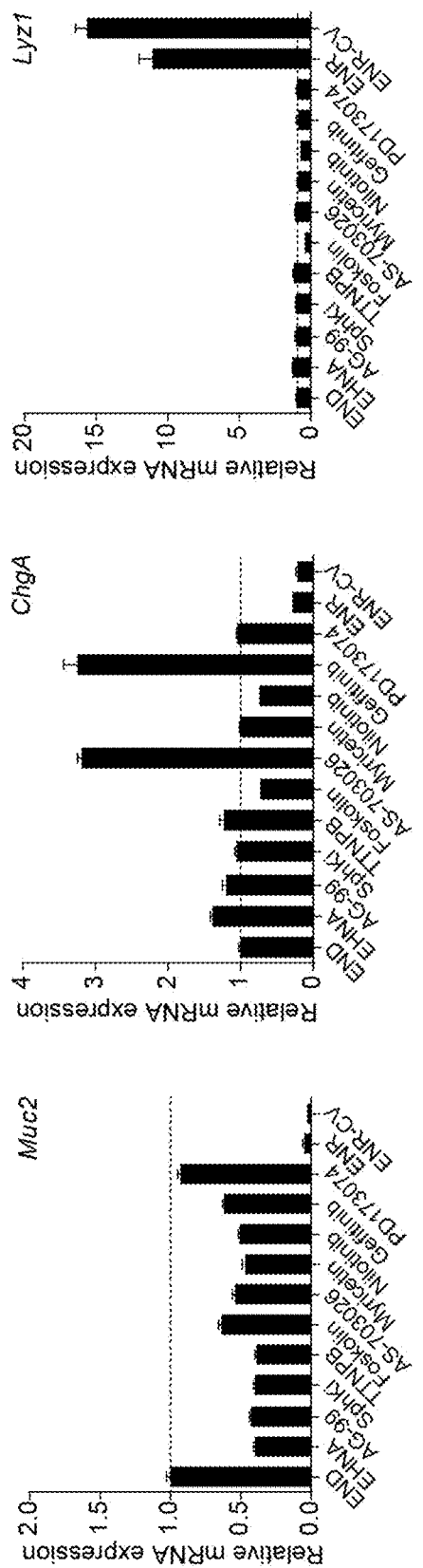
FIG. 5 shows validation of the positive hits using small molecules and intestinal stem cells differentiated under END conditions.

Validation of Positive Hits (FIG. 5)

Small molecules were further validated using a 24-well plate culture and the differentiation system. EGFR inhibitors (e.g., Gefitinib) or MEK/ERK inhibitors (e.g., AS703026 and PD0325901) possessed similar activity in promoting ChgA expression, and the expression of Goblet cell marker (Muc2) and Paneth cell marker (Lyz1) were not similarly increased, suggesting specific induction in the direction of EEC, as shown in FIG. 5, where intestinal stem cells were differentiated under END conditions with the addition of small molecules. The expression of markers of secretory lineage cells including goblet cells (Muc2), enteroendocrine cells (ChgA), and Paneth cells (Lyz1) were measured.

Figure 35:
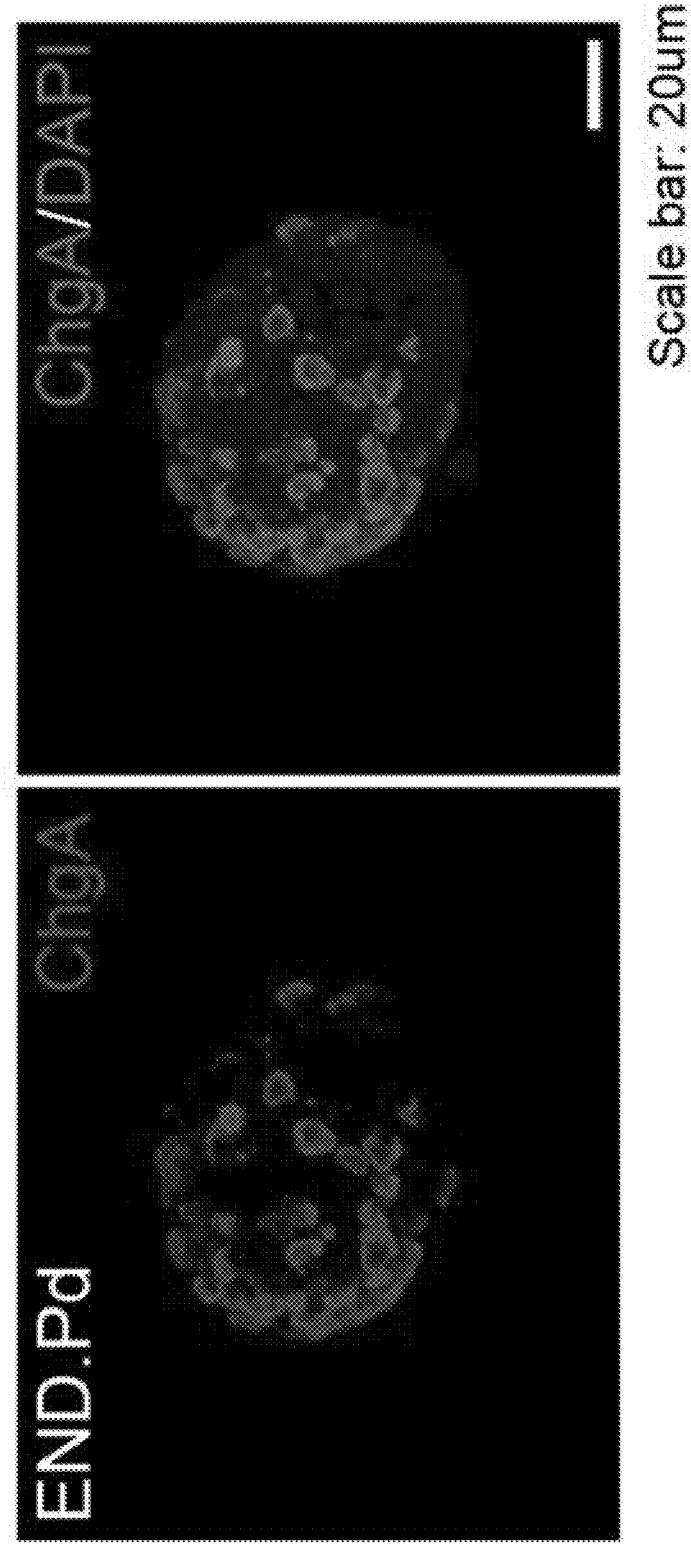
FIG. 35 shows that a combination of Notch and EGFR/MEK/ERK inhibition and Wnt inactivation (by R-Spondin1 withdraw) induces specification of ISCs towards EEC direction as determined by immunostaining against ChgA.
Figure 36:
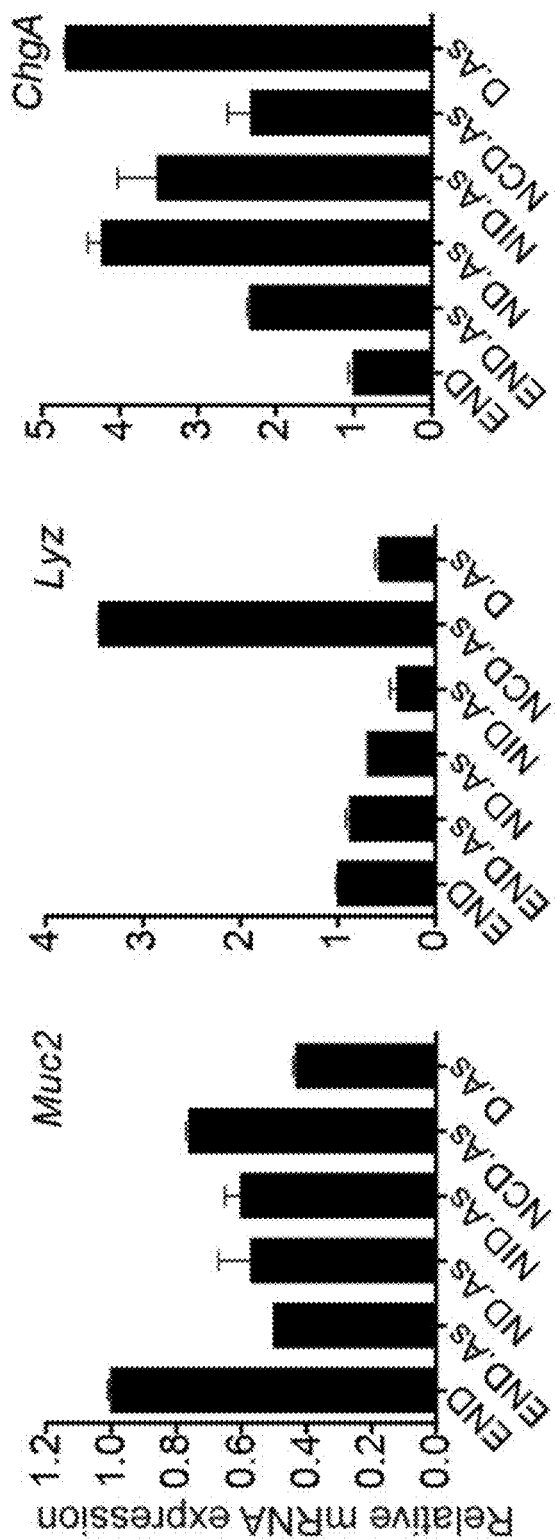
FIG. 36 shows that removing EGF and/or Noggin from the combination induced higher level ChgA expression, while adding the Wnt pathway inhibitor IWP 2 (or I) or GSK3β inhibitor CHIR99021 (or C) did not further increase differentiation towards EEC.
Figure 37:
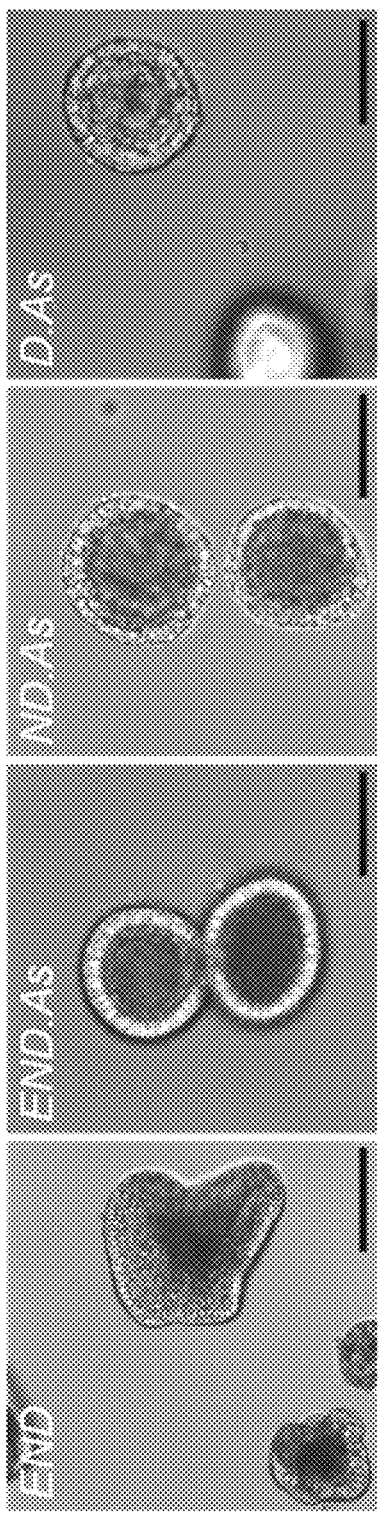
FIG. 37 shows the morphology of cell colonies in multiple differentiation conditions.

EEC generation was also confirmed by immunostaining against ChgA (FIG. 35). In this condition, a combination of Notch and EGFR/MEK/ERK inhibition and Wnt inactivation (by R-Spondin1 withdraw) was used to induce specification of ISCs towards EEC direction. Further removing EGF and/or Noggin from the combination induced higher level ChgA expression (FIG. 36), but a higher cell apoptosis level was observed in these conditions (FIG. 37). Adding the Wnt pathway inhibitor IWP 2 (or I) or GSK3β inhibitor CHIR99021 (or C) did not further increase differentiation towards EEC (FIG. 36).

Example 13

Figure 6:
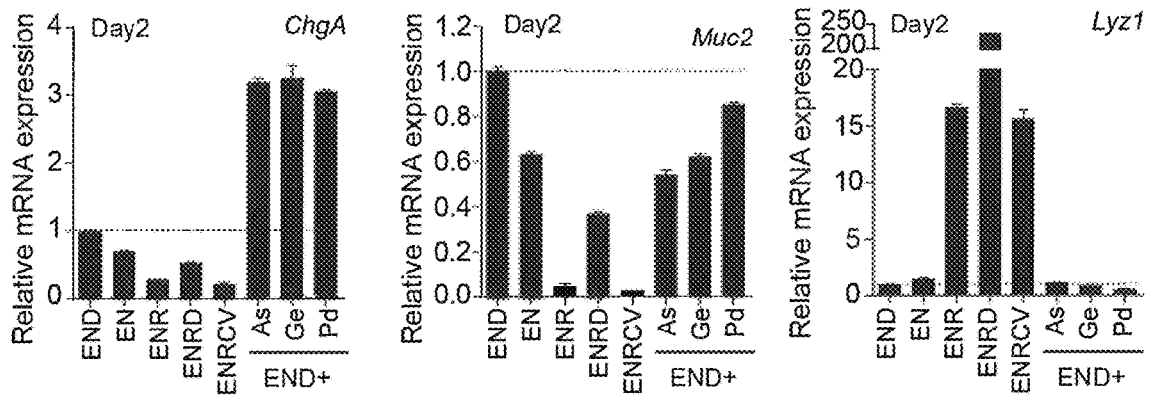
FIG. 6 shows MAPK/ERK or EGFR inhibitors specifically increase EEC differentiation.

MAPK/ERK or EGFR Inhibitors Specifically Increase EEC Differentiation (FIG. 6)

Intestinal stem cells were cultured under multiple conditions, and small molecules AS703026 (As), Gefitinib (Ge) and PD0325901 (Pd) specifically increased the expression of enteroendocrine cell marker ChgA.

Example 14

Figure 7:
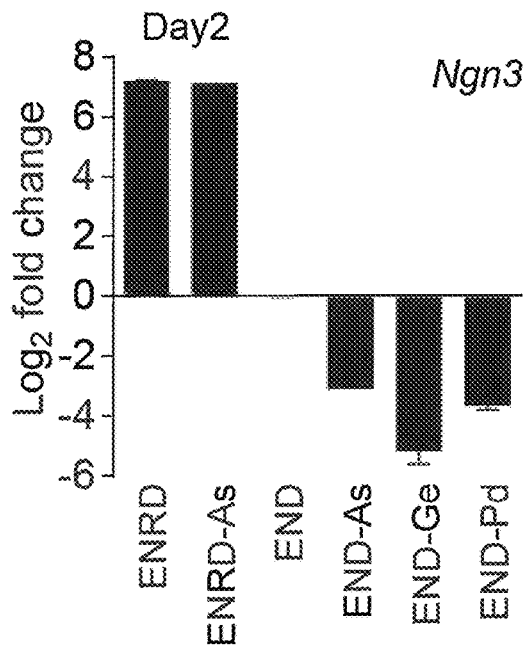
FIG. 7 shows small molecules Gefitinib (Ge), AS703026 (As) or PD0325901 (Pd) decrease Ngn3 expression during EEC differentiation, and that R-Spondin 1 promotes Ngn3 expression.

Small Molecules (e.g., as, Ge, and Pd) Decrease Ngn3 Expression During EEC Differentiation, and R-Spondin1 Promotes Ngn3 Expression (FIG. 7)

During secretory cell differentiation, Ngn3 was shown to be essential for the specification of EECs. There has been prior speculation that Ngn3 positive secretory progenitors differentiate to EECs (Genes Dev. 2002). Examination of Ngn3 expression levels during in vitro differentiation of intestinal stem cells surprisingly revealed that removal of R-spondin1 induced strong reduction of Ngn3 expression, while the addition of Gefitinib (Ge), AS703026 (As), or PD0325901 (Pd) further decreased Ngn3 expression, which was not significant in the presence of R-Spondin 1, as shown in FIG. 7, where intestinal stem cells were cultured for 2 days under multiple conditions, and the mRNA levels of Ngn3 were measured.

Example 15

Figure 8:
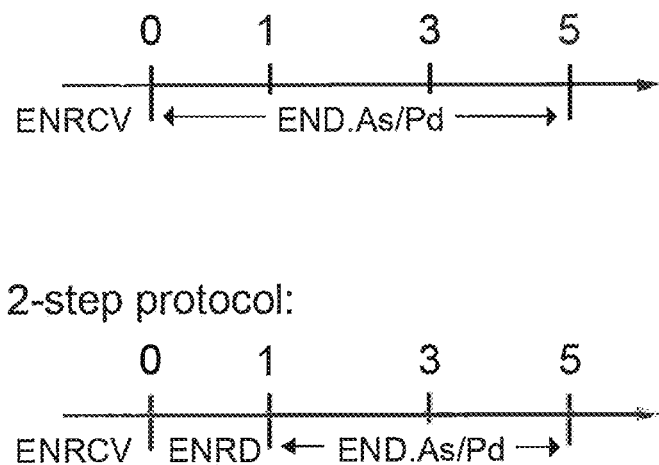
FIG. 8 shows an optimized differentiation protocol.

Optimized Differentiation Protocol (FIG. 8)

While Wnt signaling (under the provision of R-Spondin1) encourages initial specification of EECs to promote Ngn3 expression, Ngn3 expression is subsequently downregulated thereafter during the maturation of EECs. This is consistent with the transit expression of Ngn3 during EEC specification (Genes Dev. 2002). Thus, a 2-step differentiation protocol was tested aiming to increase Ngn3 expression and subsequent EEC differentiation. An initial (first) prime step with R-Spondin 1 and Notch inhibitor DAPT was added to permit the upregulation of Ngn3, followed by a second step without Wnt activation and with small molecules (e.g., Pd) to allow terminal differentiation of EECs, as shown in FIG. 8, where an initial step with the presence of R-spondin1 was added to the differentiation protocol to increase Ngn3 expression in step 1.

Example 16

Figure 9:
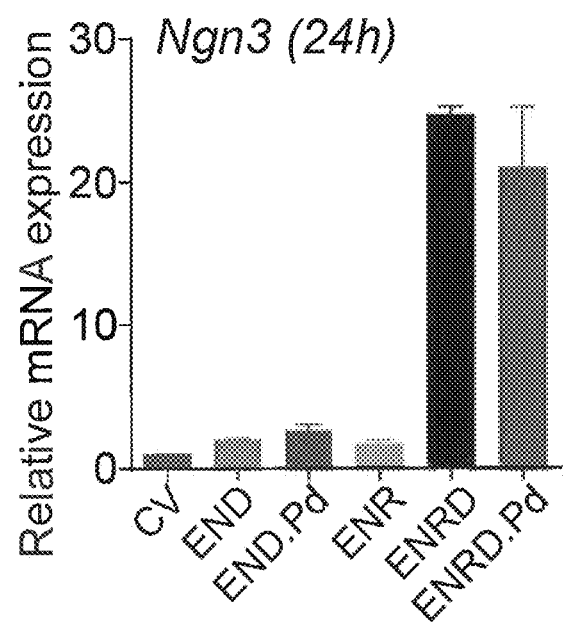
FIG. 9 shows Ngn3 expression at 24 h during EEC differentiation.

Ngn3 Expression at 24 h During EEC Differentiation (FIG. 9)

Ngn3 expression was measured after 24 hours under multiple conditions. In the presence of R-spondin1 and Notch inhibitor DAPT, Ngn3 expression was greatly induced, as shown in FIG. 9, where the combination of R-Spondin 1 and Notch inhibitor DAPT increased Ngn3 expression.

Example 17

Figure 10:
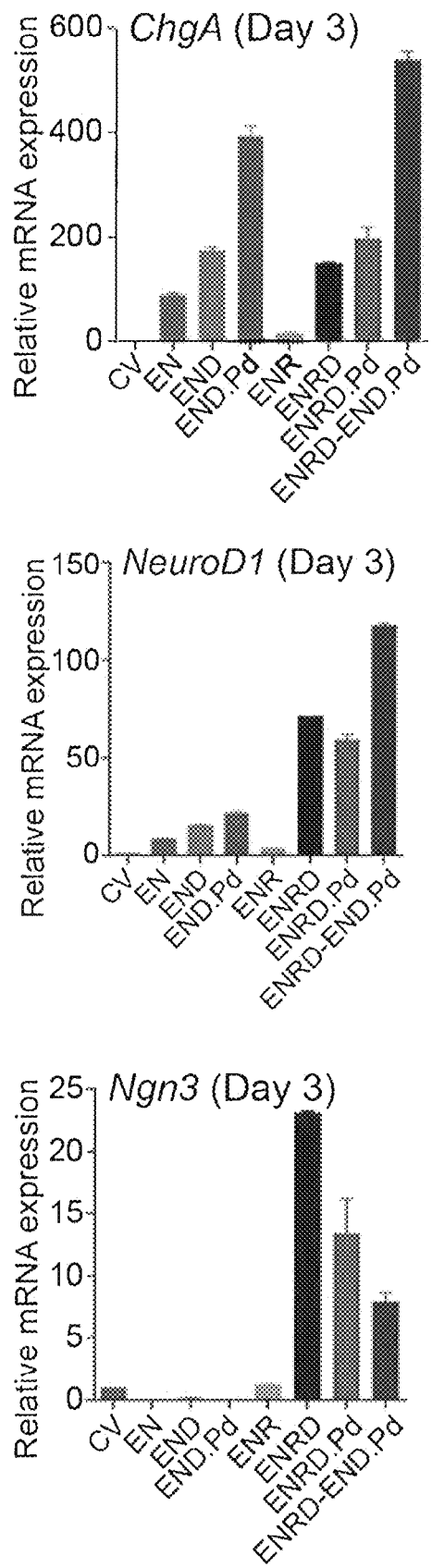
FIG. 10 shows expression of key markers of EEC during differentiation at day 3.

Expression of Key Markers of EEC During Differentiation at Day 3 (FIG. 10)

Switching of the culture media to conditions without Wnt agonist or R-Spondin 1 and with Pd for an additional 2 days showed the Ngn3 expression level was decreased and the ChgA expression was upregulated compared to conditions with R-spondin1 or without Pd, as shown in FIG. 10, where the 2-step differentiation protocol decreased Ngn3 expression and increased ChgA expression at Day 3. The late stage EEC marker NeuroD1 was also increased, further shown in FIG. 10.

Example 18

Figure 11:
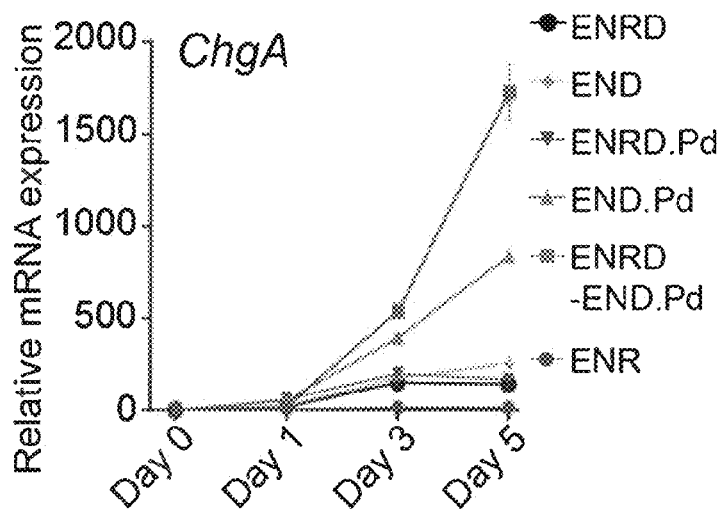
FIG. 11 shows a time course study of key genes during EEC differentiation.
Figure 11:
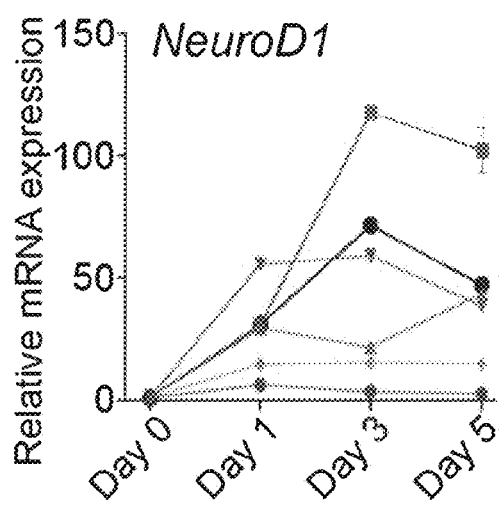
Figure 11:
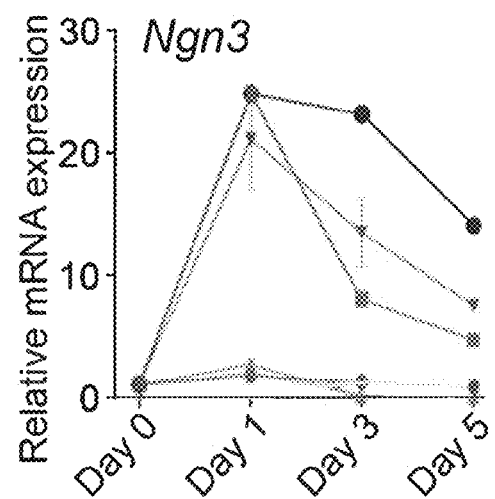
Figure 12:
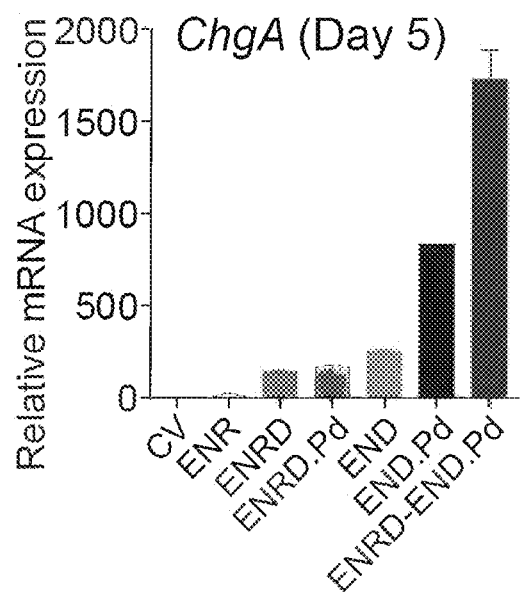
FIG. 12 shows a 2-step protocol with increased EEC marker ChgA expression after 5 days differentiation.
Figure 13:
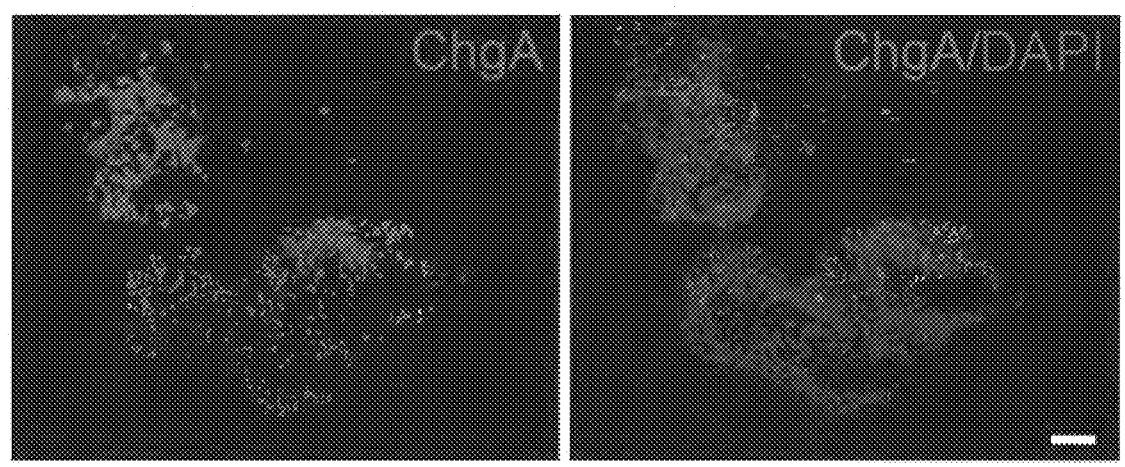
FIG. 13 shows a 2-step protocol with increased EEC differentiation by staining EEC marker ChgA following 5 days differentiation. Scale bar: 50 μm.

Time Course Study of Key Genes During EEC Differentiation (FIGS. 11, 12 and 13)

Figure 38:
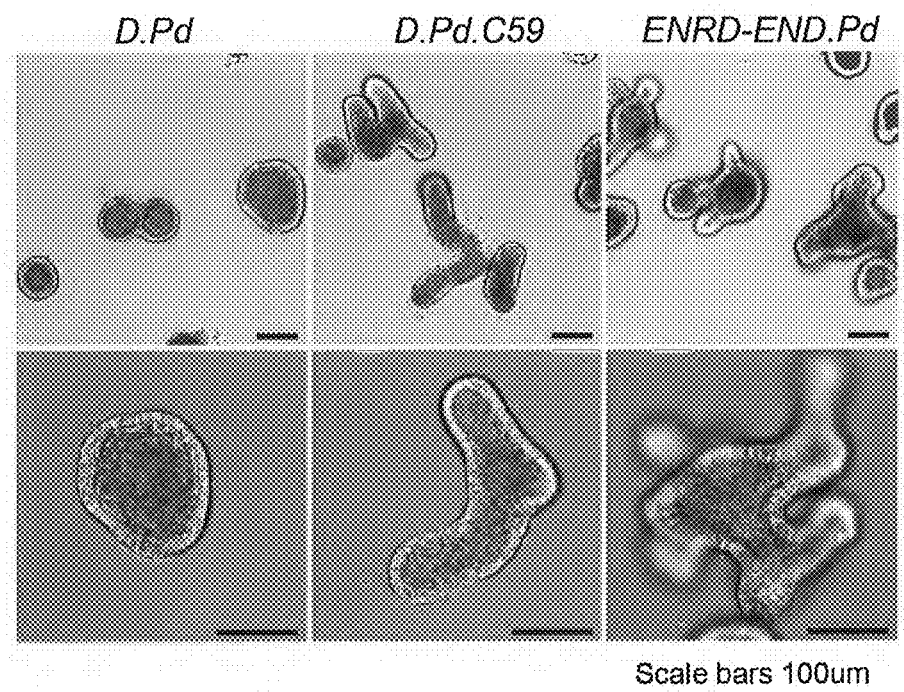
FIG. 38 shows the morphology of cell colonies in multiple differentiation conditions. Note the prominent lumen of colonies with dead cells in conditions of Notch, MEK inhibition and Wnt inactivation (D.Pd condition) as well as Notch/MEK/Wnt inhibition (D.Pd.C59 condition). While 2-step differentiation condition (ENRD-END.Pd) induced less cell death.

A time course study of EEC marker expression suggested the 2-step differentiation protocol effectively increased Ngn3 levels in the first step and decreased Ngn3 and increased ChgA levels during the 2nd step. NeuroD1 showed an intermediate change trend compared with Ngn3 and ChgA, suggesting NeuroD1 expressed after Ngn3, but before ChgA. The 2-step protocol induced highest ChgA expression following 5 days of treatment, as shown in FIG. 11, and effectively induced EEC differentiation from ISCs, as shown in FIG. 12 (2-step protocol increased EEC marker ChgA expression after 5 days differentiation) and FIG. 13 (2-Step protocol increased EEC differentiation by staining EEC marker ChgA following 5 days differentiation), with less cell apoptosis (FIG. 38) than direct Wnt, Notch and MEK/ERK inactivation (D.Pd or D.Pd. C59 condition).

Example 19

Figure 14:
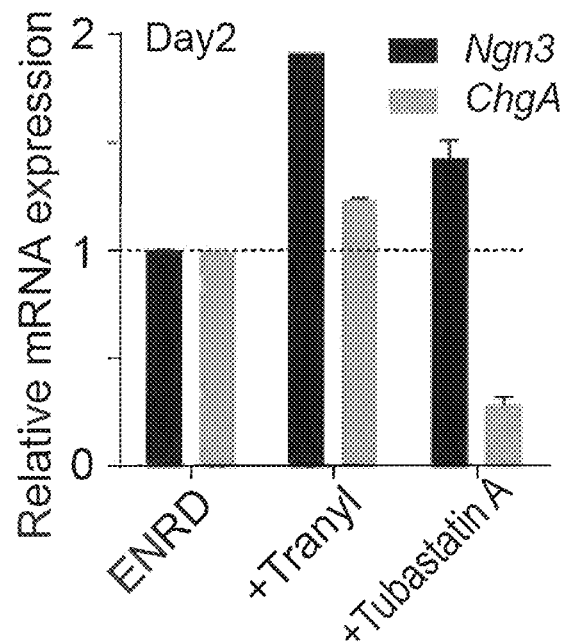
FIG. 14 shows improvement of the differentiation protocol by additional small molecules.

Further Improvement of Differentiation Protocol by Additional Small Molecules (FIG. 14)

In an effort to increase Ngn3 levels during the first step for promotion of differentiation of EEC, factors that increased Ngn3 expression were identified via additional screening under ENRD conditions. More than 80 small molecules and growth factors were screened, and Tubastatin A and Tranylcypromine were found to increase Ngn3 expression, as shown in FIG. 14, where following 2 days of differentiation, Tranylcypromine (Tranyl) increased both Ngn3 and ChgA levels, while Tubastatin A increased Ngn3 levels, but decreased ChgA levels. However, while Tranylcypromine also increased ChgA expression, it was noted that Tubastatin A decreased ChgA expression (also shown in FIG. 14).

Example 20

Figure 15:
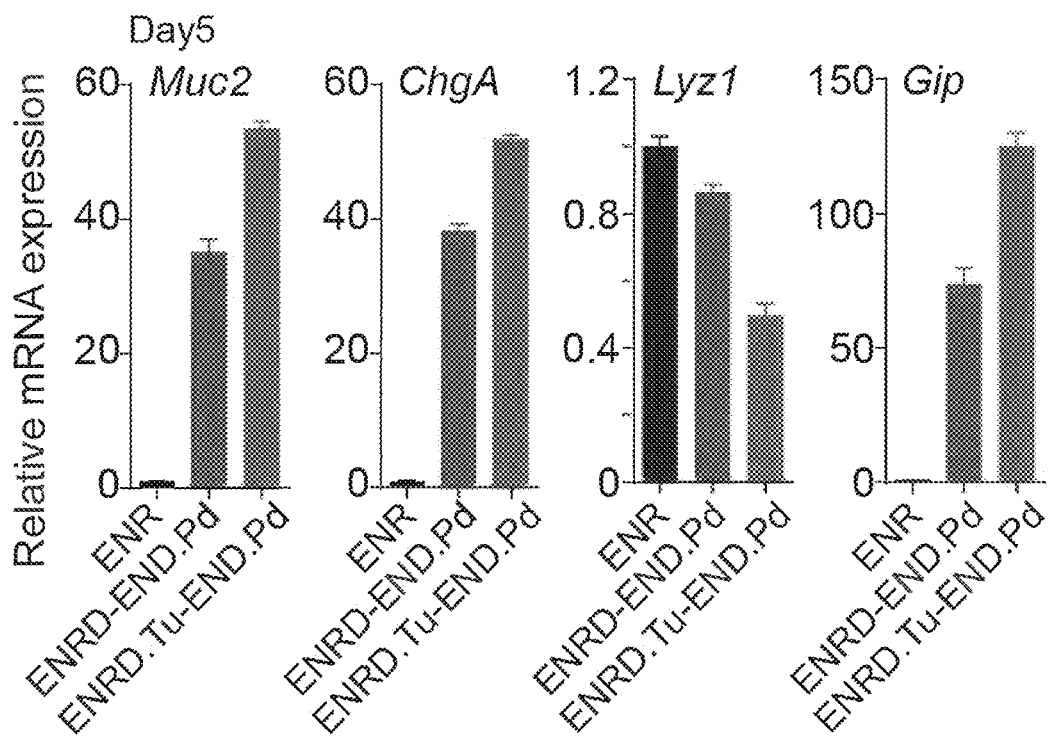
FIG. 15 shows Tubastatin A (Tu) increases EEC differentiation when added in Step 1 of the differentiation protocol.

Tubastatin A (Tu) Increases EEC Differentiation when Added in Step 1 of the Differentiation Protocol (FIG. 15)

Figure 39A:
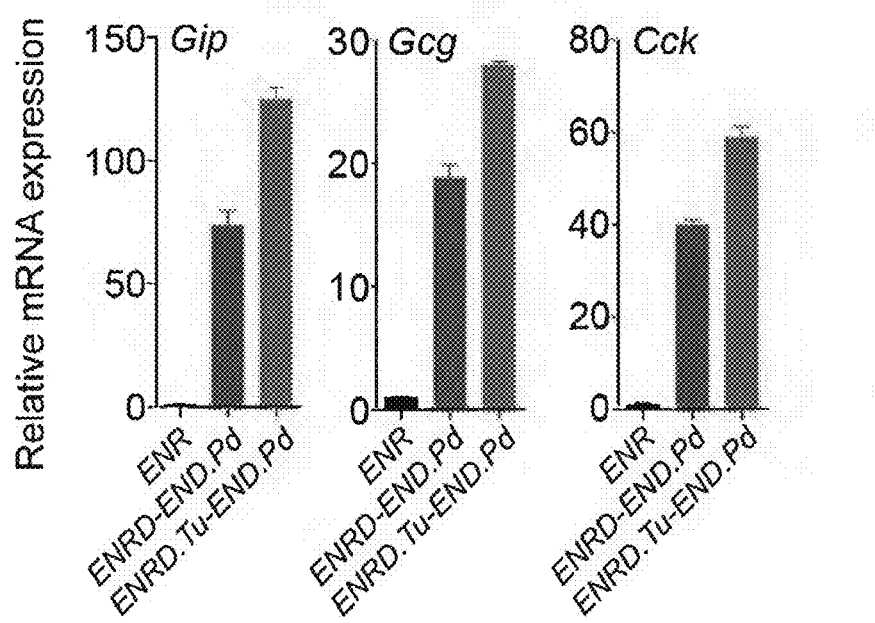
FIGS. 39A-39E show that additional small molecules increase EEC differentiation.
Figure 39B:
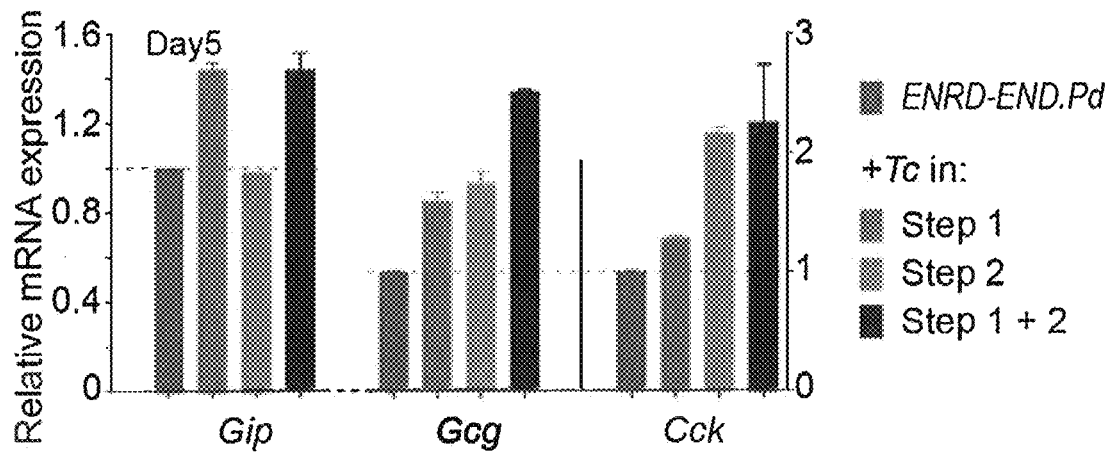
Figure 39C:
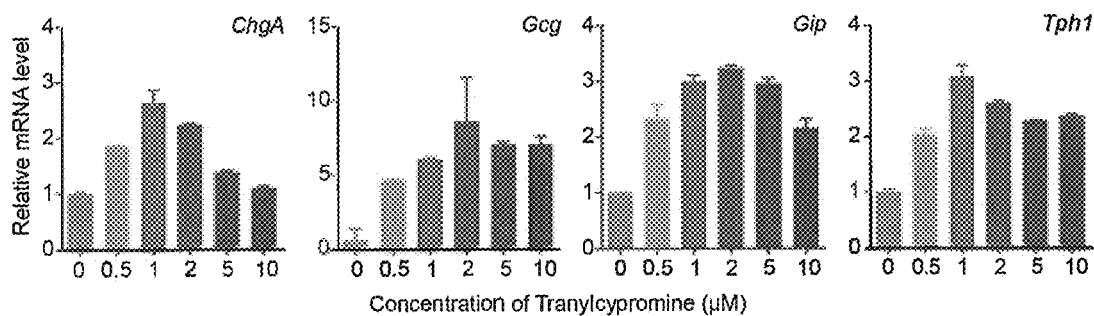

Tubastatin A was applied in step 1, but Tranylcypromine was applied in both steps during the differentiation. Under these conditions, both compounds increased EEC marker ChgA expression following 5 days of the 2-step differentiation protocol, and the expression of markers for K cell (Gip), L cell (Gcg), and I cell (Cck) were also increased, as shown in FIG. 15 with mRNA expression of markers for cells including goblet cells (Muc2), enteroendocrine cells (ChgA), Paneth cells (Lyz1) and K-cells (Gip); and as shown in FIG. 16 with mRNA expression of markers of multiple cell types including goblet cells (Muc2), enteroendocrine cells (ChgA), Paneth cells (Lyz1), K-cells (Gip), L-cells (Gcg) and I-cells (Cck); and as shown in FIGS. 39A-39C.

Figure 16:
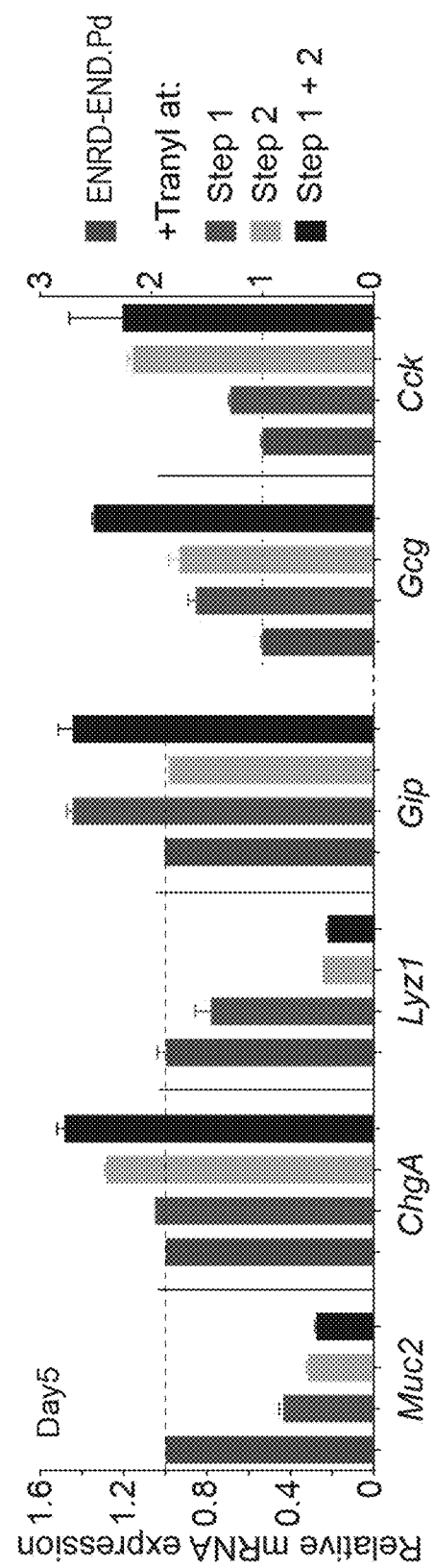
FIG. 16 shows Tranylcypromine increased EEC differentiation when added at both steps in differentiation.

It is worth noting that the addition of Tranylcypromine also significantly decreased the expression of Goblet cell (Muc2) and Paneth cell (Lyz1) markers, suggesting specific induction of EEC differentiation, further indicated in FIG. 16.

Example 21

Figure 17:
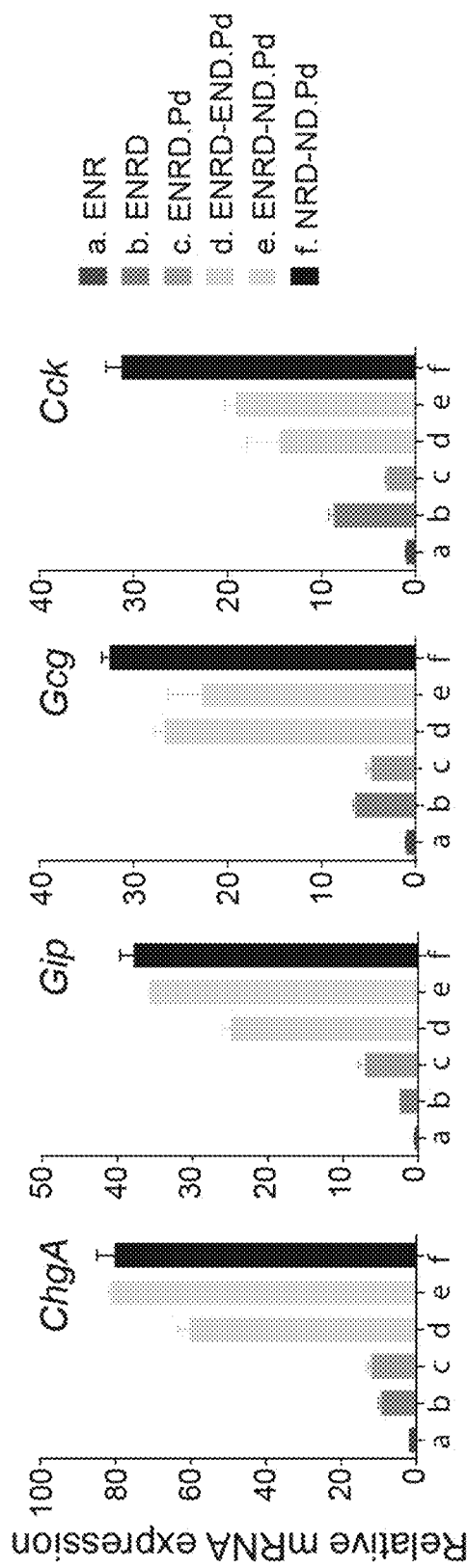
FIG. 17 shows that removal of EGF further increased differentiation of EEC.

Removing EGF Further Increased Differentiation of EEC (FIG. 17)

Figure 39D:
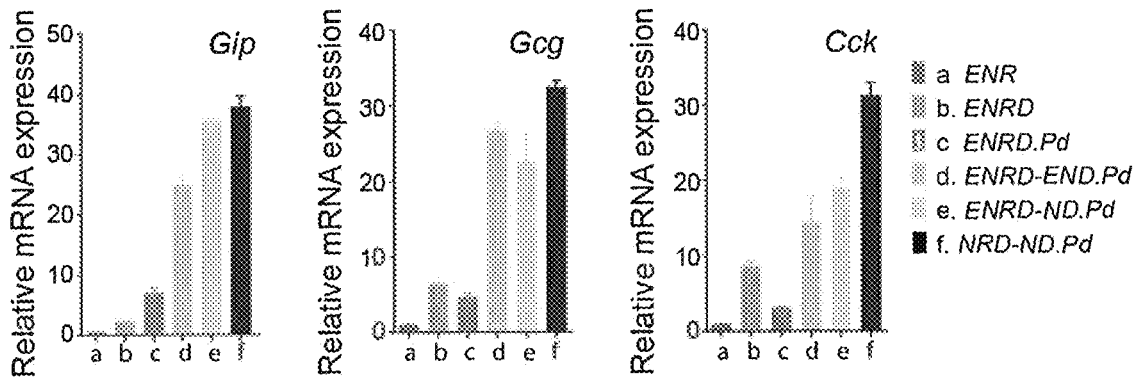

In addition, as Pd/As targets the MEK/ERK pathway, which is one of the downstream targets of the EGF pathway, the effect of EGF was tested in the differentiation. Removing EGF from the media further increased EEC marker (viz., ChgA, Gip, Gcg, and CCK) expression, as shown in FIG. 17 and FIG. 39D, where intestinal stem cells were differentiated in multiple conditions for 5 days and markers for enteroendocrine cells such as ChgA, Gip, Gcg and Cck were measured by qPCR, but there tended to be more dead cells in the lumen of the differentiated cell colony when EGF was removed in both steps, likely due to EGF's role in promoting cell survival (e.g., PI3K). Therefore, EGF was kept in the first step of the differentiation process. The effect of Noggin in step 2 was marginal thus it was removed from the composition.

Example 22

Figure 18:
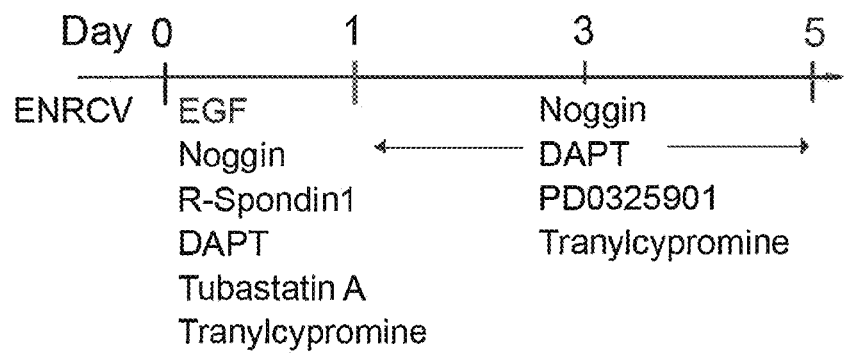
FIG. 18 shows an improved differentiation protocol.

Improved Differentiation Protocol (FIG. 18)

To characterize EECs generated from intestinal stem cells, the cells were differentiated using the conditions identified and shown in FIG. 18.

Example 23

Figure 19:
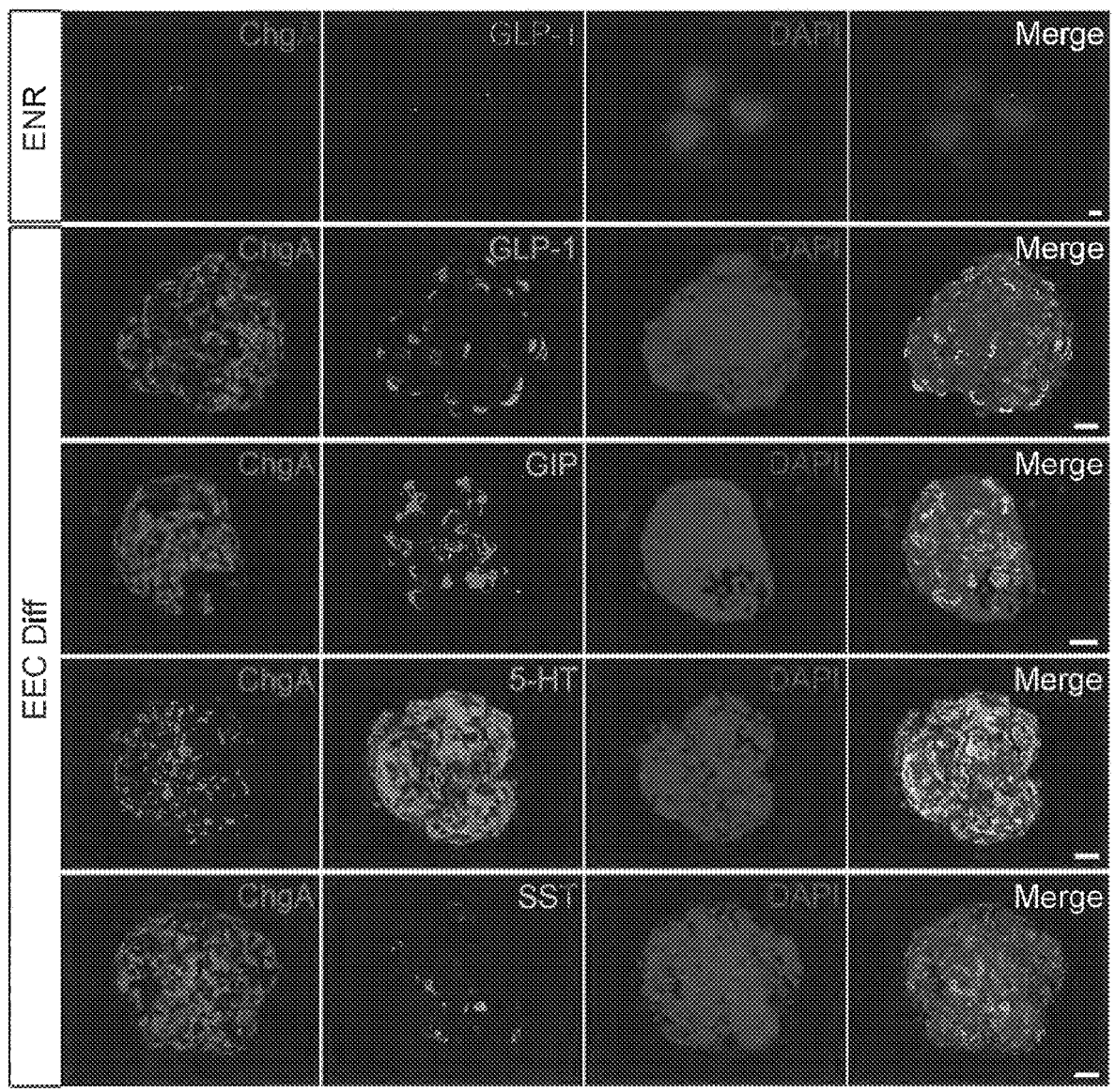
FIG. 19 shows highly efficient EEC differentiation from ISC. Scale bars: 20 μm.

Highly Efficient EEC Differentiation from ISC (FIG. 19)

Figure 20:
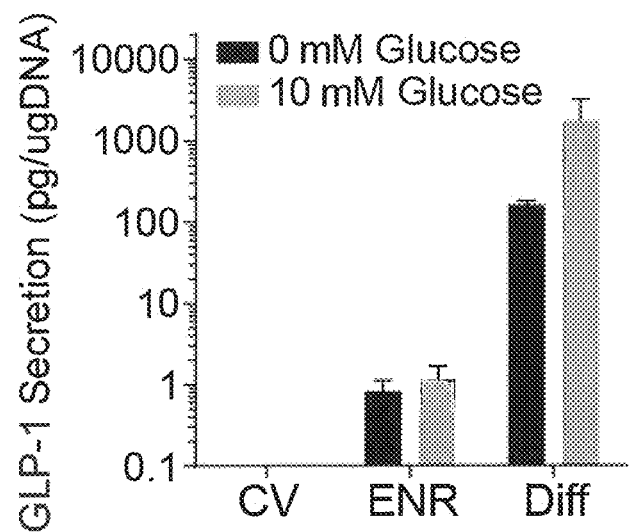
FIG. 20 shows functional L cells (GLP-1) generated from ISC.

Immunofluorescence staining was performed against markers for EECs. In intestinal organoid culture (ENR conditions), only very few cells differentiated to EECs, indicated by the number of ChgA+ or GLP-1+ cells in the organoids, as shown in FIG. 19, top panel, where ISCs were expanded under ENRCV conditions and further differentiated in conditions, as indicated. Immunostaining against markers for enteroendocrine cells (e.g., ChgA) or multiple subtypes of EEC were also performed. DAPI was used for nucleus staining. These findings were consistent with previous reports (Diabetes, 2014). Under controlled differentiation conditions, most of the cells turned to EECs following a 5 day differentiation protocol, and the generation of EEC subtypes was also elevated (see FIG. 19). Interestingly, most of the EECs appear to be serotonin secreting cells, indicated by strong 5-HT staining (see FIG. 19). GLP-1 release from differentiated L cells was further tested. Other EEC subtypes also existed at higher frequency, as identified by positive staining of markers such as GLP-1, GIP, and SST. The differentiation protocol significantly increased GLP-1 secretion from the organoids, and 10 mM glucose stimulation induced a 5-fold increase of GLP-1 secretion, as shown in FIG. 20 (Functional L cell (GLP-1) generated from ISC), where secretion of GLP-1 was measured in cells cultured in conditions, as indicated, and suggesting that these EECs were mature and functional (FIG. 40C).

Figure 39E:
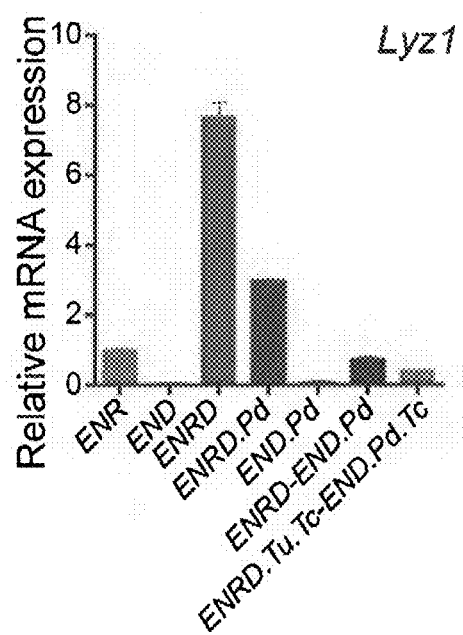
Figure 40A:
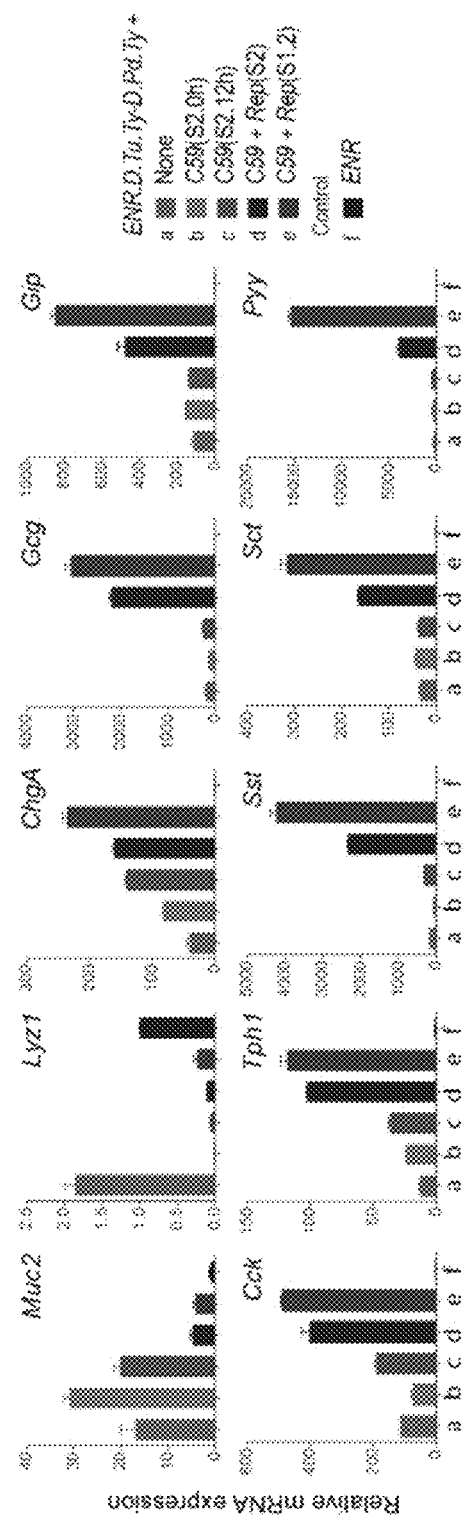
FIGS. 40A-40E show that protocol optimization results in high efficient differentiation of EECs from ISCs.
Figure 40B:
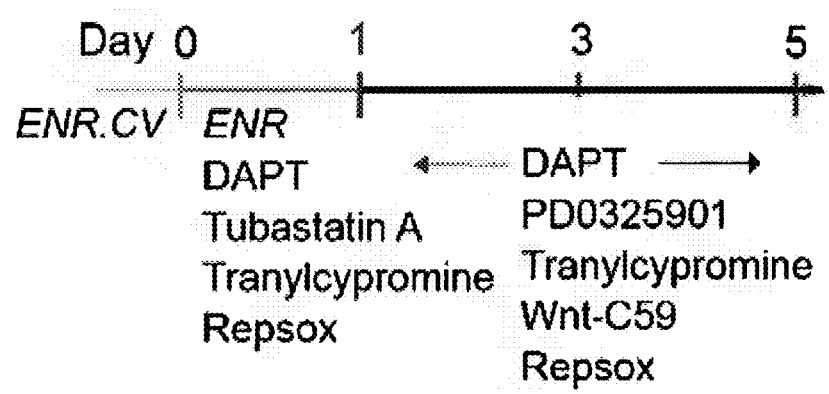
Figure 41A:
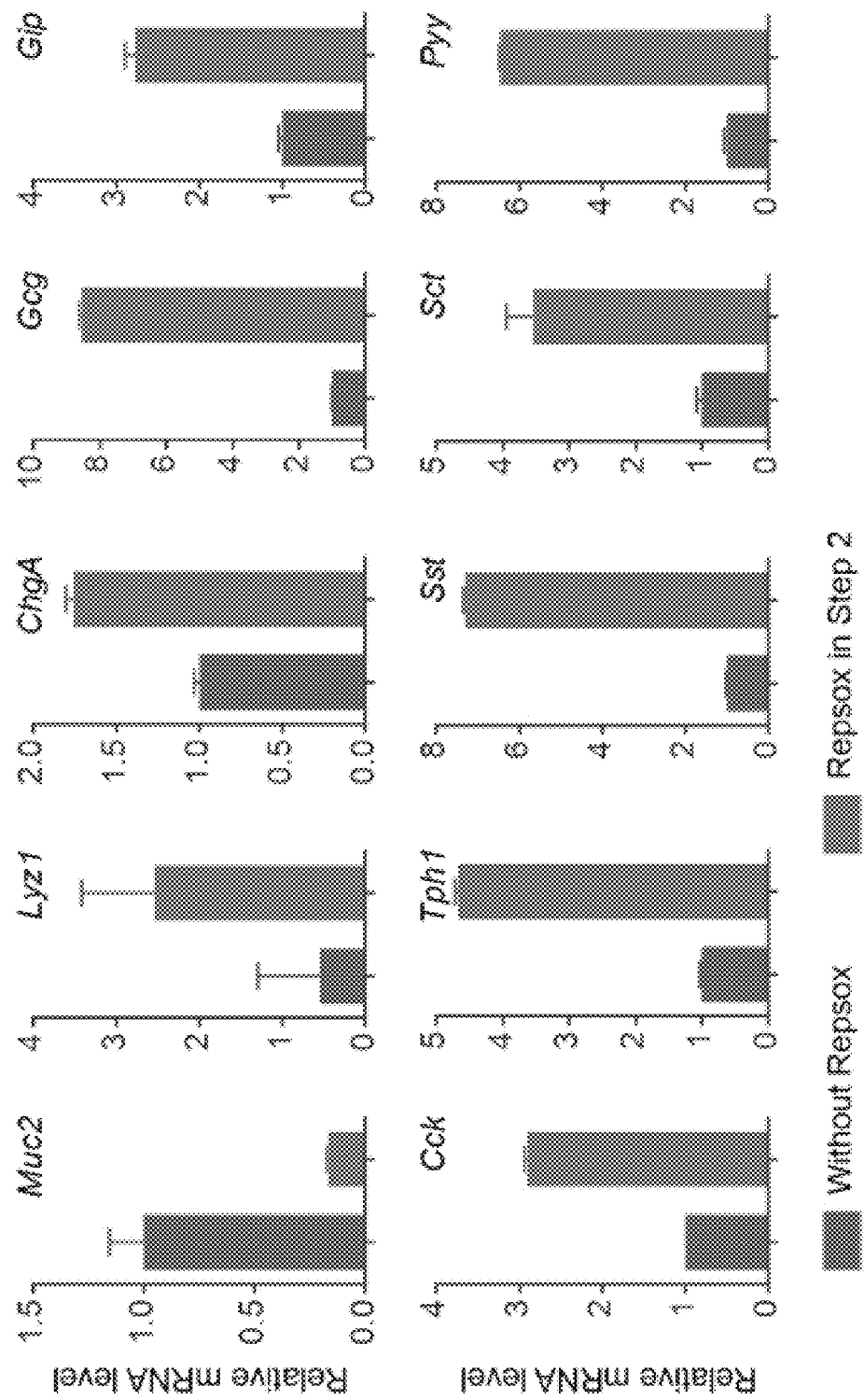
FIGS. 41A-41C show that protocol optimization results in high efficient differentiation of EECs from ISCs.
Figure 41B:
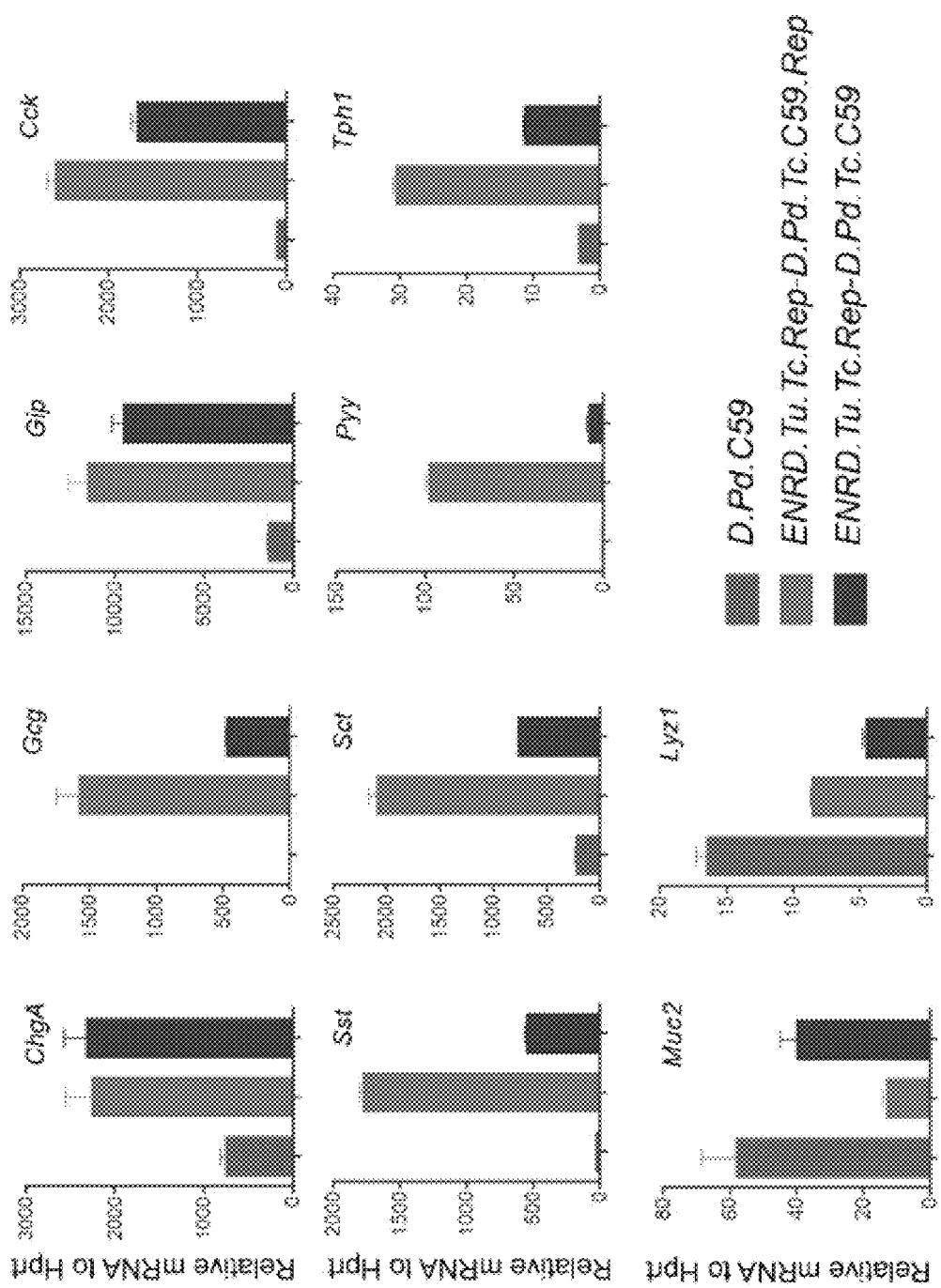
Figure 41C:
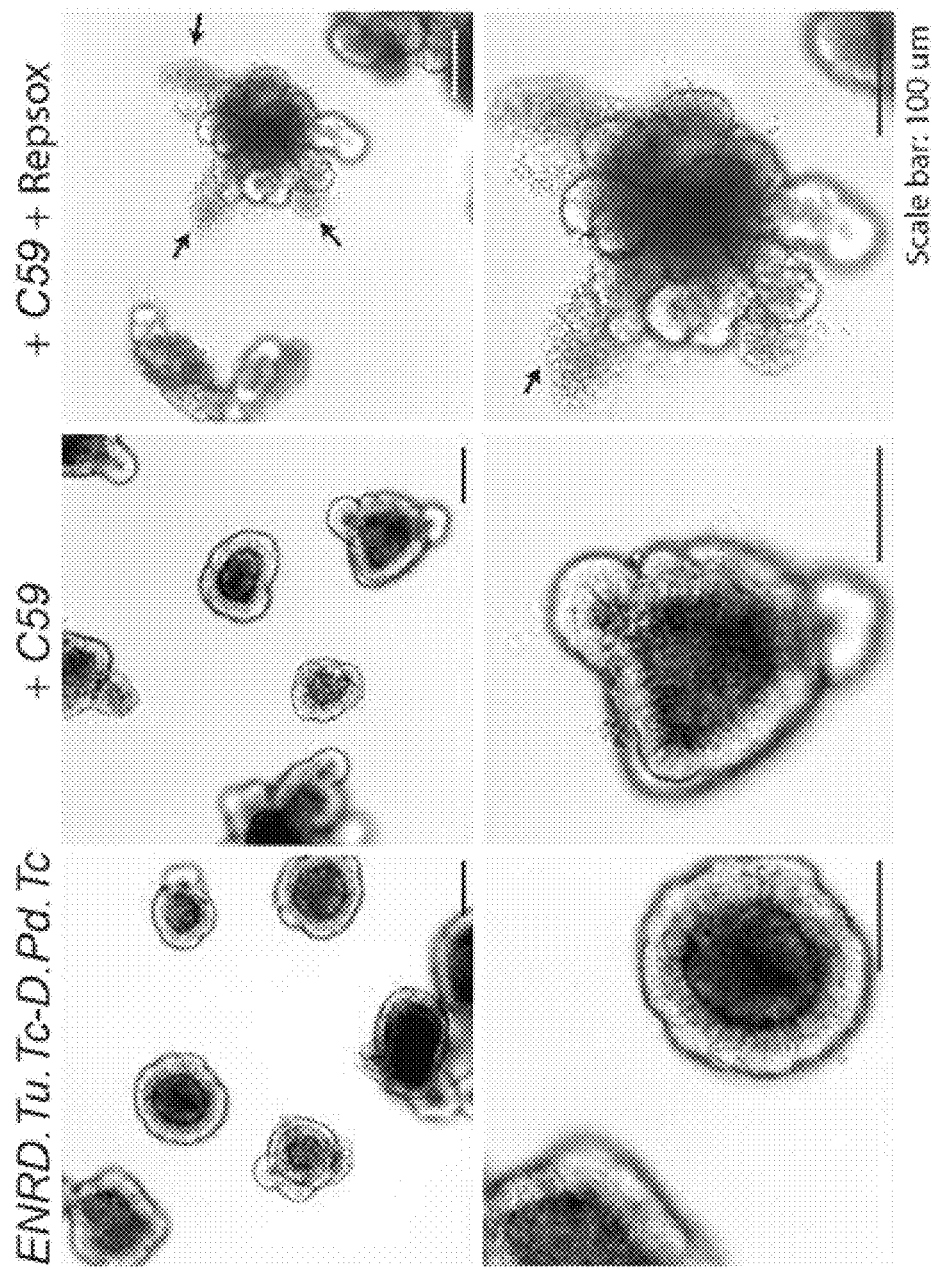

In EEC differentiation, Wnt signaling activity is required in the first step of induction, while not necessary in the second step of EEC specification. In the 2-step differentiation protocol described herein, although the 1st step with Wnt activation increased Ngn3 expression, it also induced Paneth cell differentiation, which further may secret Wnt ligand and activate Wnt pathway in step 2. This is consistent with higher level of Paneth cell marker Lyz1 expression comparing with the END.Pd condition, where the initial Wnt inactivation step prevented the generation of Paneth cell in the first place (FIG. 39E). Thus, inhibiting Wnt signaling with a small molecule inhibitor (Wnt-C59 or C59) in step 2 was tested. C59 effectively decreased Paneth cell marker Lyz1 expression suggesting it prevented Paneth cell differentiation in step 2. And it further increased ChgA expression indicating higher level of EEC differentiation (FIG. 40A). Delayed addition of C59 for 12-24 hours in step 2 further increases ChgA expression possibility due to higher level of Ngn3 induction in step 1 (FIG. 40A). Similarly, addition of Tgf-inhibitor (Repsox, Rep) greatly promoted ChgA expression and decreased goblet cell marker Muc2 expression (FIG. 40A, FIG. 41A). Rep also greatly increased the expression of mature EEC markers (Gcg, Gip, Cck, Tph1, Sst, Sct, Pyy), in a range of 120× (Tph1), 300× (Sct), 430× (Cck), 800× (Gip), up to 15,000× (Pyy) over the expression level in the ENR condition. It was found that adding Repsox in step 1 is sufficient to induce comparable level of ChgA with adding it in both steps, but the expression of mature EEC markers was greatly reduced (FIG. 41B), suggesting Tgf-β inhibition induces both EEC specification and further maturation. Interestingly, the addition of Repsox induce the colonies to expel apoptotic cells from the lumen (FIG. 41C), and form high purity EEC cell colonies.

Figure 40C:
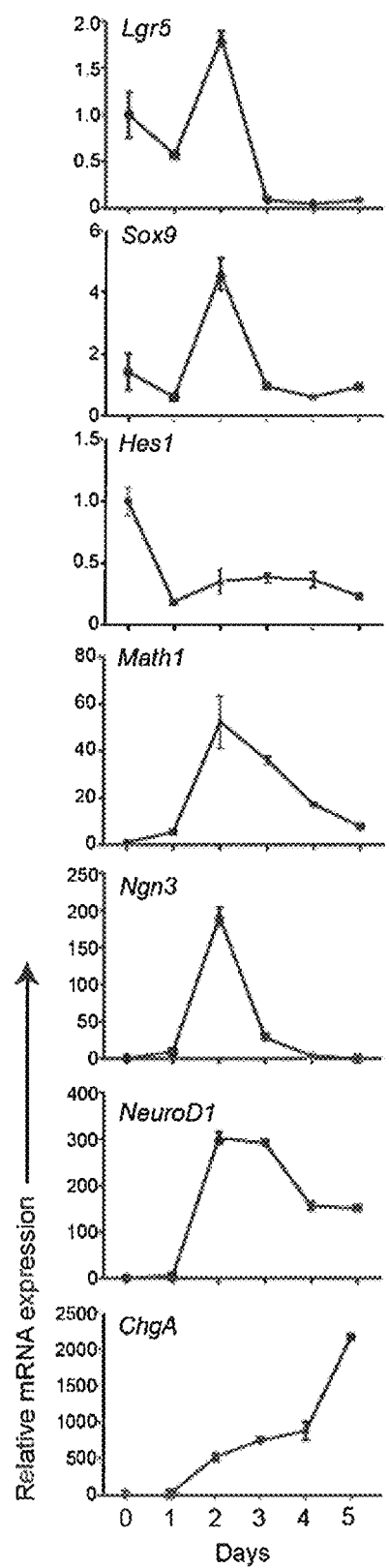
Figure 40D:
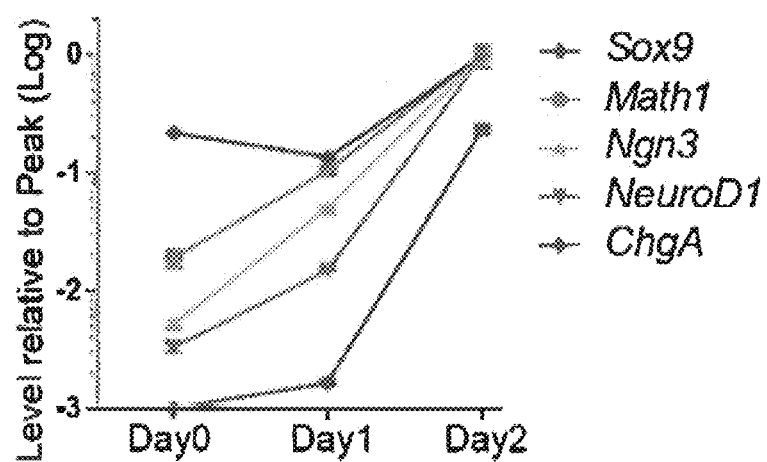

Using the optimized differentiation (FIG. 40B), the change in expression of key differentiation genes during the differentiation process was tested (FIG. 40C). The stem cell gene Lgr5 was slightly upregulated at day 2 likely due to increase in Paneth cell differentiation or Notch downregulation (Tian et al., 2015). Sox9 expression was implicated in the regulation of ISC and EEC differentiation (Formeister et al., 2009), and plays an important role in pancreas endocrine cell differentiation, partially by induction of Ngn3 expression. It was found that Sox9 was initially upregulated and then downregulated starting from day 2, which showed a similar expression pattern as Lgr5. Sox9 expression was maintained at a relatively high level compare with Lgr5, consistent with its expression in EECs (Formeister et al., 2009). The expression of Hes1, which is a downstream gene of activated Notch signaling, was downregulated. The expression of multiple Notch target genes was similarly regulated, including Math1/Atoh1, Ngn3, and NeuroD1, which included an initial upregulation phase and then a downregulation phase. And the expression of ChgA continuously increased, consistent with gradually increased EEC differentiation. Interestingly, the upregulation rates of these genes to reach peak levels (day 2 for Sox9, Math1, Ngn3, NeuroD1 and day 5 for ChgA) were different, with the order of Sox9, Math1, Ngn3, NeuroD1, and ChgA (FIG. 40D). This likely reflects the natural gene regulation process of these genes.

Figure 40E:
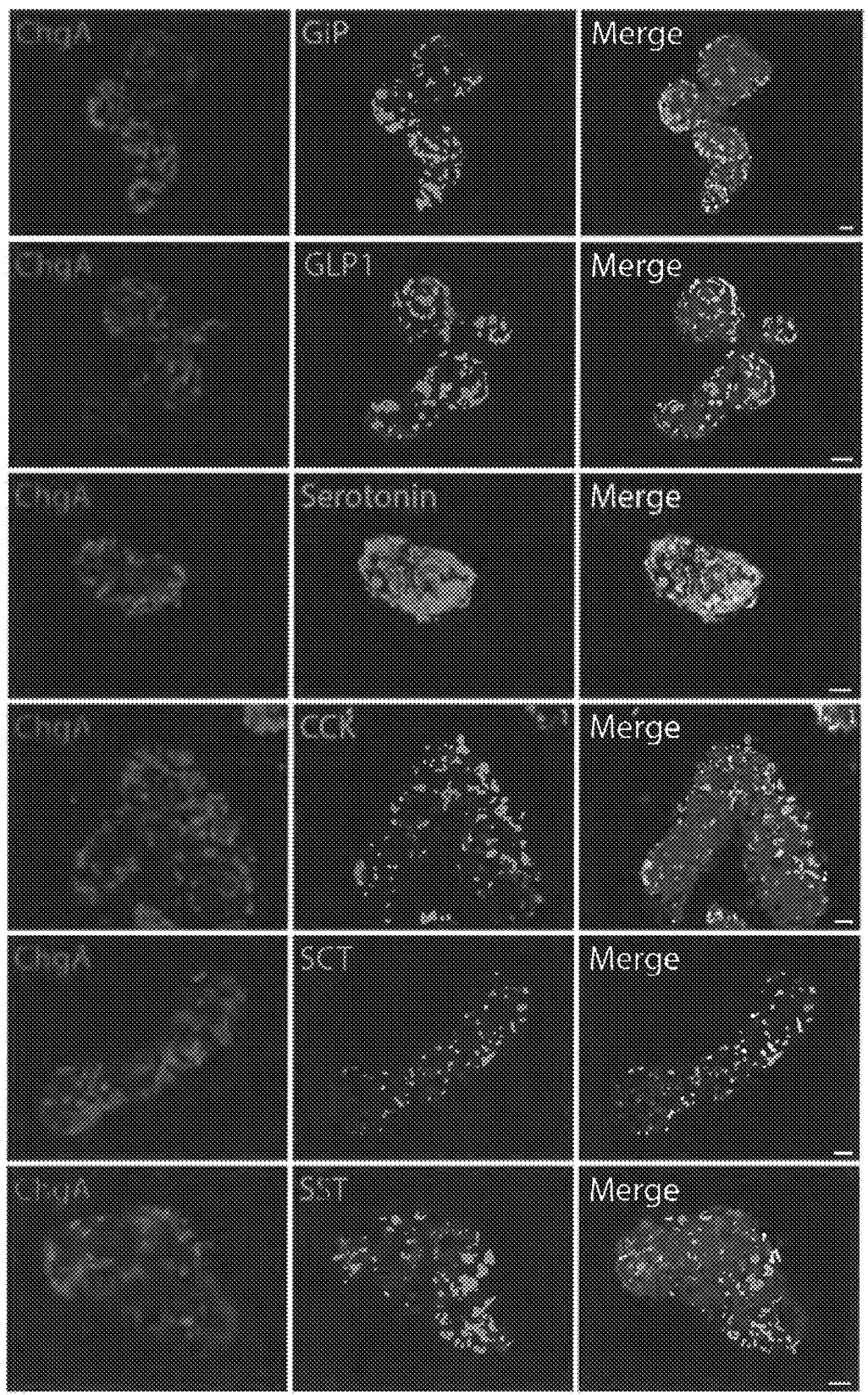

Immunofluorescence staining was performed to identify different EEC subtypes generated in our cultures. A high frequency of multiple EEC subtypes was found to exist in the colonies, identified by positive staining for GIP, GLP1, Serotonin, CCK, SCT and SST (FIG. 40E). Interestingly, it was found that 2 populations of ChgA positive cells in the differentiated EEC colonies, where a ChgA highly expressed population colocalize with serotonin expressing cells, and a ChgA low population colocalize with GLP-1, GIP, CCK, SST, and SCT expressing cells (FIG. 40E).

Example 24

Figure 21:
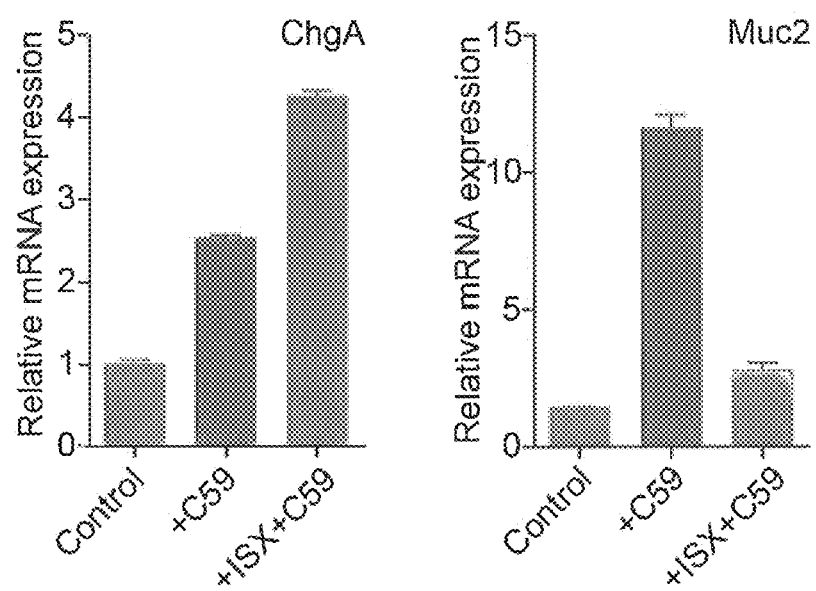
FIG. 21 shows additional factors, including Wnt-C59 and ISX-9 and their combination, increase EEC differentiation.

Additional Factors Increase EEC Differentiation (FIG. 21)

Additional molecules were identified that can further increase EEC differentiation, as shown in FIG. 21, where small molecules including Wnt-C59 and ISX-9 and their combination further increased ChgA expression of the differentiated cells. Control: previous differentiation conditions.

Example 25

Figure 22:
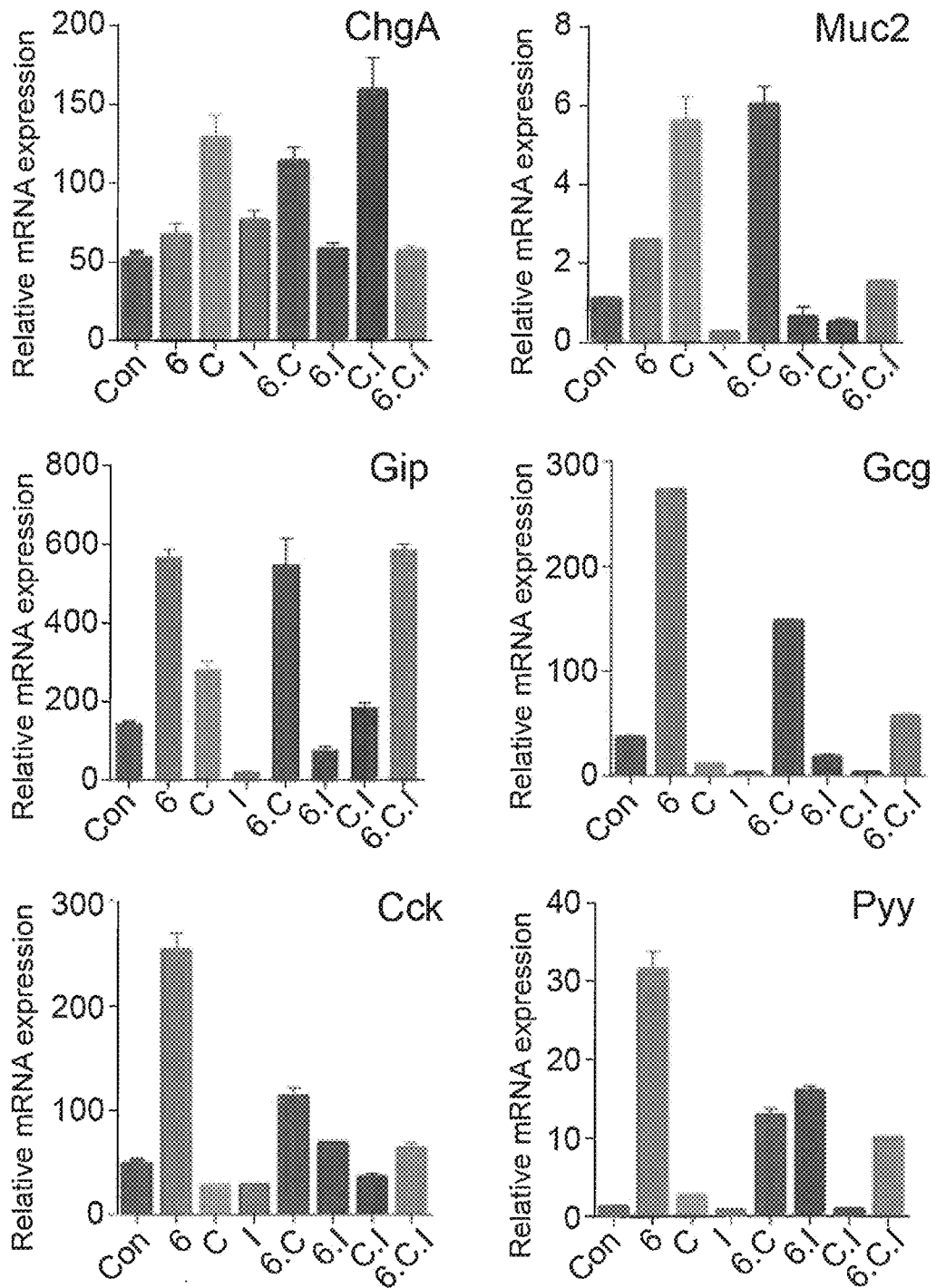
FIG. 22 shows expression of functional EEC markers under multiple conditions.

Expression of Functional EEC Marker Under Multiple Conditions (FIG. 22)

Figure 23:
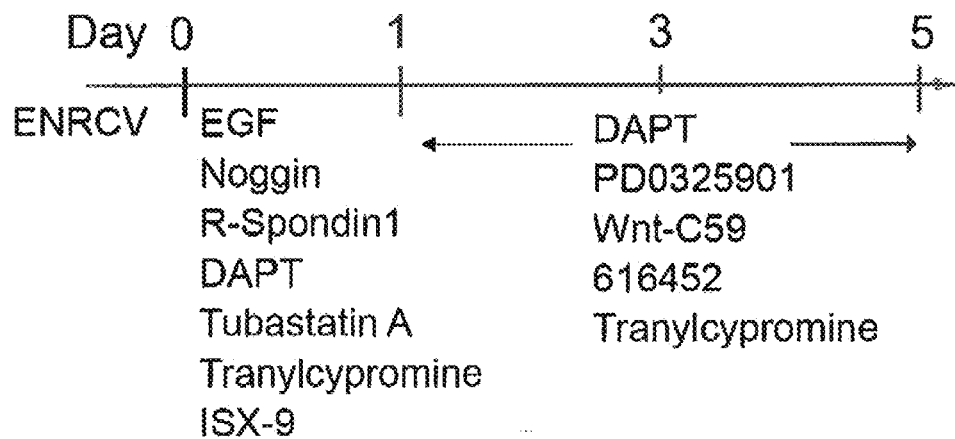
FIG. 23 shows a differentiation protocol for EEC differentiation from ISC.

Tgf-β inhibitor 616452 was found to greatly increase the expression of functional EEC markers such as Gip, Gcg, Cck, Pyy, among others, while ISX9 decreased their expression, as in FIG. 22 showing relative expression to reference gene Hprt. As such, the differentiation protocol was adjusted to include 616452 and remove ISX9 at later stages, as in FIG. 23, showing the differentiation protocol for EEC differentiation from ISC.

Example 26

Converting ChgA Positive EEC Cells to Insulin Producing Cells

Figure 24:
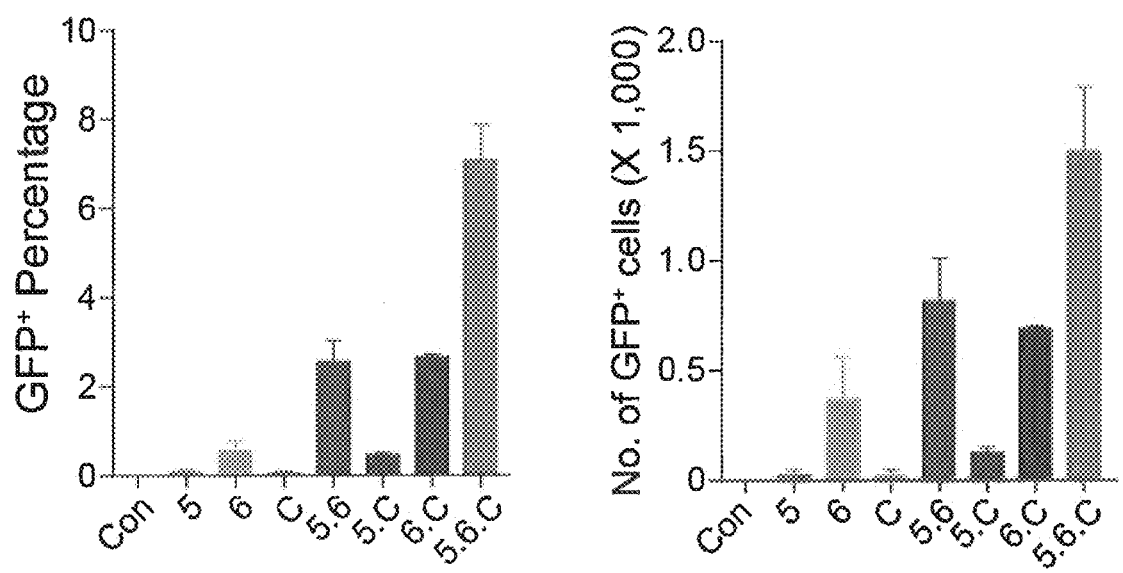
FIG. 24 shows the combination of 5-Aza (5), 616452 (6), and Wnt-C59 (C) induce Insulin-GFP expression in differentiated intestinal stem cells at day 5.

The combination of 5-Aza (5), 616452 (6) and Wnt-C59 (C) induce Insulin-GFP expression in differentiated intestinal stem cells at day 5 (FIG. 24)

Because EEC and insulin producing beta cells share many similarities, recent data indicates that EECs can be converted to insulin producing cells with additional small molecules. Insulin-GFP cells isolated from Insulin-GFP transgenic mice were used to identify small molecules able to induce insulin production. During EEC differentiation from ISCs, Insulin-GFP positive cells were observed when the cells were cultured in the presence of Tgf-β inhibitor 616452, with about 1% of cells becoming GFP positive. Further addition of Wnt inhibitor Wnt-059 and a DNA methylation inhibitor 5-Aza (5-Azacytidine) subsequently increased the percentage of Insulin-GFP+ cells, as in FIG. 24, showing FACS analysis of GFP+ cell percentage and quantification of GFP+ cell number in one well of 24-well plate. Notably, the combination of 56C (5-Aza, 616452, Wnt-C59) results in the highest number of GFP+ cells (see FIG. 24).

Example 27

Figure 25:
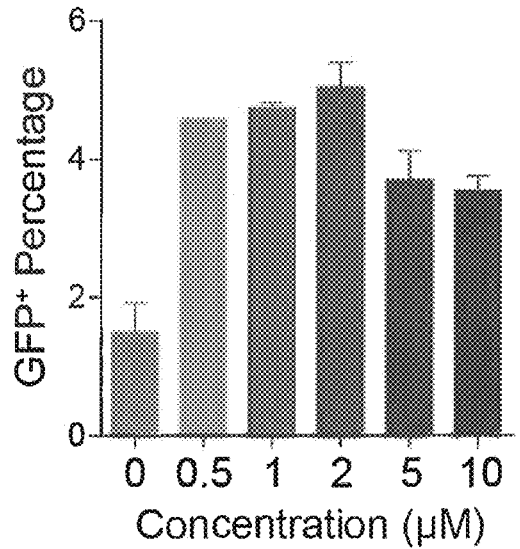
FIG. 25 shows a dose response of 5-Aza in inducing insulin-GFP expression at day 5.
Figure 25:
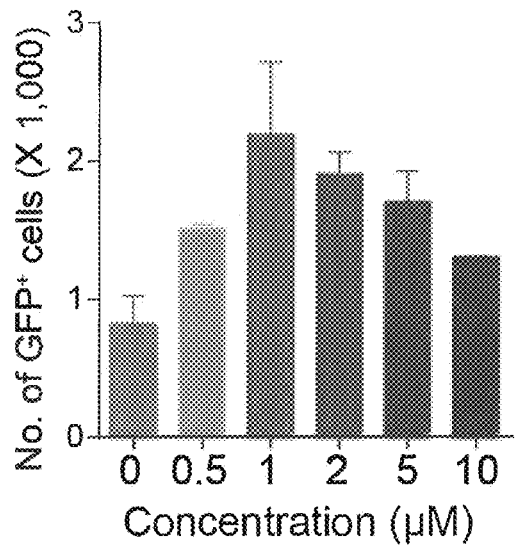

Dose Response of 5-Aza in Inducing Insulin-GFP Expression at Day 5, and Dose Response of 616452 in Inducing Insulin-GFP Expression at Day 5 (FIG. 25)

Figure 26:
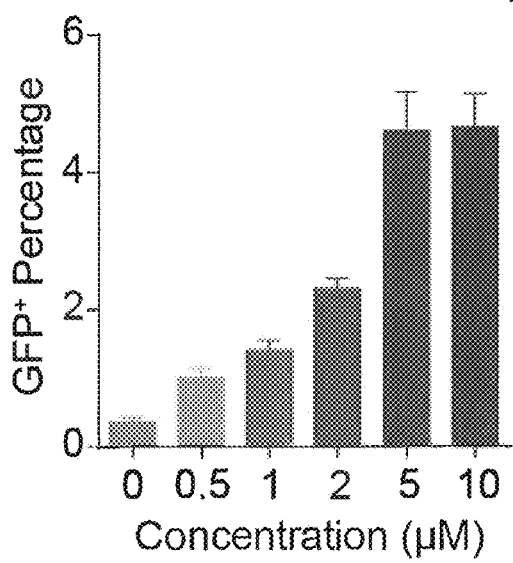
FIG. 26 shows a dose response of 616452 in inducing insulin-GFP expression at day 5.
Figure 26:
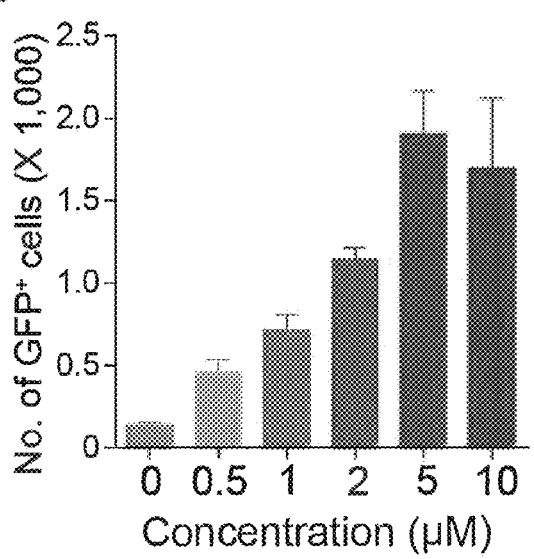

Small molecules 5-Aza and 616452 also induced cell death in the culture, thus, the optimal concentration of 5-Aza (see FIG. 25) and 616452 (see FIG. 26) was determined. From this, 0.5-1 µM of 5-Aza and 5 µM of 616452 were used in future experiments.

Example 28

Figure 27:
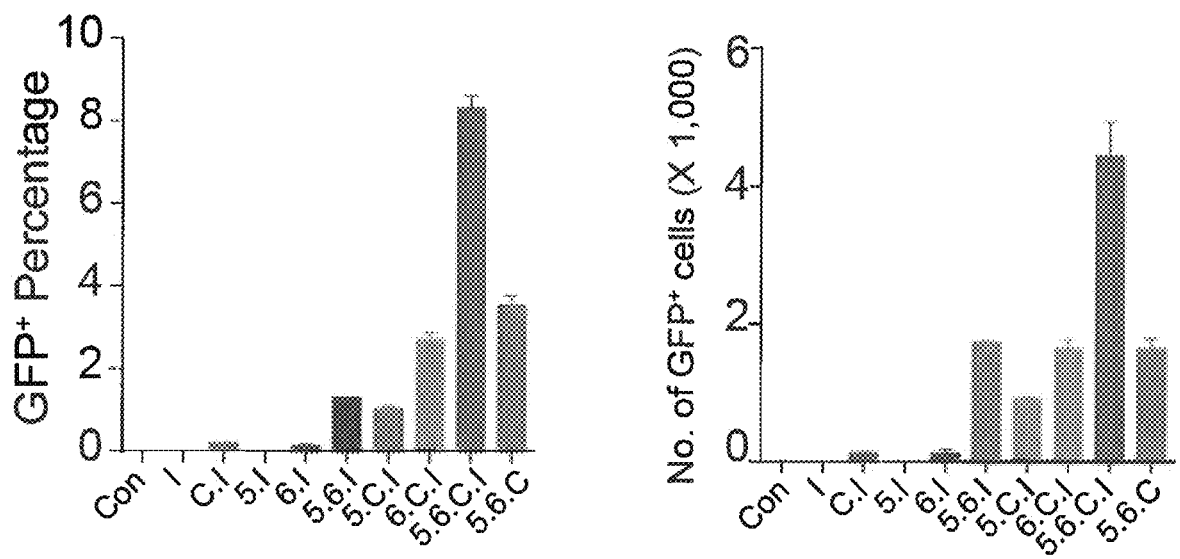
FIG. 27 shows that ISX-9 (I) further increased insulin-GFP expression after 5 days in culture.

ISX-9 (I) Further Increased Insulin-GFP Expression after 5 Days in Culture (FIG. 27)

Figure 28:
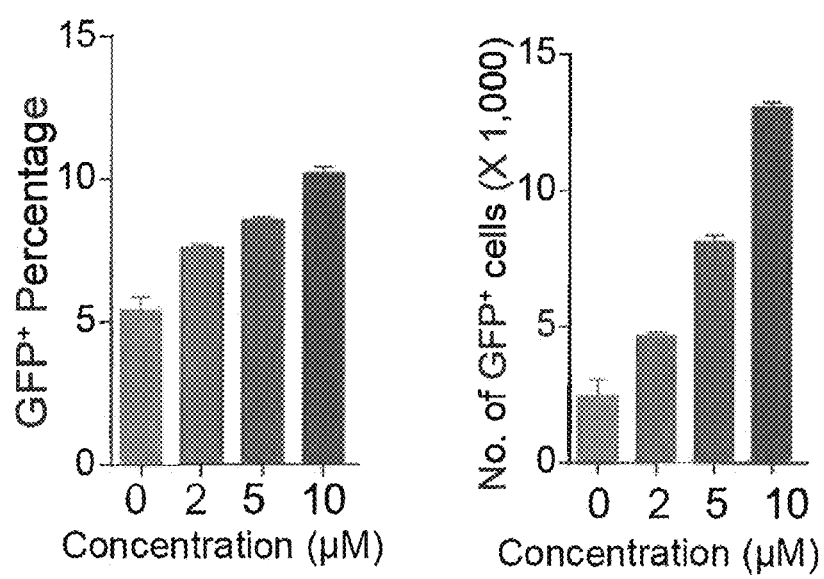
FIG. 28 shows a dose response of ISX-9 in inducing insulin-GFP expression at day 5.

The addition of ISX9 (I) in the combination was also found to further increase the number of GFP+ cells (see FIG. 27), and a concentration of 10 µM was used, as in FIG. 28, where dose response data for ISX-9 in inducing insulin-GFP expression at day 5 is shown.

Example 29

Figure 29:
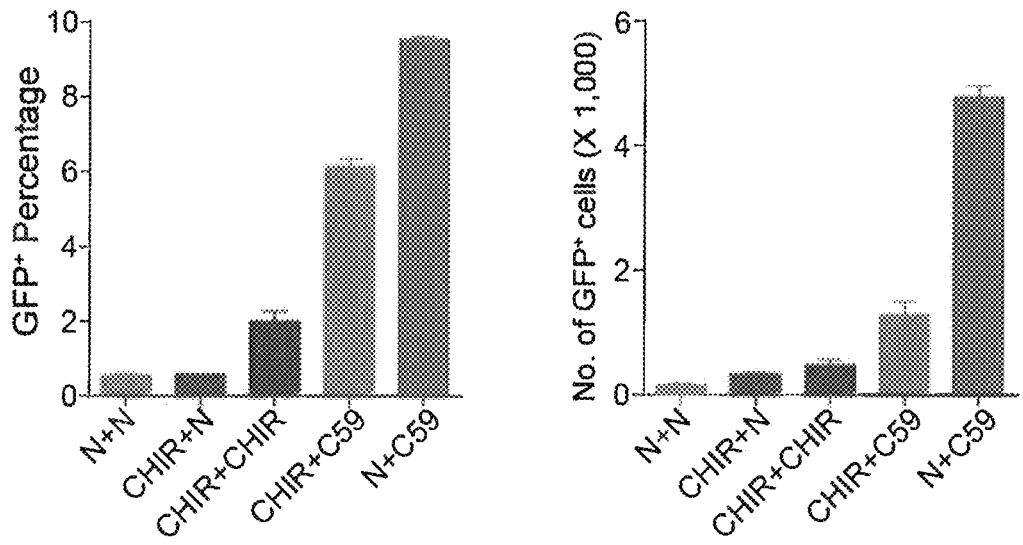
FIG. 29 shows a FACS analysis of Insulin-GFP expression of cells in multiple conditions after 5 days in culture.

FACS Analysis of Insulin-GFP Expression of Cells in Multiple Conditions after 5 Days in Culture (FIG. 29)

Wnt signaling was also tested in the two steps of conversion. Increasing Wnt activation in Step 1 by adding CHIR99021 did not increase GFP expression, while the combination of R-Spondin1 and Wnt-C59 results in highest number of GFP+ cells in the system, as shown in FIG. 29, where N: none; CHIR: CHIR99201; and C59: Wnt-C59.

Example 30

Figure 30:
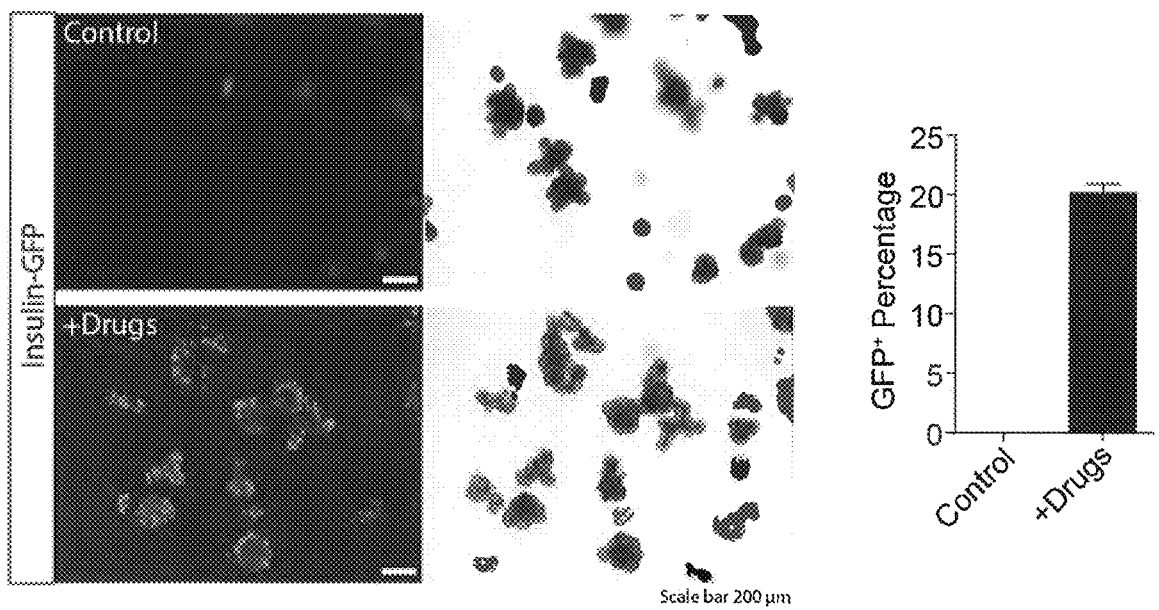
FIG. 30 shows GFP and brightfield of cells treated without or with drugs at day 7.

GFP and Brightfield of Cells Treated without or with Drugs at Day 7 (FIG. 30)

Under the conditions as in Example 29, and after 7 days of differentiation, up to 20% of the cells expressed Insulin-GFP, as shown in FIG. 30, where control: cells cultured in EEC differentiation condition. (ENR.D.Tu.Ty at day 1 and D.Pd.Ty.C59 from Day 2). drugs added include 5-Aza, 616452, and ISX9; Pd was added at day 4 instead of day 2; and scale bars: 200 µm.

Example 31

Gene Expression in the Process (FIG. 31)

Cells turned on expression of major transcription factors that are important for insulin expression, such as Pdx1, Ngn3, Mafa, NeuroD1, Nkx6.1, and Nkx2.2, and greatly increased insulin mRNA expression, as shown in FIG. 31, where control conditions were ENR.D.Tu.Ty.5Aza.616452.ISX9, with 5Aza removed from Day 2; for drug treatment, cells were first cultured with ENR.D.Tu.Ty.5Aza.616452.ISX9, and changed to D.Ty.616452.ISX9.C59 conditions at Day 2, with Pd0325901 added at Day 4; and at day 0, all cells were cultured under ENR.CV conditions.

Example 32

Figure 32:
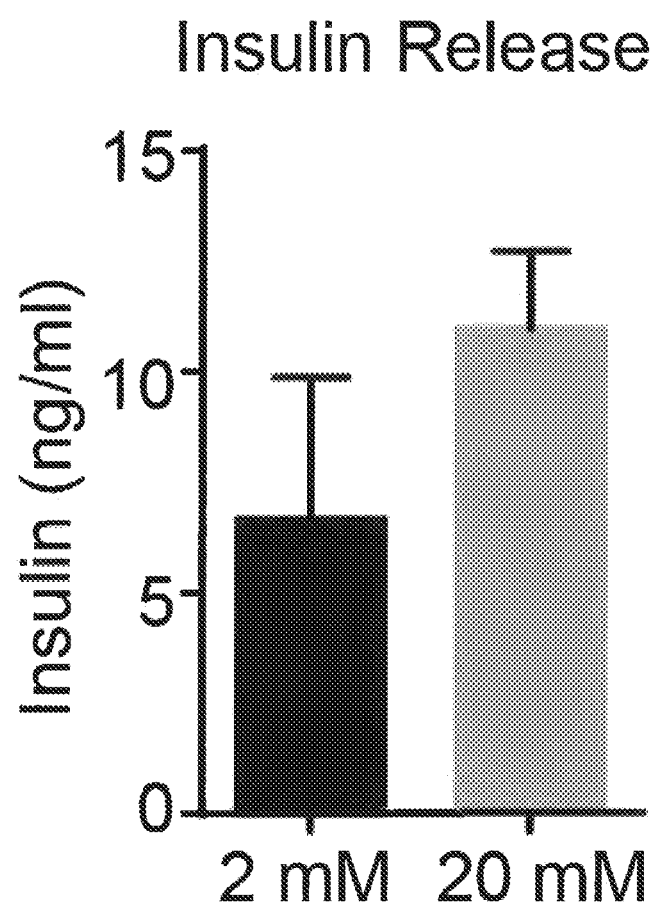
FIG. 32 shows treatment of cells with low (2 mM) and high (20 mM) concentration of glucose induce different levels of insulin release.

Treatment of Cells with Low (2 mM) and High (20 mM) Concentration of Glucose Induce Different Level of Insulin Release (FIG. 32)

Release of insulin from the differentiated cells was tested. Treatment of the cells with glucose induced dose dependent insulin release, suggesting these cells are functional and responsive to glucose, as shown in FIG. 32.

Example 33

Figure 33:
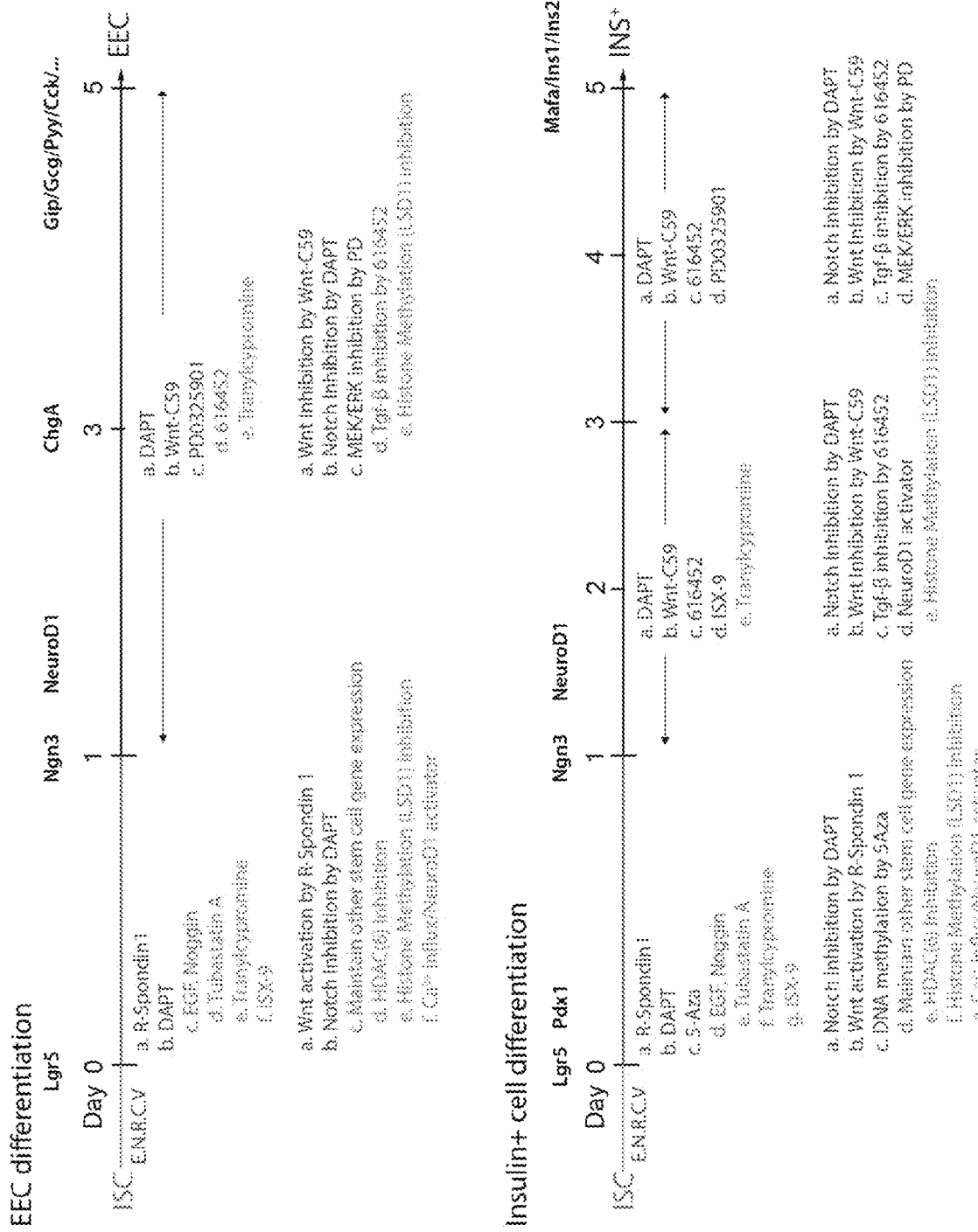
FIG. 33 shows a flow diagram of a differentiation protocol.

Flow Diagram of Differentiation Protocol (FIG. 33)

Factors in blue and green represent important factors. Orange indicates supportive factors. Also listed are key events during differentiation, and key markers for each stage, as shown in FIG. 33.

Example 34

Model of In Vivo EEC Differentiation Controlled by Wnt and Notch Pathways (FIG. 34)

The activity of Notch pathway is modulated through tans-activation or cis-inhibition. The Notch pathway is activated through binding of a Notch receptor with Notch Ligands (DLLs) on neighbor cells (i.e., secretory cells such as Paneth cells, EEC and goblet cells, or secretory cell progenirors). Lose contact with these cells leads to Notch inactivation, which is further enhanced through cis-inhibition. The Wnt pathway is activated through a Wnt ligand gradient derived from cells in the laminal propria, or Paneth cells located at the bottom of crypts. Leave the crypt bottom leads to Wnt inactivation. Notch inactivation also leads to derepression of the Wnt signaling pathway, while attenuation of the Wnt pathway rescues the phenotype associated with Notch blockade. (Tian et al., Cell Reports, 2015). For EEC differentiation, Notch inactivation induced Atoh1 expression and further induced Ngn3 upregulation when Wnt pathway is (moderately) activated (i.e., when Wnt is deactivated before Notch inactivation, Atoh1 will be induced, but not Ngn3, leading to goblet cell differentiation). Ngn3 positive cells further differentiate to EEC upon Wnt inactivation. And continuously (strong) Wnt activation upon Notch inactivation leads to Paneth cell fate. Small molecule drugs such as 5-Aza, Tgf-b inhibitor, ISX-9, or other drugs may act on multiple cell types, including the stem cells, progenitor cells, or differentiated enteroendocrine cells and induce insulin expression in these cells, as shown in FIG. 34.

Example 35

Temporally Combined Chemical Control of High Efficiency Enteroendocrine Cell Differentiation.

In the study described hereinabove, several signaling pathways that play important roles in the specification of EEC were identified. Notch pathway has been shown to determine absorptive or secretory differentiation, and its inactivation is necessary for the specification of secretory cells including goblet cells, Paneth cells, tufts cells and enteroendocrine cells. Further down the differentiation road, Wnt pathway plays important role in goblet cell and Paneth cell fate determination, with its activation inducing Paneth cell fate and its inactivation inducing goblet cell fate. The role of Wnt in EEC differentiation has been less clear. As described herein, Wnt activation is important for Ngn3 expression for the specification of EEC, and subsequent Wnt inactivation helps further differentiation of EEC and maturation of multiple EEC subtypes (FIG. 34).

The differentiation of intestinal stem cells in vivo is a dynamic process, where the cells move upwards (except for Paneth cells) during differentiation. The signaling gradient along the crypt-villus axis influences the fate determination for the differentiating stem and progenitor cells during the differentiation/migration process. While the specification of stem/progenitor cells initiates above the crypt bottom, where cell membrane bounded Wnt ligand (secreted by Paneth cells) was diluted through cell division, the R-Spondin/Lgr signaling module prolong the Wnt activation when the stem cells left contact with niche cells—the Paneth cells (Farin et al, 2016, Nature). This mechanism permits the induction of Ngn3 expression upon Notch inactivation. Thus, the sequence and level of Wnt/Notch inactivation seems to play a role in the fate determination of secretory progenitors. And the location of secretory progenitor cells correspondingly help the cells make the choice. For instance, earlier inactivation of Notch in the presence of low level of Wnt activation may favor a EEC fate due to induction of Ngn3 (e.g. at the +4 position), and earlier inactivation of Wnt signaling followed by inactivation of Notch signaling may promote goblet cell differentiation due to low level of Ngn3 induction (e.g. above +4 position), while strong activation of Wnt signaling and Notch inactivation favors Paneth cell fate (e.g. in the crypts). Thus, the differentiation of EEC and other intestinal epithelial cell types from intestinal stem cells is a spatially and temporally preciously controlled process.

While Wnt and Notch pathways play an instrumental role in stem cell differentiation including EECs, other signaling pathways also participate in the differentiation process. As described herein, the inhibition of EGFR/MEK/ERK signaling cascade increased the level of EEC differentiation, and inhibition of Tgf-0 also greatly promoted the EEC specification and maturation. Epigenetic regulation also takes part in the differentiation process such as HDAC and Histone demethylation. The specific combination of these pathways controls the fate of ISCs and progenitors.

Example 36

Based on the protocol to convert gastrointestinal stem cells into insulin producing cells, a 3-stage process was developed, specifically, Day 0-1 as Stage 1, Day 1-3 as Stage 2, Day 3-5 as Stage 3. After Stage 3, the cells turn on significant level of Insulin expression as indicated by Ins-EGFP expression and qPCR for Insulin mRNA expression. Optionally, the cells can be further cultured for 1-2 weeks, as Stage 4. For each stage, a set of specific combination of small molecules (and/or growth factors) were added. The objective was to optimize the reprogramming protocol to increase insulin expression, specifically Insulin mRNA expression for each stage, by screening and testing new small molecules (or growth factors).

Figure 42:
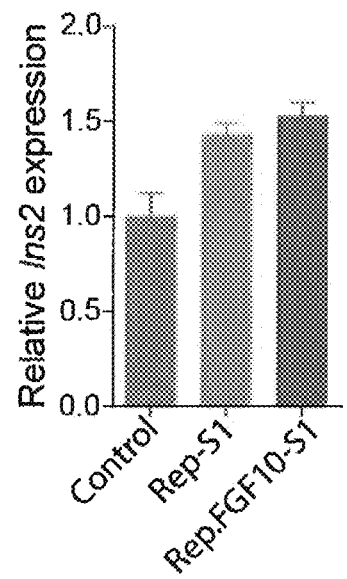
FIG. 42 shows that RepSox and FGF10 increased Insulin mRNA expression when added in Stage 1.

RepSox(616452) was previously added in Stages 2-3. It was found that when RepSox(616452) was added starting from Stage 1 (i.e. added in Stage 1-3), Insulin mRNA (Ins2) was increased as compared when RepSox was added in Stage 2-3. When combined with FGF10 (added in Stage 1), Insulin expression was further increased, as shown in FIG. 42.

Figure 43:
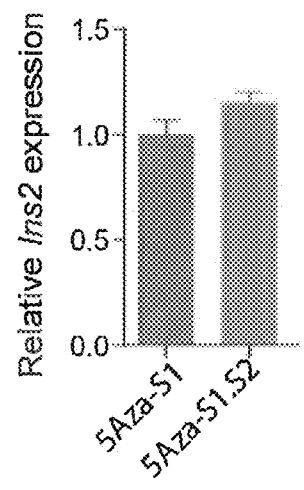
FIG. 43 shows that longer 5Aza treatment increased Insulin mRNA expression.

It was found that when extending the treatment time of 5Aza (5-aza-2'-deoxycytidine) from Stage 1 only to Stage 1 and Stage 2, Insulin mRNA expression was slightly increased (FIG. 43).

Figure 44:
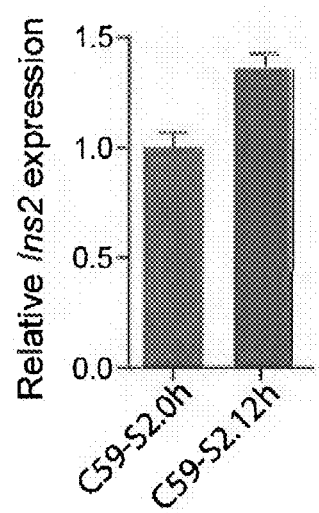
FIG. 44 shows that delayed addition of Wnt-C59 in Stage 2 increased Insulin mRNA expression.

In Stage 2, when the addition of Wnt-C59 was delayed for 12 hours, Insulin mRNA expression was increased. This delayed Wnt inhibition may have permitted a higher level of Ngn3 expression in the cells (as Ngn3 expression requires Wnt activity), which further increases Insulin mRNA expression (FIG. 44).

Figure 45:
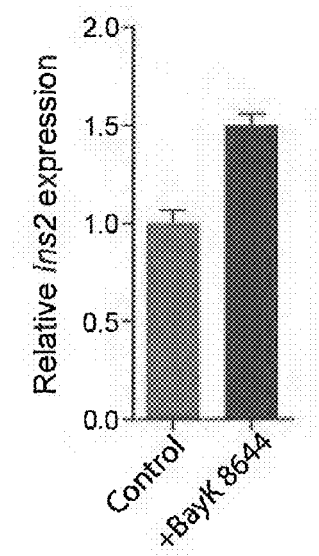
FIG. 45 shows that BayK 8644 increased Insulin mRNA expression when added in Stage 1.

Another small molecule, BayK 8644, which is an L-type Ca2+ channel activator, increased Insulin mRNA expression when added in Stage 1, as shown in FIG. 45.

Figure 46:
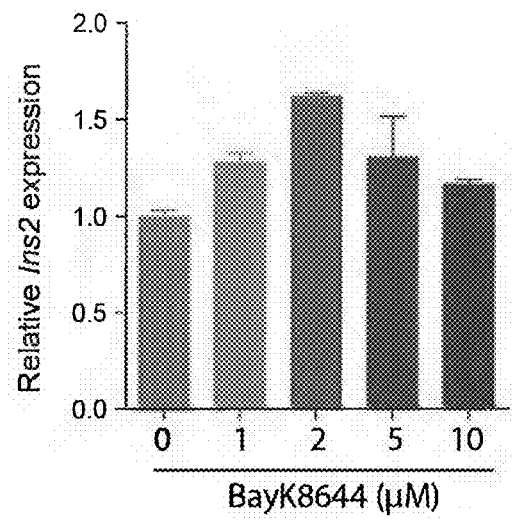
FIG. 46 shows dose-dependent activity of BayK 8644 in promoting Insulin expression.

BayK 8644 showed highested activity when used at 2 µM (FIG. 46).

Figure 47:
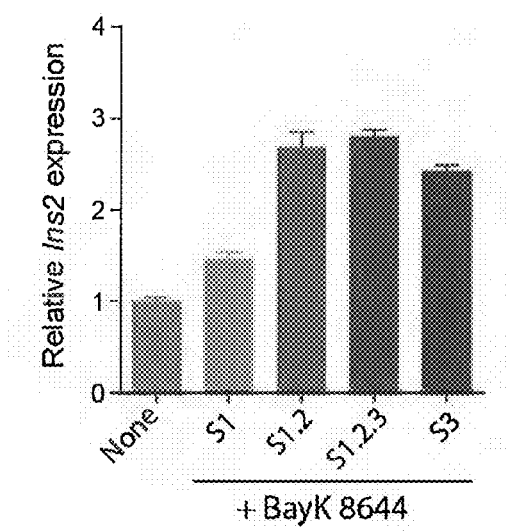
FIG. 47 shows that BayK 8644 increased Insulin mRNA expression when added in Stages 1-3.

BayK 8644 treatment showed highest activity when added in Stages 1-3 (FIG. 47).

Figure 48:
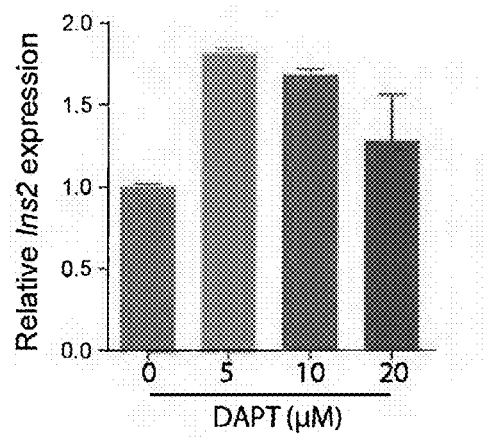
FIG. 48 shows dose-dependent activity of DAPT in promoting Insulin expression.

The optimal concentration of DAPT was 5 µM (FIG. 48).

Nkx6.1 is an important transcription factor for Insulin expression and Islet function. Additional factors were tested for an ability to increase Nkx6.1 expression as well as Insulin expression.

Figure 49:
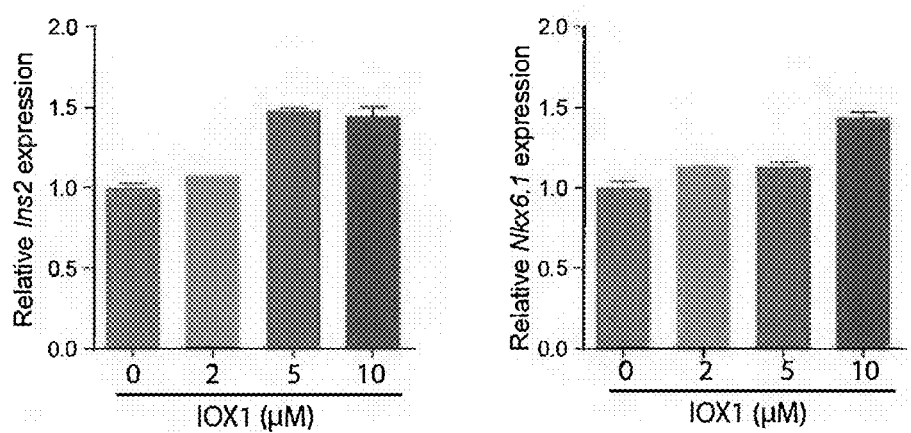
FIG. 49 shows that IOX1 increased insulin and Nkx6.1 expression.

IOX1, which is a Histone demethylase JMJD inhibitor, increased Insulin and Nkx6.1 expression when used at 5-10 µM (FIG. 49)

Figure 50:
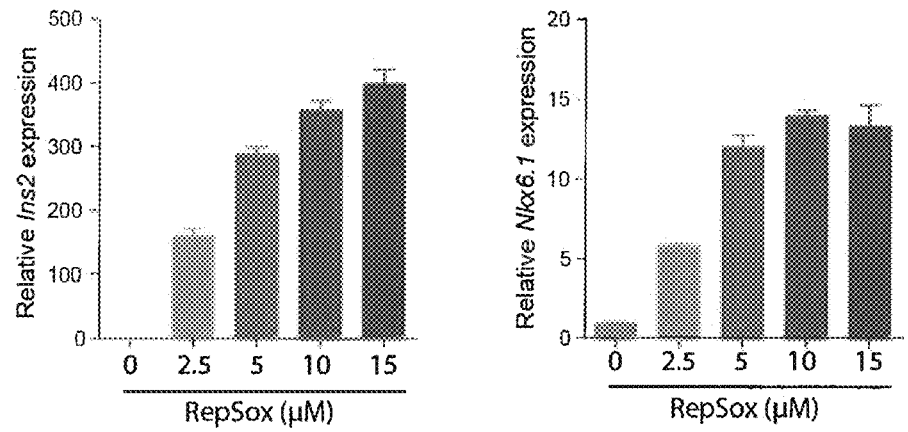
FIG. 50. shows a dose response of RepSox in promoting insulin and Nkx6.1 expression.
Figure 51:
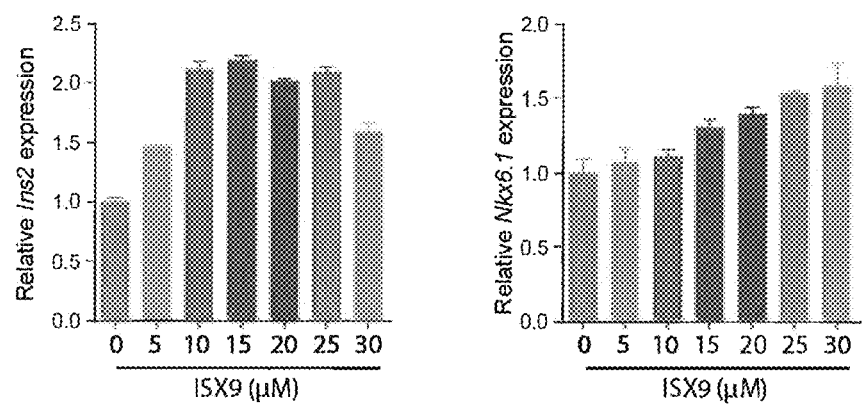
FIG. 51 shows a dose response of ISX9 in promoting insulin and Nkx6.1 expression.

The effects of RepSox and ISX9 were also tested to identify optimal concentration in promoting insulin and Nkx6.1 expression. It was found that the optimal dose of RepSox was 10-15 µM and ISX9 was 10-20 µM in promoting Insulin and Nkx6.1 expression (FIGS. 50-51).

Figure 52:
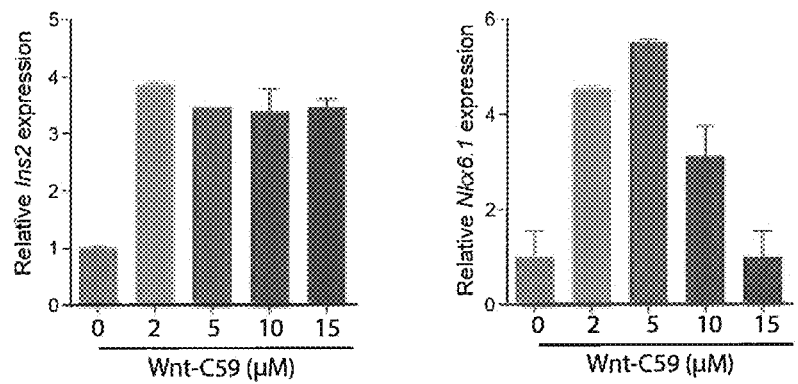
FIG. 52 shows a dose response of Wnt-C59 in promoting insulin and Nkx6.1 expression.

For Wnt-C59, the optimal dose was 5 (FIG. 52).

Figure 53:
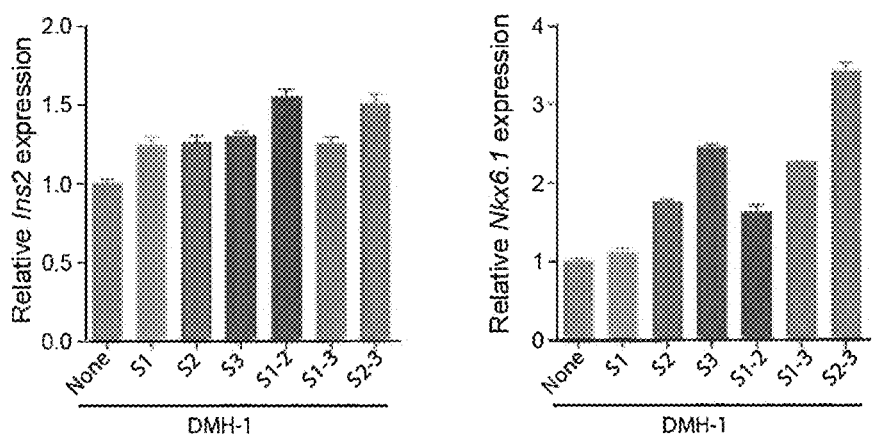
FIG. 53 shows that DMH-1 increased insulin and Nkx6.1 expression level when added in Stage 2-3.

In addition, it was found that the Bone Morphogenic Protein (BMP) ALK2 receptor inhibitor DMH-1 increased the expression of Nkx6.1 as well as insulin, when added in Stages 2-3 (FIG. 53).

Figure 54:
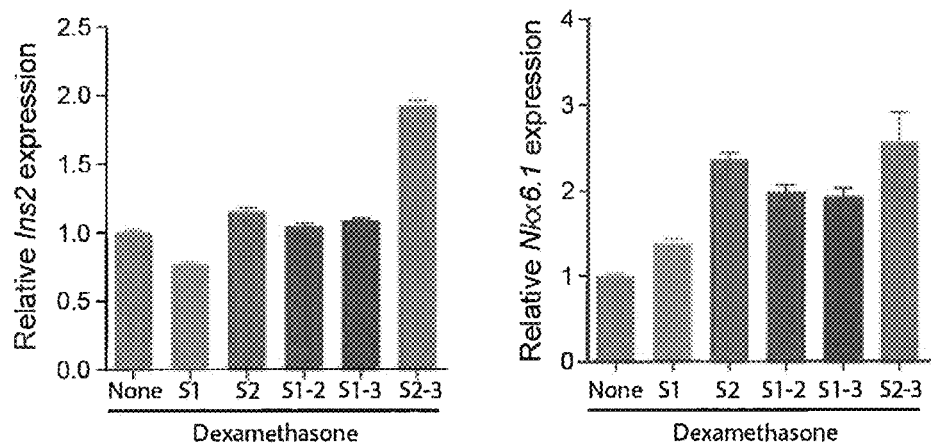
FIG. 54 shows that Dexamethasone increased insulin and Nkx6.1 expression level when added in Stage 2-3.

In addition, Dexamethasone also increased Nkx6.1 and Insulin expression when added in Stages 2-3 (FIG. 54).

Vitamin C had beneficial effects when added in Stage 2-3.

The ability of additional small molecules (growth factors) to promote insulin expression in Stage 3 was further tested.

Figure 55:
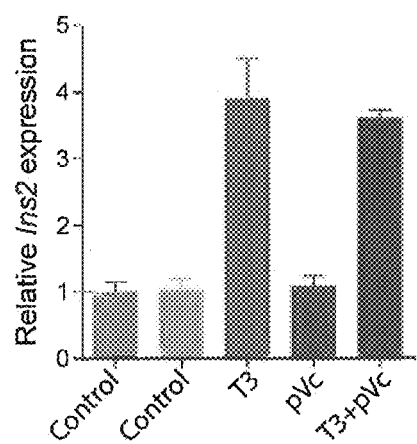
FIG. 55 shows that T3 increased Insulin mRNA expression when added in Stage 3.

When small molecule T3 (Triiodothyronine) was added in Stage 3, it greatly increased Insulin mRNA expression. While Vitamin C (pVc) did not show such effect, as shown in FIG. 55.

Figure 56:
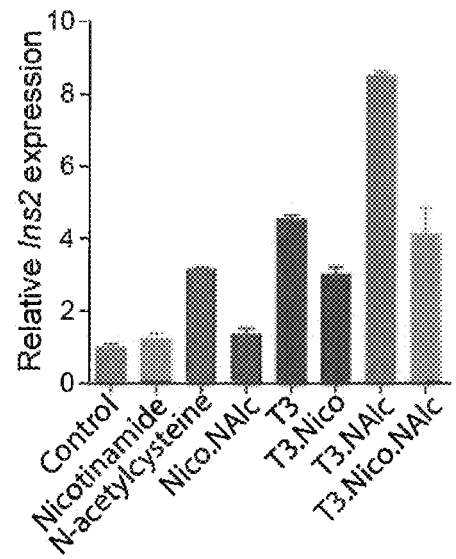
FIG. 56 shows that T3 and N-acetylcysteine (N-Alc) increased Insulin mRNA expression when added in Stage 3.

Similarly, additional molecules including N-Acetylcysteine (2 mM) also increased Insulin mRNA expression, and further increased Insulin expression when combined with T3, as shown in FIG. 56.

Figure 57:
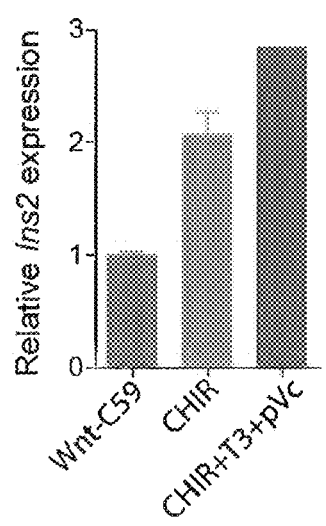
FIG. 57 shows that CHIR99021 (CHIR) increased Insulin mRNA expression when added in Stage 3.

It was also found that by switching Wnt-C59 with CHIR99021 (CHIR) in Stage 3, insulin mRNA was greatly increased, as shown in FIG. 57. When CHIR and T3 are combined, Insulin mRNA was further increased.

Figure 58:
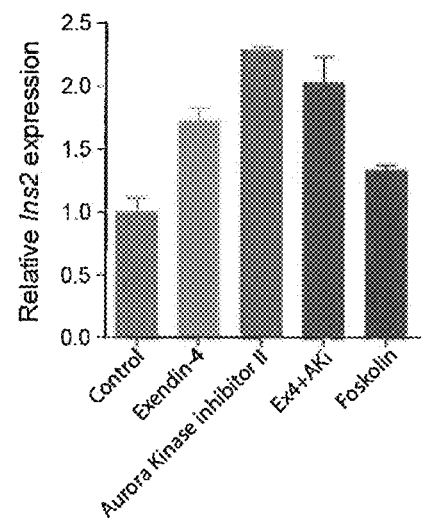
FIG. 58 shows that Exendin-4 and Aurora Kinase Inhibitor II, as well as Forskolin increased Insulin mRNA expression.

Additional small molecules or factors including Exendin-4 (Ex4) and Aurora Kinase Inhibitor II (AKi) were identified to increase Insulin mRNA expression, as shown in FIG. 58. It was also found that Forskolin (50-100 µM) improved cell survival when added in Stage 3.

Figure 59:
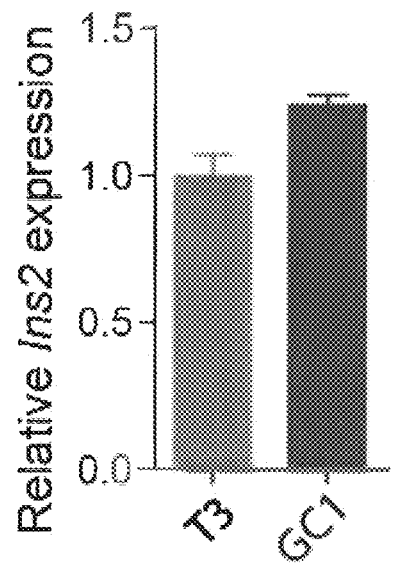
FIG. 59. shows that GC1 can replace T3 in promoting Insulin mRNA expression.

In addition, thyroid hormone beta-receptor agonist GC-1 was used to replace T3 and showed a similar effect in promoting insulin mRNA expression (FIG. 59).

Figure 60:
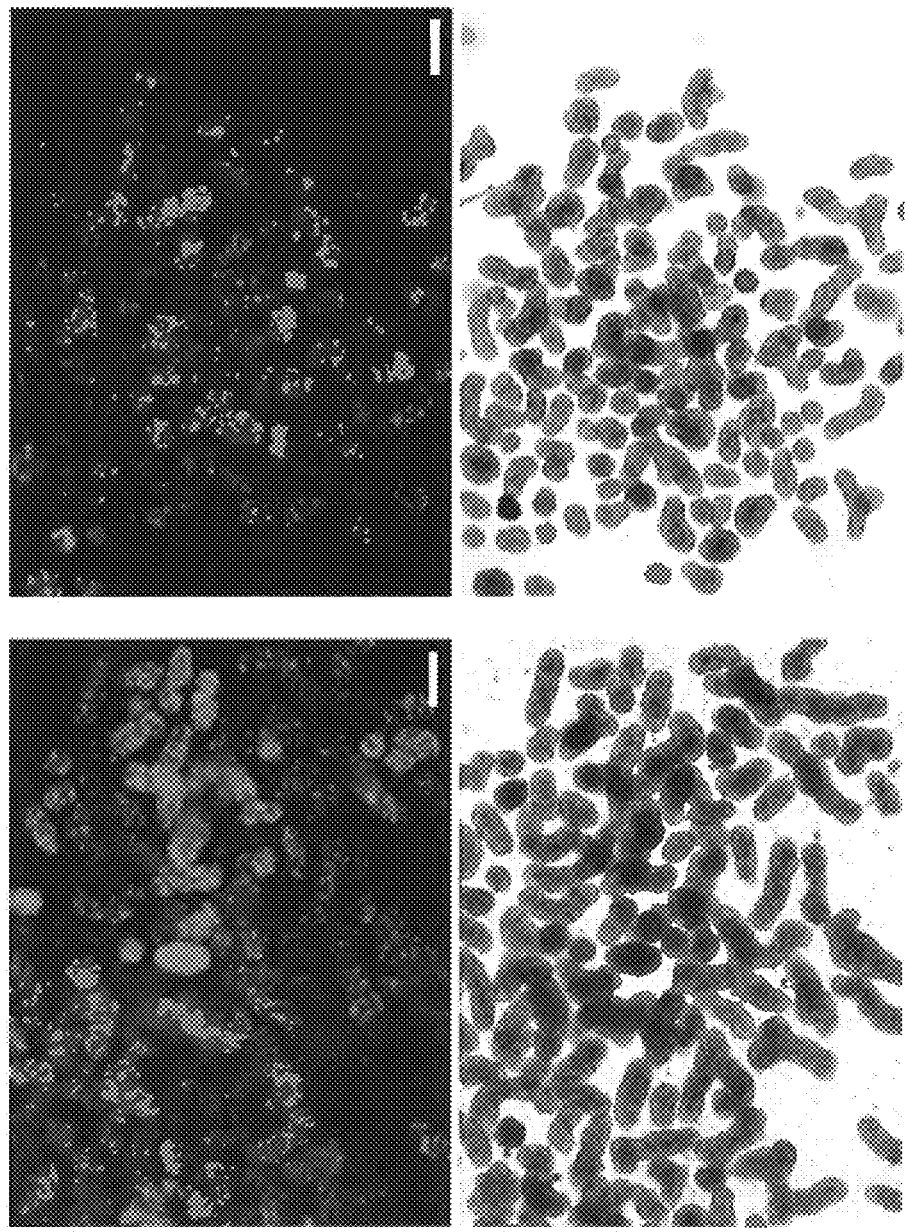
FIG. 60 shows Insulin-GFP expression and morphology of islet-like structures obtained using combination of factors, from gastrointestinal stem cells.

By using a combination of these identified factors, insulin expression and insulin-GFP expression was induced in 5 days from intestinal stem cells. Continue culturing the cells further increased insulin expression level and led to islet-like cell colonies as shown in FIG. 60.

Figure 61:
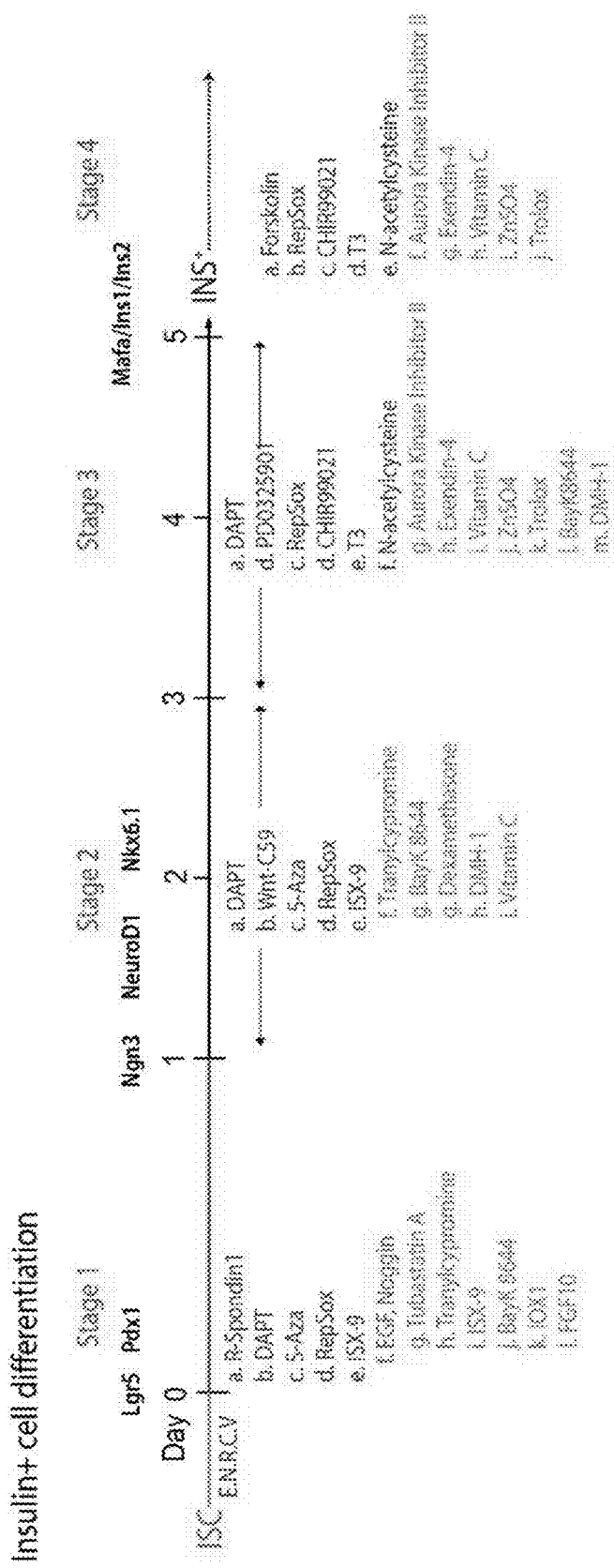
FIG. 61 shows a diagram of a cell culture process.

For continuing culture of Islet-like Insulin expression cell colonies, it was found that the addition of Forskolin increased cell survival. Factors including DAPT, PD0325901, BayK8644, DMH-1 could be removed without much influence, as shown in FIG. 61.

Additional data for EEC differentiation.

Based on observations as described herein, a modified flow diagram for EEC differentiation was developed (FIG. 61) as indicated below.

Major differences:
1. Add RepSox(616452) start from Day 0 instead of Day 1.
2. ISX-9 changed to optional, and not used in protocol as described in EEC-V6.docx.
3. Repsox changed to essential factors as it greatly increased EEC differentiation as described in EEC-V6.docx.
4. Wnt-C59 added at 36 h from Day 0.

From the foregoing description, it will be apparent that variations and modifications may be made to the disclosure described herein to adopt it to various usages and conditions. Methods and materials are described herein for use in the present disclosure; other, suitable methods and materials known in the art can also be used. The materials, methods, and examples are illustrative only and not intended to be limiting. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. The teachings of all patents, published applications and references cited herein are incorporated by reference in their entirety. While this invention has been particularly shown and described with references to example embodiments thereof, it will be understood by those skilled in the art that various changes in form and details may be made therein without departing from the scope of the invention encompassed by the appended claims.

INCORPORATION BY REFERENCE AND EQUIVALENTS

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

REFERENCES

Barker, N., van Es, J. H., Kuipers, J., Kujala, P., van den Born, M., Cozijnsen, M., Haegebarth, A., Korving, J., Begthel, H., Peters, P. J., et al. (2007). Identification of stem cells in small intestine and colon by marker gene Lgr5. Nature 449, 1003-1007.

Farin, H. F., Van Es, J. H., and Clevers, H. (2012). Redundant sources of Wnt regulate intestinal stem cells and promote formation of Paneth cells. Gastroenterology 143, 1518-1529 e1517.

Formeister, E. J., Sionas, A. L., Lorance, D. K., Barkley, C. L., Lee, G. H., and Magness, S. T. (2009). Distinct SOX9 levels differentially mark stem/progenitor populations and enteroendocrine cells of the small intestine epithelium. Am J Physiol Gastrointest Liver Physiol 296, G1108-1118.

Furness, J. B., Rivera, L. R., Cho, H. J., Bravo, D. M., and Callaghan, B. (2013). The gut as a sensory organ. Nat Rev Gastroenterol Hepatol 10, 729-740.

Gribble, F. M., and Reimann, F. (2015). Enteroendocrine Cells: Chemosensors in the Intestinal Epithelium. Annu Rev Physiol.

Gunawardene, A. R., Corfe, B. M., and Staton, C. A. (2011). Classification and functions of enteroendocrine cells of the lower gastrointestinal tract. Int J Exp Pathol 92, 219-231.

Lee, C. S., Perreault, N., Brestelli, J. E., and Kaestner, K. H. (2002). Neurogenin 3 is essential for the proper specification of gastric enteroendocrine cells and the maintenance of gastric epithelial cell identity. Genes Dev 16, 1488-1497.

Sato, T., and Clevers, H. (2013). Growing self-organizing mini-guts from a single intestinal stem cell: mechanism and applications. Science 340, 1190-1194.

Sato, T., van Es, J. H., Snippert, H. J., Stange, D. E., Vries, R. G., van den Born, M., Barker, N., Shroyer, N. F., van de Wetering, M., and Clevers, H. (2011). Paneth cells constitute the niche for Lgr5 stem cells in intestinal crypts. Nature 469, 415-418.

Sato, T., Vries, R. G., Snippert, H. J., van de Wetering, M., Barker, N., Stange, D. E., van Es, J. H., Abo, A., Kujala, P., Peters, P. J., et al. (2009). Single Lgr5 stem cells build crypt-villus structures in vitro without a mesenchymal niche. Nature 459, 262-265.

Tian, H., Biehs, B., Chiu, C., Siebel, C. W., Wu, Y., Costa, M., de Sauvage, F. J., and Klein, O. D. (2015). Opposing activities of Notch and Wnt signaling regulate intestinal stem cells and gut homeostasis. Cell Rep 11, 33-42.

VanDussen, K. L., Carulli, A. J., Keeley, T. M., Patel, S. R., Puthoff, B. J., Magness, S. T., Tran, I. T., Maillard, I., Siebel, C., Kolterud, A., et al. (2012). Notch signaling modulates proliferation and differentiation of intestinal crypt base columnar stem cells. Development 139, 488-497.

Yin, X., Farin, H. F., van Es, J. H., Clevers, H., Langer, R., and Karp, J. M. (2014). Niche-independent high-purity cultures of Lgr5+ intestinal stem cells and their progeny. Nat Methods 11, 106-112.

Mumphrey, M. B., et al., *Roux-en-Y gastric bypass surgery increases number but not density of CCK-, GLP-1-, 5-HT-, and neurotensin-expressing enteroendocrine cells in rats.* Neurogastroenterol Motil, 2013. 25(1): p. e70-9.

Moran, G. W., et al., *Enteroendocrine cells: neglected players in gastrointestinal disorders?* Therap Adv Gastroenterol, 2008. 1(1): p. 51-60.

Bogunovic, M., et al., *Enteroendocrine cells express functional Toll-like receptors.* Am J Physiol Gastrointest Liver Physiol, 2007. 292(6): p. G1770-83.

Worthington, J. J., *The intestinal immunoendocrine axis: novel cross-talk between enteroendocrine cells and the immune system during infection and inflammatory disease.* Biochem Soc Trans, 2015. 43(4): p. 727-33.

Manocha, M. and W. I. Khan, *Serotonin and GI Disorders: An Update on Clinical and Experimental Studies.* Clin Transl Gastroenterol, 2012. 3: p. e13.

Sternini, C., L. Anselmi, and E. Rozengurt, *Enteroendocrine cells: a site of 'taste' in gastrointestinal chemosensing.* Curr Opin Endocrinol Diabetes Obes, 2008. 15(1): p. 73-8.

van der Flier, L. G. and H. Clevers, *Stem cells, self-renewal, and differentiation in the intestinal epithelium.* Annu Rev Physiol, 2009. 71: p. 241-60.

Petersen, N., et al., *Generation of L cells in mouse and human small intestine organoids.* Diabetes, 2014. 63(2): p. 410-20.

Beucher, A., et al., *The homeodomain-containing transcription factors Arx and Pax4 control enteroendocrine subtype specification in mice.* PLoS One, 2012. 7(5): p. e36449.

What is claimed is:

1. A method for obtaining a population of enteroendocrine cells (EECs) from mammalian LGR5 positive epithelial stem cells, the method comprising:
   a) adding the LGR5 positive epithelial stem cells to a cell culture medium comprising a Notch inhibitor and a Wnt activator to form a first resultant cell population; and
   b) adding the first resultant cell population to a cell culture medium comprising a Notch inhibitor and at least one of an EGFR inhibitor and a MEK/ERK inhibitor without a Wnt activator, thereby forming a population of EECs.

2. The method of claim 1, wherein the Wnt activator is R-Spondin1, the Notch inhibitor is N—[N-(3,5-Difluorophenacetyl)-L-alanyl]-S-phenylglycine t-butyl ester (DAPT) or a pharmaceutically acceptable salt thereof, and the MEK/ERK inhibitor is N-[(2R)-2,3-Dihydroxypropoxy]-3,4-difluoro-2-[(2-fluoro-4-iodophenyl)amino]-benzamide or a pharmaceutically acceptable salt thereof.

3. The method of claim 1, wherein the cell culture medium of b) further comprises a Wnt inhibitor.

4. The method of claim 3, wherein the Wnt inhibitor comprises a compound having the following structure:

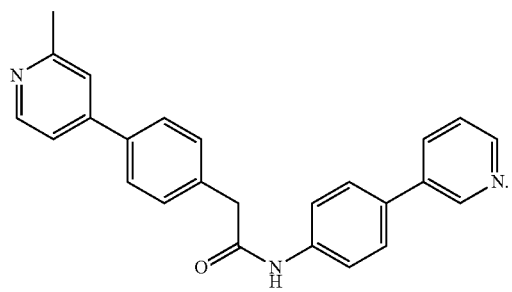

5. The method of claim 1, wherein the cell culture medium of a) further comprises at least one of epidermal growth factor (EGF) and Noggin, or wherein the cell culture medium of b) further comprises at least one of EGF or Noggin.

6. The method of claim 1, wherein the cell culture medium of a) further comprises at least one of a histone deacetylase (HDAC) inhibitor, a Histone Methylation Inhibitor, and a Ca2+/NeuroD1 activator, or a pharmaceutically acceptable salt thereof.

7. The method of claim 6, wherein the cell culture medium of a) further comprises at least one of Tubastatin A, tranylcypromine and N-cyclopropyl-5-(2-thienyl)-3-isoxazolecarboxamide, or a pharmaceutically acceptable salt thereof.

8. The method of claim 1, wherein:
   the cell culture medium of a) further comprises a TGF-β inhibitor or a pharmaceutically acceptable salt thereof; or
   the cell culture medium of b) further comprises a TGF-β inhibitor or a pharmaceutically acceptable salt thereof.

9. The method of claim 8, wherein the cell culture medium of b) further comprises a compound having the following structure:

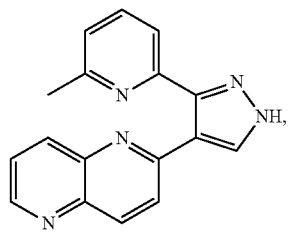 [SMILES: Cc1cccc(-c2n[nH]cc2-c2ccc3ncccc3n2)n1]

or a pharmaceutically acceptable salt thereof.

10. The method of claim 1 wherein the cell culture medium of b) further comprises a histone methylation inhibitor, or a pharmaceutically acceptable salt thereof.

11. The method of claim 10, wherein the cell culture medium of b) further comprises tranylcypromine, or a pharmaceutically acceptable salt thereof.

12. The method of claim 1, wherein the first resultant cell population exhibits increased Neurogenin-3 expression compared to the LGR5 positive epithelial stem cells, and the population of EECs exhibits decreased Neurogenin-3 expression compared to the first resultant cell population.

13. The method of claim 1, wherein the mammalian LGR5 positive epithelial stem cells comprise at least one of stomach stem cells, intestinal stem cells, hematopoietic stem cells, mammary stem cells, mesenchymal stem cells, endothelial stem cells, and neural stem cells.

14. The method of claim 13, wherein the mammalian LGR5 positive epithelial stem cells are intestinal stem cells.

15. A method for obtaining a population of enteroendocrine cells (EECs) from mammalian LGR5 positive epithelial stem cells, the method comprising:
 a) adding the LGR5 positive epithelial stem cells to a cell culture medium comprising a Notch inhibitor and a Wnt activator to form a first resultant cell population; and
 b) adding the first resultant cell population to a cell culture medium comprising a Notch inhibitor without a Wnt activator, thereby forming a population of EECs.

16. The method of claim 15, wherein the Wnt activator is R-Spondin1, and the Notch inhibitor is N—[N-(3,5-Difluorophenacetyl)-L-alanyl]-S-phenylglycine t-butyl ester (DAPT) or a pharmaceutically acceptable salt thereof.

17. The method of claim 15, wherein the cell culture medium of b) further comprises a Wnt inhibitor.

18. The method of claim 17, wherein the Wnt inhibitor comprises a compound having the following structure:

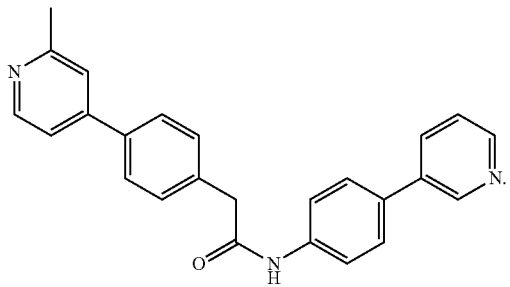 [SMILES: Cc1cc(-c2ccc(CC(=O)Nc3ccc(-c4cccnc4)cc3)cc2)ccn1]

19. The method of claim 15, wherein the cell culture medium of a) further comprises at least one of epidermal growth factor (EGF) and Noggin, or wherein the cell culture medium of b) further comprises at least one of EGF or Noggin.

20. The method of claim 15, wherein the cell culture medium of a) further comprises at least one of a histone deacetylase (HDAC) inhibitor, a Histone Methylation Inhibitor, and a Ca2+/NeuroD1 activator, or a pharmaceutically acceptable salt thereof.

21. The method of claim 20, wherein the cell culture medium of a) further comprises at least one of Tubastatin A, tranylcypromine and N-cyclopropyl-5-(2-thienyl)-3-isoxazolecarboxamide, or a pharmaceutically acceptable salt thereof.

22. The method of claim 15, wherein the cell culture medium of b) further comprises a TGF-β inhibitor or a pharmaceutically acceptable salt thereof.

23. The method of claim 22, wherein the cell culture medium of b) further comprises a compound having the structure:

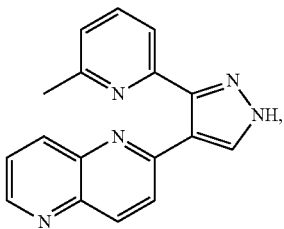 [SMILES: Cc1cccc(-c2n[nH]cc2-c2ccc3ncccc3n2)n1]

or a pharmaceutically acceptable salt thereof.

24. The method of claim 15 wherein the cell culture medium of b) further comprises a histone methylation inhibitor or a pharmaceutically acceptable salt thereof.

25. The method of claim 24, wherein the cell culture medium of b) further comprises tranylcypromine or a pharmaceutically acceptable salt thereof.

26. The method of claim 15, wherein the first resultant cell population exhibits increased Neurogenin-3 expression compared to the LGR5 positive epithelial stem cells, and the population of EECs exhibits decreased Neurogenin-3 expression compared to the first resultant cell population.

27. The method of claim 15, wherein the mammalian LGR5 positive epithelial stem cells comprise at least one of stomach stem cells, intestinal stem cells, hematopoietic stem cells, mammary stem cells, mesenchymal stem cells, endothelial stem cells, and neural stem cells.

28. The method of claim 27, wherein the mammalian LGR5 positive epithelial stem cells are intestinal stem cells.

29. The method of claim 15, wherein the cell culture medium of b) further comprises an MEK/ERK inhibitor, wherein the MEK/ERK inhibitor is N-[(2R)-2,3-Dihydroxypropoxyl]-3,4-difluoro-2-[(2-fluoro-4-iodophenyl)amino]-benzamide.

* * * * *